(12) United States Patent
Geddes et al.

(10) Patent No.: US 8,886,464 B2
(45) Date of Patent: Nov. 11, 2014

(54) MICROWAVE-ACCELERATED METAL-ENHANCED DETECTION METHOD

(75) Inventors: Chris D. Geddes, Bel-Air, MD (US); Kadir Aslan, Baltimore, MD (US)

(73) Assignee: University of Maryland, Baltimore County, Baltimore, MD (US)

( * ) Notice: Subject to any disclaimer, the term of this patent is extended or adjusted under 35 U.S.C. 154(b) by 2099 days.

(21) Appl. No.: 11/695,397

(22) Filed: Apr. 2, 2007

(65) Prior Publication Data

US 2012/0107952 A1 May 3, 2012

Related U.S. Application Data

(63) Continuation-in-part of application No. PCT/US2006/000029, filed on Jan. 3, 2006.

(60) Provisional application No. 60/641,245, filed on Jan. 3, 2005, provisional application No. 60/788,237, filed on Mar. 31, 2006.

(51) Int. Cl.
| | |
|---|---|
| *G01N 33/48* | (2006.01) |
| *C12Q 1/54* | (2006.01) |
| *G01N 33/66* | (2006.01) |
| *G01N 33/543* | (2006.01) |
| *B82Y 15/00* | (2011.01) |
| *B82Y 20/00* | (2011.01) |
| *G01N 21/64* | (2006.01) |
| *G01N 21/78* | (2006.01) |
| *G01N 21/17* | (2006.01) |

(52) U.S. Cl.
CPC ............. *B82Y 15/00* (2013.01); *G01N 21/6489* (2013.01); *C12Q 1/54* (2013.01); *G01N 33/66* (2013.01); *G01N 21/78* (2013.01); *G01N 33/54373* (2013.01); *G01N 2021/1731* (2013.01); *B82Y 20/00* (2013.01); *G01N 21/648* (2013.01)
USPC .......................................................... 702/19

(58) Field of Classification Search
None
See application file for complete search history.

(56) References Cited

U.S. PATENT DOCUMENTS

| 5,017,009 | A | 5/1991 | Schutt et al. |
| 5,449,918 | A | 9/1995 | Krull et al. |
| 5,866,433 | A | 2/1999 | Schalkhammer et al. |
| 7,253,452 | B2 | 8/2007 | Steckel et al. |
| 7,348,182 | B2 | 3/2008 | Martin et al. |
| 7,351,590 | B2 | 4/2008 | Martin |
| 7,718,445 | B2 | 5/2010 | Martin |
| 8,114,598 | B2 * | 2/2012 | Geddes et al. ............... 435/6.11 |
| 2003/0228682 | A1 | 12/2003 | Lakowicz et al. |
| 2004/0039158 | A1 | 2/2004 | Lakowicz et al. |
| 2004/0160606 | A1 | 8/2004 | Lakowicz et al. |
| 2005/0053974 | A1 | 3/2005 | Lakowicz et al. |
| 2005/0202464 | A1 | 9/2005 | Lakowicz et al. |
| 2006/0147927 | A1 | 7/2006 | Geddes et al. |
| 2007/0269826 | A1 | 11/2007 | Geddes et al. |
| 2008/0096281 | A1 | 4/2008 | Geddes et al. |
| 2009/0022766 | A1 | 1/2009 | Geddes |

FOREIGN PATENT DOCUMENTS

| WO | 89/09408 | 10/1989 |
| WO | WO 02/14868 | 2/2002 |
| WO | WO 2004/059279 | 7/2004 |
| WO | WO 2006/137945 | 12/2006 |

OTHER PUBLICATIONS

Maier et al. (Proceedings of SPIE, 2001, vol. 4456, pp. 1-9).*
Cao et al. (J. Am. Chem. Soc. 2001, 123, 7961-7962).*
Seelenbinder et al. (Anal. Chem. 1999, 71, 1963-1966).*
Malicka et al. (J Biomol Screen. Apr. 2004 ; 9(3): 208-215).*
Asian et al. (Anal. Chem. 2005, 77: 8057-8067; Online Pub. Date: Nov. 2005).*
Grant et al. (IEE Proceedings, 1981, vol. 128, Issue 9, pp. 602-606).*
Baziard Y et al. 1988. Dielectric-properties of aluminum powder epoxy-resin composites. *Eur. Polym. J.*, 24:521-526.
Zhao Y et al. 2004. Microwave-Induced Polyol-Process Synthesis of Copper and Copper Oxide Nanocrystals with Controllable Morphology. Eur. J. Inorg. Chem., 4072-4080.
Budde, U., et al., "Draistische Verkurzung von Inkubationszeiten bei Immunhamatologischen Untersuchungen durch Einsatz von Mikrowellengeraten", Infusionsther Transfusionmedizin, 22(suppl. 1):92-94 (Jan. 1, 1995) (abstract).
Elghanian, Robert, et al., "Selective Colorimetric Detection of Polynucleotides Based on the Distance-Dependent Optical Properties of Gold Nanoparticles", Science, 277:1078-1081 (1997).
Hirsch, L.R., et al., "A Whole Blood Immunoassay Using Gold Nanoshells", Anal. Chem., 75:2377-2381 (2003).
Aslan, Kadir, et al., "Microware-Accelerated Surface Plasmon-Coupled Directional Luminescence: Application to fast and sensitive assays in buffer, human serum and whole blood", Journal of Immunological Methods, 323:55-64 (2007).
European Patent Office, Supplementary European Search Report, dated Feb. 4, 2010.
Chan, W. C. W., Maxwell, D. J., Gao, X., Bailey, R. E., Han, M., and Nie, S. 2002 Luminescent quantum dots for multiplexed biological detection and imaging. Curr. Opin. Biotechnol. 13(1):40-46.
Chicoine, L., and Webster, P. 1998. Effect of microwave irradiation on antibody labeling efficiency when applied to ultrathin cryosections through fixed biological material. Micro. Res. Tech. 42(1):24-32.

(Continued)

*Primary Examiner* — Pablo S Whaley
(74) *Attorney, Agent, or Firm* — Marianne Fuierer; Moore & Van Allen, PLLC

(57) ABSTRACT

The present invention relates to systems and methods using microwave accelerated surface plasmonics for the detection of target species. The system has a metallic surface and the system is exposed to microwave energy for increasing detection time and/or the reaction kinetics of the target species and other interacting participants in the system so that plasmonic emissions from the metallic surface alone or coupled with emissions from a luminescing entity are detected.

5 Claims, 34 Drawing Sheets

(56) References Cited

OTHER PUBLICATIONS

Hemmila L. A. 1992. Applications of Fluorescence in Immunoassays, John Wiley and Sons: New York.

Lakowicz, J. R. 1999. Principles of Fluorescence Spectroscopy, Kluwer, New York.

Lövgren, T., and Pettersson, K. 1990. Time-resolved fluoroimmunoassay: advantages and limitations. In Luminescence Immunoassay and Molecular Applications, Van Dyke, K., and Van Dyke, R. (Eds.), CRC Press, Boca Raton, FL, 233-253.

Ozinkas, A. J. 1994. Principles of Fluorescence Immunoassay, In Topics in Fluorescence Spectroscopy, Lakowicz, J. R., Ed., Plenum Press: New York. vol. 4.

Tarkkinen, P., Palenius, T., and Lövgren, T. 2002. Ultrarapid, ultrasensitive one-step kinetic immunoassay for C-reactive protein (CRP) in whole blood samples: Measurement of the entire CRP concentration range with a single sample dilution. Clin. Chem. 48(2):269-277.

Van Dyke, K., and Van Dyke, R., Eds. 1990. Luminescence Immunoassay and Molecular Applications, CRC Press: Boca Raton, FL.

Wilchek, M., and Bayer, E. A. 1990. Methods of Enzymology, vol. 184, Academic Press, San Diego.

Kogan M. J., Bastus N. G., Amigo R., Grillo-Bosch D., Araya E., Turiel A., Labarta A., Giralt E., and Puntes V. F. 2006. Nanoparticle-mediated local and remote manipulation of protein aggregation. *Nano Letters*, 6(1): 110-115. Zhao Y., Zhu J.-J., Hong J.-M., Bian N., and Chen H.-Y. 2004. Microwave-induced polyol process synthesis of copper and copper oxide nanocrystals with controllable morphology. *Eur. J. Inorg. Chem.*, 20: 4072-4080.

Lobmaier, et al. (2001) Direct monitoring of molecular recognition process using fluorescence enhancement at colloid-coated microplates, J. Molecular Recognition, 14: pp. 215-222.

Bauer, et al. 1999 Metal Nano-Cluster Biosensors, Mikrochim Acta, V 131, pp. 107-114.

Geddes, et al, 2003, Metal-Enhance Fluorescence: Potential Applications in HTS, Combination chemistry & HTS, v. 6, pp. 109-117.

Akerman, M. E., Chan, W. C. W., Laakkonen, C., Bhatia, S. N., and Ruoslahti, E. 2002. Nanocrystal targeting in vivo. Proc. Nat. Acad. Sci., 99(20):12617-12621.

Aslan, K., and Geddes, C.D. 2005. Microwave-accelerated metal-enhanced fluorescence: Platform technology for ultrafast and ultrabright assays. Anal. Chem. 77:8057-8067.

Aslan, K., and Geddes, C.D., 2006a. Microwave-accelerated Metal-enhanced Fluorescence (MAMEF): Application to ultra fast and sensitive clinical assays. J. Fluorescence. 16:3-8.

Aslan, K., Malyn, S.N., and Geddes, C.D. 2006b. Fast and sensitive DNA hybridization assays using microwave-accelerated metal-enhanced fluorescence. Biochem. Biophys. Res. Com. 348: 612-617.

Aslan, K., Perez-Luna, V.H, 2002. Surface modification of colloidal gold by chemisorption of alkanethiols in the presence of a nonionic surfactant. Langmuir 18(16): 6059-6065.

Baker, G. A., Pandey, S., and Bright, F. V. 2000. Extending the reach of immunoassays to optically dense specimens by using two-photon excited fluorescence polarization. Anal. Chem. 72(22):5748-5752.

Bange, A., Halsall, H. B., and Heineman, W. R. 2005. Microfluidic immunosensor systems. Biosens. Bioelectron. 20(12):2488-2503.

Borrebaeck, C. A. K. 2000. Antibodies in diagnostics—from immunoassays to protein chips. Immunol Today. 21(8):379-382.

Bruchez, M., Jr., Moronne, M., Gin, P., Weiss, S., and Alivisatos, S. P. 1998. Semiconductor nanocrystals as fluorescent biological labels. Science, 281(5385): 2013-2015.

Chan, W. C. W., and Nie, S. 1998. Quantum dot bioconjugates for ultrasensitive nonisotopic detection. Science, 281(5385):2016-2018.

Chan, W. C. W., Maxwell, D. J., Gao, X., Bailey, R. E., Han, M., and Nie, S. 2002. Luminescent quantum dots for multiplexed biological detection and imaging. Curr. Opin. Biotechnol. 13(1):40-46.

Chicoine, L., and Webster, P. 1998. Effect of microwave irradiation on antibody labeling efficiency when applied to ultrathin cryosections through fixed biological material. Micro Res. Tech. 42(1):24-32.

Choi, S., Choi, E. Y., Kim, D. J., Kim, J. H., Kim, T. S., and Oh, S. W. 2004. A rapid, simple measurement of human albumin in whole blood using a fluorescence immunoassay (I). Clin. Chim Acta. 339 (1-2):147-156.

Dubertret, B., Skourides, P., Norris, D. J., Noireaux, V., Brivanlou, A. H., and Libchaber, A. 2002. In vivo imaging of quantum dots encapsulated in phospholipid micelles. Science, 298(5599):1759-1762.

Gomez-Hens, A., and Aguilar-Caballos, M. P. 2003. Stopped-flow fluorescence polarization immunoassay. Comb. Chem. High Throughput Screen. 6(3):177-182.

Green, N. M. 1975. Adv. Protein Chem. 29: 85-133.

Gryczynski, I., Malicka, J., Jiang, W., Fischer, H., Chan, W. C. W., Gryczynski, Z., Grudzinski, W., and Lakobicz, J. R. 2005. Surface-plasmon-coupled emission of quantum dots. J. Phys. Chem. B. 109(3):1088-1093.

Herron, D.M., Grabowy, R., Connolly, R., and Schwaitzberg, S.D. 1997. The limits of bloodwarming: Maximally heating blood with an inline microwave bloodwarmer. J. Trauma-Injury Infection and Critical Care. 43(2):219-226.

Hirsch, J., Menzebach, A., Welters, I.D., Dietrich, G.V., Katz, N., and Hempelmann, G. 2003. Indicators of erythrocyte damage after microwave warming of packed red blood cells. Clin.Chem., 49(5):792-799.

Kambhampati, D., Nielsen, P. E., and Knoll, W. Investigating the kinetics of DNA-DNA and PNA-DNA interactions using surface plasmon resonance-enhanced fluorescence spectroscopy. Biosens. Bioelectron. 2001, 16 (9-12), 1109-1118.

Lakowicz, J. R. 2004. Radiative decay engineering 3. Surface plasmon-coupled directional emission. Anal. Biochem. 324:153-169.

Liebermann, T., and Knoll, W. 2000a. Surface-plasmon field-enhanced fluorescence spectroscopy. Colloids Surf. 171(1-3):115-130.

Liebermann, T., Knoll, W., Sluka, P., and Hermann, R. 2000b. Complement hybridization from solution to surface-attached probe-oligonucleotides observed by surface-plasmon-field-enhanced fluorescence spectroscopy. Colloids Surf. 169(1-3):337-350.

Lofas, S., Malmqvist, M., Ronnberg, I., Stenberg, E., Liedberg, B., and Lundstrom, I. 1991. Bioanalysis with surface-plasmon resonance. Sensors and Actuators B. 5(1-4):79-84.

Lofas, S., Johnsson, B., J. 1990. A novel hydrogel matrix on gold surfaces in surface-plasmon resonance sensors for fast and efficient covalent immobilization of ligands. J. Chem. Soc.—Chem. Comm. 21:1526-1528.

Micheva, K. D., Holz, R. W., and Smith, S. J. 2001. Regulation of presynaptic phosphatidylinositol 4,5-biphosphate by neuronal activity. J. Cell Biol., 154(2):355-368.

Neumann, T., Johansson, M. L., Kambhampati, D., and Knoll, W. 2002. Surface-plasmon fluorescence spectroscopy. Adv. Funct. Mater., 12(9): 575-585.

Rangell, L. K., and Keller, G. A. 2000. Application of microwave technology to the processing and immunolabeling of plastic-embedded and cryosections. J. Histochem. Cytochem. 48(8):1153-1160.

Rassner, U. A., Crumrine, O. A., Nau, P., and Elias, P. M. 1997. Microwave incubation improves lipolytic enzyme preservation for ultrastructural cytochemistry. Histochem. J. 29(5): 387-392.

Robelek, R., Niu, L., Schmid, E. L., and Knoll, W. 2004. Multiplexed hybridization detection of quantum dot-conjugated DNA sequences using surface plasmon enhanced fluorescence microscopy and spectrometry. Anal. Chem. 76(20): 6160-6165.

Schichnes, D., Nemson, J., Sohlberg, L., and Ruzin, S. E. 1999. Microwave protocols for paraffin microtechnique and in situ localization in plants. Micro Microanalysis 4(5):491-496.

Schray, C. L., Metz, A. L., and Gough, A. W. 2002. Microwave-enhanced fixation for rapid preparation of tissue sections for microscopic evaluation. Histologic. 35(1):7-12.

Schutt, M., Krupka, S. S., Milbradt, A. G., Deindl, S., Sinner, E. K., Oesterhelt, D., Renner, C., and Moroder, L. 2003. Photocontrol of cell adhesion processes: Model studies with cyclic azobenzene-RGD peptides. Chem. Biol., 10(6):487-90.

(56) References Cited

OTHER PUBLICATIONS

Tarkkinen, P., Palenius, T., and Lovgren, T. 2002. Ultrarapid, ultrasensitive one-step kinetic immunoassay for C-reactive protein (CRP) in whole blood samples: Measurement of the entire CRP concentration range with a single sample dilution. Clin. Chem. 48(2):269-277.

Vo-Dinh, T., Sepaniak, M. J., Griffin, G. D., and Alarie, J. P. 1993. Immunosensors: Principles and Applications. Immunomethods, 3:85-92.

von Lode, P., Rainaho, J., and Pettersson, K. 2004. Quantitative, wide-range, 5-minute point-of-care immunoassay for total human chorionic gonadotropin in whole blood. Clin. Chem. 50(6):1026-1035.

Weisbecker, CS., Merritt, M.G., Whitesides, G.M., 1996. Molecular self-assembly of aliphatic thiols on gold colloids. Langmuir 12(16): 3763-3772.

Whittaker, A.G., and Mingos, D.M.P. 1993. Microwave-assisted solid-state reactions involving metal powders and gases. J. Chem. Soc. Dalton Trans. 16:2541-2543.

Kogan M. J., Bantus N. G., Amigo R., Grillo-Bosch D., Araya E., Turiel A., Labarta A., Giralt E., and Puntes V. F. 2006. Nanoparticle-mediated local and remote manipulation of protein aggregation. *Nano Letters*, 6(1): 110-115.

Zhao Y., Zhu J.-J., Hong J.-M., Bian N., and Chen H.-Y. 2004. Microwave-induced polyol process synthesis of copper and copper oxide nanocrystals with controllable morphology. *Eur. J. Inorg. Chem.*, 20: 4072-4080.

Ma Y., Li N., Yang C., and Yang X. 2005. One-step synthesis of amino-dextran-protected gold and silver nanoparticles and its application in biosensors. *Anal. Bioanal. Chem.*, 382:1044-1048.

Zhang J., Geddes C. D., and Lakowicz J. R. 2004. Complexation of polysaccharide and monosaccharide with thiolate boronic acid capped on silver nanoparticle. *Anal. Biochem.*, 332: 253-260.

\* cited by examiner

MICROWAVE-ACCELERATED METAL-ENHANCED DETECTION METHOD

CROSS-REFERENCE TO RELATED APPLICATIONS

The present invention is a Continuation-in-Part application and claims priority of PCT International Application No. PCT/US 2006/000029 filed on Jan. 3, 2006 which in turn claims priority to U.S. Provisional Application No. 60/641,245 filed on Jan. 3, 2005; and further claims priority to U.S. Provisional Patent Application No. 60/788,237 filed on Mar. 31, 2006, and the contents of all priority applications are hereby incorporated by reference herein.

GOVERNMENT RIGHTS IN INVENTION

Work related to the invention was conducted with government support under NIH Grant No. R21 GM 070929-01 and National Center for Research Resources, Grant No. RR008119. As a result of such contracts, the U.S. Government has certain rights in the invention described herein.

BACKGROUND OF THE INVENTION

1. Technical Field

The present invention is directed to a system and method for increasing sensitivity of a detection system, and more particularly, to the use of low power microwaves for speeding up reaction kinetics in plasmonic detection systems that include the use of metallic surfaces including metallic films or nanostructures.

2. Background of Related Art

Over the past 10 years, fluorescence has become a dominant technology in medical testing, drug discovery, biotechnology and cellular imaging. The use of fluorescence technology has greatly enhanced the ability to detect specific molecules, leading to rapid advancements in diagnostics. For example, fluorescence detection is widely used in medical testing and glucose analysis because of the high degree of sensitivity obtained using fluorescent techniques.

For example, surface-based assays, in which the amount of target is quantified by capturing it on a solid support and then labeling it with a detectable label, are especially important since they allow for the facile separation of bound and unbound labels. Often detection of binding complexes in array-based assays involves the detection of a fluorescently labeled species that is part of the binding complex. Optical glucose monitoring is one example of an extremely important and active field of research. The goal of this research is to provide a noninvasive method of monitoring and more optimally managing diabetes, a disease that affects millions of people worldwide. A variety of approaches are currently being pursued, including near- and mid-infrared spectroscopy, photoacoustic spectroscopy, polarimetry, diffuse light scattering, and Raman spectroscopy and plasmonic based sensing systems using surface plasmons.

Surface plasmons are electron oscillations on the surface of metals. However, these plasmons are usually non-radiative and difficult to put to practical use. Recently it has been discovered by the present inventors and colleagues that surface plasmons are easily generated and manipulated using the appropriate metal structures, such as metallic nanostructures of appropriate size and shape.

Metal nanostructures have been studied extensively and are emerging as important colorimetric reporters due to their high extinction coefficients, which are typically several orders of magnitude larger than those of organic dyes. In particular, nanostructures made from the noble metals, such as those of silver or gold, with their associated strong plasmon resonance, have generated great interest.

Notably, the close-proximity of metallic silver islands or colloids can alter the radioactive decay rate and/or excitation rate of fluorophores. Further, it has been shown that quantum yield of low quantum yield fluorophores can be increased by proximity to metallic surfaces. The enhanced excitation of fluorophores in close proximity to metallic surfaces including islands, and colloids can have numerous applications in the biochemical and biological applications of fluorescence because of the increased intensity of the fluorescence.

Fluorescence detection is the basis of most assays used in drug discovery and high throughput screening (HTS) today. In all of these assays, assay rapidity and sensitivity is a primary concern. The sensitivity is determined by both the quantum yield of the fluorophores and efficiency of the detection system, while rapidity is determined by the physical and biophysical parameters of temperature, concentration, assay bioaffinity etc.

However, the assays and system discussed hereinabove are limited by the reaction time of the chemical reactions within the assays, such as that which occur in binding or hybridization. Further even with an increase in reaction time, there still may be reduced emissions from the fluorescencing molecule.

Thus, there is a need for detection systems and methods that increase the biological/biochemical kinetics of the reaction without damaging the participating compounds, increase the sensitivity, increase the intensity of emissions from the detection system and that can be used for in both clinical and emergency room assessments.

SUMMARY OF THE INVENTION

The fact that the plasmon resonance is a sensitive function of nanostructure geometry, coupled with synthetic advances that allow for the controlled and systematic variations in nanostructure geometry, is leading to the expansion of the sensing field called "plasmonics." The present invention improves on the method and systems using plasmonics by increasing the kinetics of the reaction system and coupling plasmonic emissions induced in metallic structure or essentially continuous film type surfaces with those of the luminescing species.

Thus, in one aspect the present invention relates to microwave accelerated surface plasmon-coupled luminescence, where the luminescence from excited fluorophores or luminophores coupled to surface plasmonic emission from metallized particles or surfaces is measured showing an increased intensity of signal and increased reaction time due the introduction of microwave energy to the system.

In another aspect, the present invention relates to a method for shortening the time required for forming an aggregate comprising a metallic nanostructure and a complexing agent having an affinity for at least one group on the metallic nanostructure, the method comprising: applying low power microwaves to the metallic nanostructure and complexing agent to thermally increase heat in the system and/or increase the kinetics of aggregation between the metallic nanostructure and complexing agent. Thus, by using low level microwave heating of the sample greatly speeds up biological/biochemical kinetics in combination with the detection of plasmonic emissions from a metallic surface either alone or in combination with metal-enhanced fluorescence.

The use of low level microwave energy does not destroy or denature biological samples and heats the sample sufficiently to provide for accelerated kinetics such as binding or hybridization. Further, the use of low power microwaves may be used in many different assays, including but not limited to, immunoassays, hybridization assays, resonance energy transfer assays, polarization/anisotropy based assays, luminescence based assays, enzyme-linked immunosorbent assays.

In a further aspect, the present invention relates to increasing the aggregation rate of the metallic nanostructures with non-metallic compounds that are complexed in the aggregation process. Thus, the present invention includes a method for increasing complexing or aggregation of metallic nanostructures comprising dextran immobilized on metallic nanostructures that further comprise thiolate boronic acid attached to at least one of the dextran compounds, the method comprising:

applying low power microwaves to a solution comprising the metallic nanostructures and additional compounds to thermally increase heat in the system and/or increase the complexing of the metallic nanostructures with dextran and subsequent complexing of the dextran with thiolate boronic acid; and detecting plasmonic emissions from the metallic nanostructure.

Detection methods include the detection of plasmonic emissions from a metallic surface either alone or coupled with emissions from the luminescing molecule.

In one embodiment, the metallic nanostructure may comprise dextran immobilized on gold nanoparticles that are combined with concanavalin A (Con A from Canavalia ensiformis), to form the aggregates.

In a further aspect, the present invention relates to a method of increasing sensitivity of a detection or imaging system adapted to detect or image a target in a sample by change in plasmonic resonance of particles in interaction with the target, said method comprising introducing microwaves to said sample that accelerate said interaction.

In yet another aspect the present invention relates to an essentially continuous and planar surface with metallic inclusions for use in a sensing platform technology that detects plasmonic emissions from the surface of the metallic inclusion and/or coupled with emissions from the luminescing molecule positioned near the metallic inclusion. Preferably the sensing platform is combined with the use of microwave energy for increasing detection time and/or the reaction kinetics of fluorescing molecules positioned near the metallic inclusions. Notably, the inclusion of metallic structure in a continuous and essentially planar surface overcomes any unusual scatter patterns of emission from irregular topographies such as curvature due to small metal particles rising above the surface.

Thus, in one aspect, the present invention relates a method for fabricating an essentially continuous and planar surface with metallic inclusions, the method comprising:

providing a surface substrate;

depositing a thin film of a metallic material on the surface substrate:

contacting an adhering and removable material to the thin film of metallic material, wherein the adhering and removable material is patterned to provide at least a section of non contacted metallic material;

removing the adhering and removable material film along with underlying and contacted metallic material thereby leaving a pattern of non-contacted metallic material on the surface substrate; and applying a non metallic material to the surface substrate, wherein the non-metallic material is patterned to expose the non contacted metallic material and wherein the non-metallic material has the ability to absorb electromagnetic energy in the microwave range.

Further, the continuous and planar surface having metallic inclusions may be fabricated by: providing a surface substrate;

depositing a thin film of a metallic material on the surface substrate:

contacting an adhering non-metallic material to the metallic material that is patterned to provide at least a section of non contacted metallic material; wherein the non-metallic material has the ability to absorb electromagnetic energy in the microwave range.

In another aspect, the present invention relates to a system wherein the adhering and removable material is a film with an adhesive side for contacting the metallic material, wherein the film is patterned to expose an area of non contacted metallic material.

In yet another aspect, the present invention relates to an assay system comprising an essentially continuous and planar surface with metallic inclusions, wherein the surface is further modified with coupling agents for binding with target species in a test sample.

In a still further aspect, the present invention relates to a detection method comprising:

providing a metallic surface wherein the metallic surface is modified with coupling agents for binding with target species in a test sample;

introducing a test sample containing at least one target species for binding with the coupling agents, applying electromagnetic energy in the microwave range at low power to cause an increase in heat in the system and/or increase the kinetics of a chemical reaction between the target species and coupling agents occurring within the detection system;

introducing a fluorescing entity or quantum dot having binding affinity for the target species and being positioned near the metallic surface upon binding therewith;

applying an excitation energy to fluorescing entity or quantum dot; and measuring the plasmonic emissions emitted from metallic surface alone or in combination with fluorescence emission of the fluorescing entity or quantum dots.

Preferably, the excitation is generated by any source with the ability to generate multiple photons and more preferably generated by a laser diode, light emitting diode source or pulsing systems thereof. Detection of emitted energy from the fluorescing entity or coupling with plasmonic emission may be accomplished by measuring light emission at discreet angles or polarization of emissions.

The metallic nanostructures may take the form of metallic islands, colloids, or nanostructures of any geometric shape, such as spherical, triangular, elliptical, rod shape, hexagonal or multifaceted. The metallic material may include any form of noble metals such as silver, gold, platinum and copper. Other metallic materials may include aluminum or nickel. Further, continuous surfaces with metallic inclusions may be used as a metallic surface with an essentially planar surface allowing for the use of a planar surface with the applied microwave energy without arcing. The surface substrate that underlies the metallized surface may include both glass and a polymeric material, or combinations thereof.

In yet another aspect, the present invention provides a method for detecting a targeted pathogen in a sample, the method comprising:

providing a system comprising:

a surface comprising an essentially continuous and planar surface with metallic inclusions, wherein the metallic inclusions have attached thereto an immobilized capture nucleotide sequence probe complementary to a known nucleotide sequence of the target pathogen; and contacting the immobilized capture nucleotide sequence probe with a sample suspected of including the nucleotide sequence of the target pathogen, wherein the nucleotide sequence of the target pathogen binds to the immobilized capture nucleotide sequence probe;

irradiating the system with microwave energy in an amount sufficient to enhance binding of the capture nucleotide sequence probe to the nucleotide sequence of the target pathogen and increasing kinetics of the binding reactions;

contacting the bound nucleotide sequence of the target pathogen with a free capture luminescing probe, wherein binding of the free capture luminescing probe causes the luminescing entity to be positioned a sufficient distance from the metallic inclusions to enhance luminescence emission;

irradiating the system with electromagnetic energy in a range from UV to IR to cause luminescence emission by the luminescing entity positioned a predetermined distance from the metallic inclusions; and measuring the plasmonic emissions emitted from the surface of the metallic inclusions alone or in combination with luminescence emission of the luminescing entity.

Preferably, the microwave energy is sufficient to transfer energy to the metallic inclusion thereby causing an increase of heat therein.

Luminescing entities that are capable of luminescing upon excitation by electromagnetic energy emit detectable emissions include, but is not limited to fluorophores, chromophores, luminophores, quantum dots and/or phosphors.

Another aspect relates to a detection method comprising:
applying a conductive metallic material to a surface used in a detection system, wherein the surface includes glass, quartz, or a polymeric material;

applying a receptor molecule to conductive material;

introducing a solution suspected of containing a target ligand having affinity for the receptor molecule, wherein the target ligand upon binding is disposed near the conductive metallic surface;

binding a tag molecule to any bound ligand wherein the tag molecule is capable of fluorescing when excitation is induced and is positioned a distance from the conductive metallic surface to enhance fluorescence;

applying electromagnetic energy in the microwave range to cause an increase in heat in the solution thereby increasing the kinetics of any chemical reactions occurring within the detection system;

exciting the tag with an electromagnetic source to cause fluorescing; and measuring the plasmonic emissions emitted from the surface of the metallic material alone or in combination with fluorescence emission of the fluorescing entity.

Yet another aspect of the present invention, relates to a kit for detecting a target molecule in a sample, the kit comprising a container comprising an essentially continuous and planar surface with metallic inclusions, wherein immobilized probes are connected to the metallic inclusions and wherein the immobilized probe has an affinity for the target molecule;

a fluorophore having an affinity for the target molecule, wherein the binding of the target molecule to both the immobilized probe and fluorophore causes the fluorophore to be positioned a sufficient distance from the metallic inclusions to enhance fluorescence emission;

a source of microwave energy; and a detection device for measuring the plasmonic emissions emitted from the surface of the metallic inclusions alone or in combination with fluorescence emission of the fluorescing entity . . . .

Other features and advantages of the invention will be apparent from the following detailed description, drawings and claims.

DETAILED DESCRIPTION OF THE INVENTION

Figure 1:
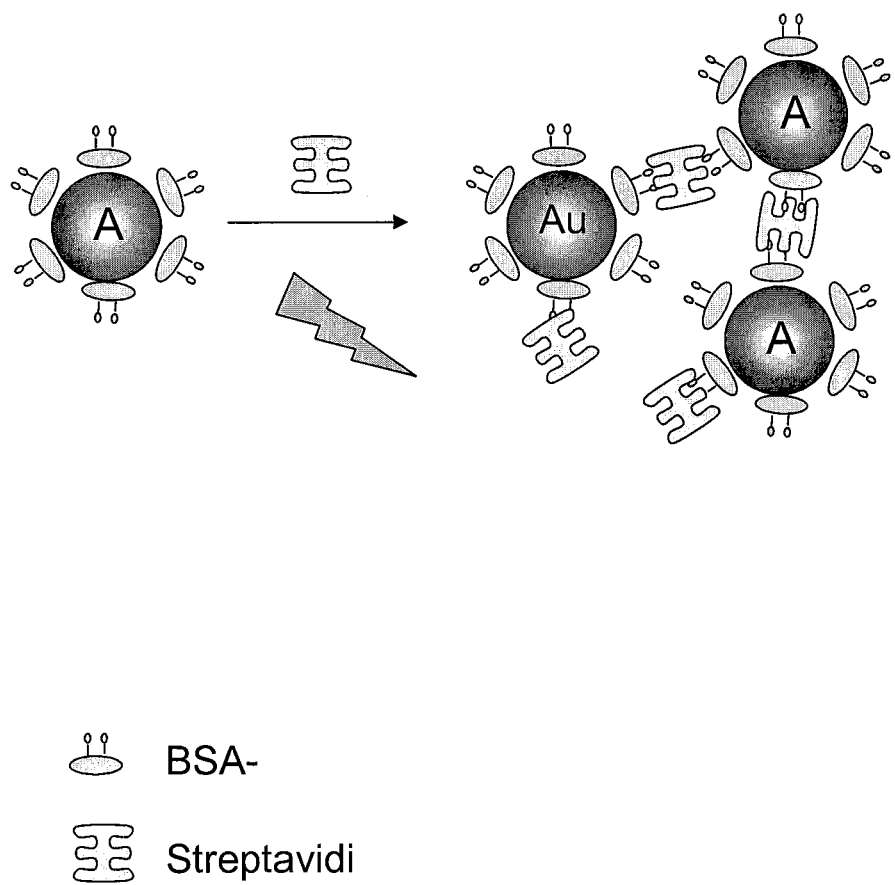
FIG. 1 is a schematic representation of a model protein system demonstrating microwave-accelerated plasmonics, using biotinylated-BSA coated 20 nm gold (Au) colloids cross-linked by streptavidin.

Surface plasmons are collective oscillations of free electrons at metallic surfaces. When a metallic article or surface is exposed to an electromagnetic wave, the electrons in the metal (plasmons) oscillate at the same frequency as the incident wave. Subsequently, the oscillating electrons radiate electromagnetic radiation with the same frequency as the oscillating electrons. It is this re-radiation of light at the same incident wavelength that is often referred to as plasmon emission. In the present invention electromagnetically induced electronic excited states caused by exciting a fluorophore or any luminescence molecule couple to surface plasmons to produce emission intensities greater than from about 5 to 1000-fold, as compared to a control sample containing no metallic surface. This approach is of significance for optically amplifying clinical assays, potentially increasing analyte/biospecies detectability.

The term "biomolecule" means any molecule occurring in nature or a derivative of such a molecule. The biomolecule can be in active or inactive form. "Active form" means the biomolecule is in a form that can perform a biological function. "Inactive form" means the biomolecule must be processed either naturally or synthetically before the biomolecule can perform a biological function. Exemplary biomolecules include nucleic acids, aromatic carbon ring structures, NADH, FAD, amino acids, carbohydrates, steroids, flavins, proteins, DNA, RNA, oligonucleotides, peptide, nucleic acids, fatty acids, myoglobin, sugar groups such as glucose etc., vitamins, cofactors, purines, pyrimidines, formycin, lipids, phytochrome, phytofluor, peptides, lipids, antibodies and phycobiliproptein. Notably, the biomolecule may comprise a fluorescing component that has the ability to fluoresce when contacted with radiation in the range from UV or IR. Preferably, the fluorescing component is a molecule that does not interfere with the chemical reaction of the biomolecule.

The term "receptor-ligand" as used herein means any naturally occurring or unnaturally occurring binding couple wherein the components have affinity for each other. For example, the binding couple may include an antibody/antigen complex, viral coat ligand/protein cell receptor or any combination of probe and binding partner. The term "receptor" refers to a chemical group, molecule, biological agent, naturally occurring or synthetic that has an affinity for a specific chemical group, molecule, virus, probe or any biological agent target in a sample. The choice of a receptor-ligand for use in the present invention will be determined by nature of the disease, condition, or infection to be assayed.

"Fluorophore," as used herein, means any substance that emits electromagnetic energy such as light at a certain wavelength (emission wavelength) when the substance is illuminated by radiation of a different wavelength (excitation wavelength) and is intended to encompass a chemical or biochemical molecule or fragments thereof that is capable of interacting or reacting specifically with an analyte of interest in a sample to provide one or more optical signals. Additionally fluorophore includes both extrinsic and intrinsic fluorophores. Extrinsic fluorophore refer to fluorophores bound to another substance. Intrinsic fluorophores refer to substances that are fluorophores themselves. Exemplary fluorophores include but are not limited to those listed in the Molecular Probes Catalogue which is incorporated by reference herein.

Representative fluorophores include but are not limited to Alexa Fluor® 350, Dansyl Chloride (DNS-Cl), 5-(iodoacetamida)fluoroscein (5-IAF); fluoroscein 5-isothiocyanate (FITC), tetramethylrhodamine 5-(and 6-)isothiocyanate (TRITC), 6-acryloyl-2-dimethylaminonaphthalene (acrylodan), 7-nitrobenzo-2-oxa-1,3,-diazol-4-yl chloride (NBD-Cl), ethidium bromide, Lucifer Yellow, 5-carboxyrhodamine 6G hydrochloride, Lissamine rhodamine B sulfonyl chloride, Texas Red™. sulfonyl chloride, BODIPY™, naphthalamine sulfonic acids including but not limited to 1-anilinonaphthalene-8-sulfonic acid (ANS) and 6-(p-toluidinyl)naphthalene-2-sulfonic acid (TNS), Anthroyl fatty acid, DPH, Parinaric acid, TMA-DPH, Fluorenyl fatty acid, Fluorescein-phosphatidylethanolamine, Texas red-phosphatidylethanolamine, Pyrenyl-phophatidylcholine, Fluorenyl-phosphotidylcholine, Merocyanine 540, 1-(3-sulfonatopropyl)-4-[-.beta.-[2 [(di-n-butylamino)-6 naphthyl]vinyl]pyridinium betaine (Naphtyl Styryl), 3,3'dipropylthiadicarbocyanine (diS-$C_3$-(5)), 4-(p-dipentyl aminostyryl)-1-methylpyridinium (di-5-ASP), Cy-3 Iodo Acetamide, Cy-5-N-Hydroxysuccinimide, Cy-7-Isothiocyanate, rhodamine 800, IR-125, Thiazole Orange, Azure B, Nile Blue, Al Phthalocyanine, Oxaxine 1,4',6-diamidino-2-phenylindole (DAPI), Hoechst 33342, TOTO, Acridine Orange, Ethidium Homodimer, N(ethoxycarbonylmethyl)-6-methoxyquinolinium (MQAE), Fura-2, Calcium Green, Carboxy SNARF-6, BAPTA, coumarin, phytofluors, Coronene, and metal-ligand complexes.

Representative intrinsic fluorophores include but are not limited to organic compounds having aromatic ring structures including but not limited to NADH, FAD, tyrosine, tryptophan, purines, pyrimidines, lipids, fatty acids, nucleic acids, nucleotides, nucleosides, amino acids, proteins, peptides, DNA, RNA, sugars, and vitamins. Additional suitable fluorophores include enzyme-cofactors; lanthanide, green fluorescent protein, yellow fluorescent protein, red fluorescent protein, or mutants and derivates thereof.

Also included are novel quaternary nitrogen heterocyclic boronic acid-containing compounds including:

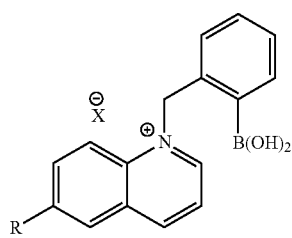

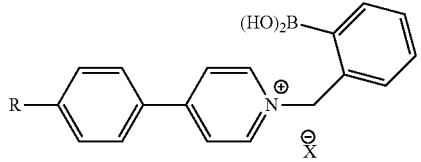
(B)

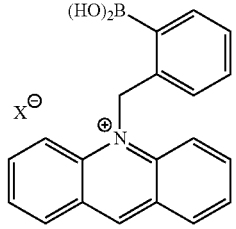
(C)

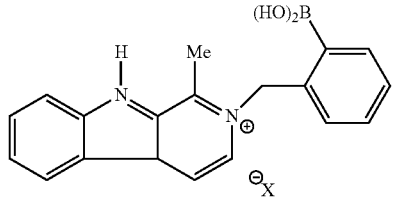
(D)

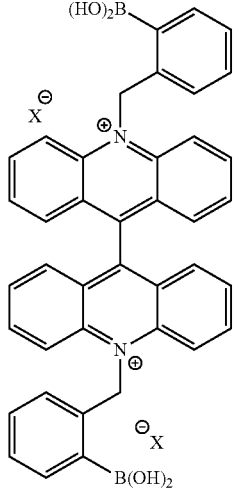
(E)

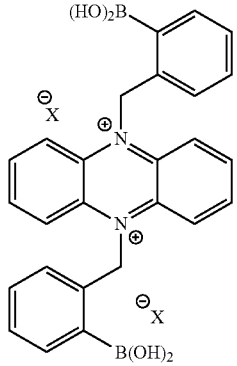
(F)

wherein X is chloride, bromide or iodide and R is selected from the group consisting of H, straight chain or branched $C_1$-$C_4$ alkyl group, $C_1$-$C_4$ alkoxy group, aryl group, hydroxyl, cyano, sulfonyl, and $NR^1R^2$, wherein $R^1$ and $R^2$ may be the same as or different from one another and is independently selected from the group consisting of H and $C_1$-$C_4$ alkyl groups.

Additionally, and alternatively, semiconductor quantum dots (QDs) may be used as an alternative to fluorophores for optical imaging and spectroscopy (Chan, 1998; Dubertret, 2002; Akerman, 2002). QDs are nanometer-sized inorganic structures with physical dimensions smaller than the exciton Bohr radius. QDs exhibit unique luminescence emission characteristics by changing their size or composition. As fluorescent probes, QDs have several advantages over conventional organic fluorophores. Their emission spectra are narrow, symmetrical, and tunable according to their size and material composition, allowing closer spacing of different probes without substantial spectral overlap. Moreover, they exhibit excellent stability against photobleaching. Most significantly, they display broad absorption spectra, making it possible to excite all QDs simultaneously at a single excitation wavelength (Bruchez, 1998; Chan, 2002).

"Nucleotide," as used herein refers to deoxyribonucleic acid (DNA) or ribonucleic (RNA), RNA can be unspliced or spliced mRNA, rRNA, tRNA, or antisense RNAi. DNA can be complementary DNA (cDNA), genomic DNA, or an antisense.

The nucleotides used as hybridization probes in the present invention are typically designed to be specific for the desired sequence in order to decrease the probability of hybridizing to unrelated sequences. Such probes can be modified so as to be detectable using radionuclides, luminescent moieties, and so forth. Hybridization conditions also can be modified in order to achieve the desired specificity. For example, a moderately stringent hybridization condition may include: 2×SSC/0.1% SDS at about 37° C. or 42° C. (hybridization conditions); 0.5×SSC/0.1% SDS at about room temperature (low stringency wash); 0.5×SSC/0.1% SDS at about 42° C. (moderate stringency wash). An example of moderately-high stringency hybridization conditions is as follows: 0.1×SSC/0.1% SDS at about 52° C. (moderately-high stringency wash). An example of high stringency hybridization conditions is as follows: 0.1×SSC/0.1% SDS at about 65° C. (high stringency wash).

The nucleotides sequences of the present invention can be obtained using standard techniques known in the art (e.g., molecular cloning, chemical synthesis) and the purity can be determined by polyacrylamide or agarose gel electrophoresis, sequencing analysis, and the like. Polynucleotides also can be isolated using hybridization or computer-based techniques that are well known in the art. Such techniques include, but are not limited to: (1) hybridization of genomic DNA or cDNA libraries with probes to detect homologous nucleotide sequences; (2) antibody screening of polypeptides expressed by DNA sequences (e.g., using an expression library); (3) polymerase chain reaction (PCR) of genomic DNA or cDNA using primers capable of annealing to a nucleic acid sequence of interest; (4) computer searches of sequence databases for related sequences; and (5) differential screening of a subtracted nucleic acid library.

In one embodiment the present invention relates to microwave-accelerated plasmonics, which utilizes low-level microwaves to markedly enhance the speed of plasmonic changes that are used for detection, thereby dramatically expanding the usefulness of plasmonic detection for a wide spectrum of sensing, monitoring and other applications.

Specific applications of the invention include solutions and assays that employ metal colloids and changes in aggregation of such colloids due to addition of a test sample, e.g., matter containing or suspected of containing an analyte of interest. By introducing low-level microwave energy to the testing system, the aggregative changes occur more rapidly, as compared to a corresponding system in which such microwave energy is not added. Such aggregative changes may involve increases, or alternatively decreases, in aggregation, depending on the specific system involved, and changes in plasmonic absorption and emissions due to changes in the aggregation are readily measured, e.g., to provide output indicative of the presence and/or concentration of a target or agent of interest.

As a consequence of heating by low-level microwaves, changes in aggregation take place in a significantly reduced time-frame, so that the plasmon absorption profile correspondingly undergoes fast change, to facilitate the detection process much more rapidly than has heretofore been possible.

The present invention in various applications employs low power microwaves for heating of samples to greatly speed up biological/chemical kinetics within such samples. Low power microwaves do not destroy or denature proteins, DNA or RNA, but equally heats the sample all over, providing for accelerated kinetics in applications such as binding or hybridization.

In practice any microwave energy source may be used. Preferably, the source is a magnetron generating microwave energy that is transported as an electromagnetic wave in a frequency range between about $10^8$ to about $10^{12}$. A feed structure may be included that guides the microwaves from the energy source to a containment chamber containing the detection assay or system. Electronic controls are usefully employed to control the microwave energy source and the power of said energy. Preferably, the power is maintained between about 0.0001 µW/cm$^2$ to about 1000 µw/cm$^2$ and more preferably from about 0.0001 µW/cm$^2$ to about 0.01 uW/cm$^2$.

The invention combines the use of metal-enhanced fluorescence with the ability to greatly speed up biological/biochemical kinetics by using low level microwave heating of the samples. Low level microwaves do not destroy or denature proteins, DNA, or RNA, but instead heat the sample sufficiently to provide for accelerated kinetics such as chemical reactions involved in binding or hybridization or mechanical increases in solution fluid dynamics to move reactants together at an increased speed. In addition, the microwaves are not scattered by the continuous films of the present invention, which is contrary to most metal objects such as that recognized by placing a spoon in a microwave oven. Hence, the present invention combines the enhanced and localized signal intensities that have been reported for metals in close proximity to fluorophores with the ability to rapidly heat the samples using low level microwaves.

Microwaves (about 0.3 to about 300 GHz) lie between the infrared and radiofrequency electromagnetic radiations. It is widely thought that microwaves accelerate chemical and biochemical reactions by the heating effect, where the heating essentially follows the principle of microwave dielectric loss. Polar molecules absorb microwave radiation through dipole rotations and hence are heated, where as non-polar molecules do not absorb due to lower dielectric constants are thus not heated. The polar molecules align themselves with the external applied field. In the conventional microwave oven cavity employed in this work, the radiation frequency (2450 MHz) changes sign 2.45×10$^9$ times per second. Heating occurs due to the tortional effect as the polar molecules rotate back and forth, continually realigning with the changing field, the molecular rotations being slower than the changing electric field. The dielectric constant, the ability of a molecule to be polarized by an electric field, indicates the capacity of the medium to be microwave heated. Thus, solvents such as water, methanol and dimethyl formamide are easily heated, where as microwaves are effectively transparent to hexane, toluene and diethylether.

For metals, the attenuation of microwave radiation arises from the creation of currents resulting from charge carriers being displaced by the electric field. These conductance electrons are extremely mobile and unlike water molecules can be completely polarized in 10-18 s. Interestingly, and most appropriate for the new assay platform described herein, small metal particles do not generate sufficiently large potential differences for this "arcing" phenomenon to occur. However, as discuss hereinbelow, the charge carriers which are displaced by the electric field are subject to resistance in the medium in which they travel due to collisions with the lattice phonons. This leads to Ohmic heating of the metal nanoparticles in addition to the heating of any surface polar molecules. Intuitively, this leads to localized heating around the silver nanostructures in addition to the solvent, rapidly accelerating assay kinetics. Further, the close proximity of assay fluorophores, additionally leads to fluorophore radiative decay rate modifications and the subsequent increase in fluorescence emission. Hence metallic inclusions, fluorophores and microwaves can be combined to yield kinetically accelerated and optically amplified immunoassays.

There are many important assays that can directly benefit from enhanced signal intensities and quicker kinetics. For example, myoglobin concentrations for heart attack patients, patients of toxic shock and pancreatitus. All of these assays are widely used in hospitals emergency rooms with assay times of greater than 30 minutes. Thus, the present invention can be used for points—of—care clinical assessment in emergency rooms.

In the present invention, microwave radiation is provided by an electromagnetic source having a frequency in a range between 0.3 and 10 GHz and a power level in a range between about 10 mwatts and 400 watts, more preferably from 30 mwatts to about 200 watts. Any source, known to one skilled in the art may be used, such as a laser that emits light, wherein light is used in its broad sense, meaning electromagnetic radiation which propagates through space and includes not only visible light, but also infrared, ultraviolet and microwave radiation. Thus, a single instrument placed above or below the surface of the assay can be used to generate the microwave energy and energy to excite fluorescing molecules. The energy can be emitted from a fiber continuously or intermittently, as desired, to maintain the metallic particles at a predetermined temperature such that it is capable of increasing the speed of chemical reactions within the assay system. In the alternative, microwave energy can be supplied through a hollow wave guide for conveying microwave energy from a suitable magnetron. The microwave energy is preferably adjusted to cause an increase of heat within the metallic material without causing damage to any biological materials in the assay system.

A typical electromagnetic processing system operating at microwave frequencies includes several related components: (1) an energy source, usually a constant frequency microwave oscillator, (2) transmission lines, e.g., a waveguide or coaxial cable, (3) an applicator and containment chamber, and (4) the process material itself. The containment chamber preferably is formed of microwave reflective material and is designed to prevent leakage of microwave energy to the environment outside the containment chamber.

Additionally, maser technology may be used in the practice of the present invention. Masers are devices that amplify or generate electromagnetic energy waves with great stability and accuracy. Masers operate on the same principal as lasers, but produce electromagnetic energy in the radio and microwave, rather than visible range of the spectrum. In masers, the electromagnetic energy is produced by the transition of molecules between rotational energy levels.

In one embodiment of the invention, low-power microwave energy is used in the synthesis of dextran-coated gold colloids and subsequent aggregation with the addition of Con A, thereby providing for useful sensing aggregates, which show plasmon changes in the presence of glucose which is widely known to competitively bind Con A. Further, by altering the gold colloid size, the dextran molecular weight and the concentration of Con A used to form the sensing aggregate, dynamic glucose sensing range can be fine-tuned. The dextran-coated gold colloids, which have been aggregated by the controlled addition of Con A can be synthesized with enhancement of the synthesizing regime by applying low power microwaves to increase the kinetics of chemical reactions in the aggregation process.

The plasmon resonance particles utilized in the plasmonics detection method of the invention can be formed of any suitable material, such as for example gold, copper, silver, aluminum, and alloys including one or more of such metals. The plasmon resonance particles can for example be used to sense analytes, e.g., in clinical, industrial or environmental applications. As another example, such plasmon resonance particles can be employed for imaging applications, such as in the detection of cancers, genomic abnormalities etc.

In use, the plasmon resonance particles can be used for sensing in different ways, such as for example colorimetrically, by changes in their absorption based properties, in exposure to light, and/or by changes in scattering properties of the plasmon resonance particles, in exposure to white light or monochromatic/laser light.

The plasmon resonance particles can change these properties in response to their close proximity, a function of particle aggregation, since the plasmon resonances will interact at distances of approximately 2.5 times the diameter of the plasmon resonance particles. The plasmon resonance particles also exhibit changed properties in response to long range coupling at distances of 2.5 times their radius, so that large colloids can be used to couple over larger distances. The plasmon resonance particles also change properties in response to changes in local particle refractive index.

Although plasmon absorption and plasmon light scattering have been used in assays for detection, imaging and biosensing, no one has considered accelerating plasmonic kinetics using low power microwaves and or coupling such plasmonic emissions with emissions from excited tag molecules that fluoresces or luminesce.

The present invention therefore achieves a major advance in the art, and enables new detection, assay and imaging products, including, without limitation: microwave-accelerated plasmon absorption based detection for drug screening; plasmonic scattering assays; plasmon scattering based imaging, e.g., in cancer expression and determination applications; rapid" detection of DNA targets, for clinical or bioterrorism-related applications; rapid detection of RNA targets, such as for rapid avian bird flu detection; and rapid detection of protein-based targets for clinical, pharmaceutical and research applications.

The microwave-accelerated plasmonics process of the invention is usefully employed to facilitate the rapid detection of any analyte that causes a change in either the plasmon resonance absorption band (colorimetrically) or by rapid changes in the light scattering properties of the particles. The invention reflects the surprising and unexpected finding that low power microwaves do not perturb plasmon resonances of metallic nanostructures, a discovery that is at odds with the conventional experience of metallic structures being incompatible with microwave exposure. It is common experience that metallic structures in microwave cavities typically cause arcing or sparking, such as when a teaspoon is inadvertently left in a microwave oven that is subsequently turned on.

For metals, attenuation of microwave radiation arises from the creation of currents resulting from charge carriers being displaced by the electric field. These conductance electrons are extremely mobile and unlike water molecules can be completely polarized in 10 to 18 s. In microwave cavities employed in the practice of the invention, the time required for the applied electric field to be reversed is far longer than this, in fact many orders of magnitude. If metal particles are large, or form continuous strips, then large potential differences can result, which can produce dramatic discharges if they are large enough to break down the electric resistance of the medium separating such large metal particles.

Interestingly, the small metal particles do not generate sufficiently large potential differences for such arcing and sparking phenomena to occur, but the charge carriers that are displaced by the electric field are subject to resistance in the medium in which they travel due to collisions with the lattice phonons. This in turn leads to ohmic heating of the small metal particles in addition to the heating of any surface polar molecules, e.g., in an associated solvent medium. Thus, assays and other detection applications are enabled, in which such localized heating rapidly accelerates the kinetics of the assay or other detection process.

The present invention in another aspect contemplates a plasmonic resonance detection or imaging system arranged for detecting or imaging a target in a sample by change in plasmonic resonance of particles in interaction with the target, in which the system includes a microwave source arranged to introduce microwaves to the sample that accelerate such interaction. The microwave source in such system can comprise a constant frequency microwave oscillator, and a waveguide adapted to transmit microwaves from the oscillator to the sample.

The emission enhancement may be observed at distances according to the type of luminescence or fluorescence species to be detected and the type of metal. For example, emission enhancement may be observed when a luminescence or fluorescence species is positioned about 5 nm to about 200 nm to metal surfaces. Preferable distances are about 5 nm to about 30 nm, and more preferably, 5 nm to about 20 nm to metal surfaces. At this scale, there are few phenomena that provide opportunities for new levels of sensing, manipulation, and control. In addition, devices at this scale may lead to dramatically enhanced performance, sensitivity, and reliability with dramatically decreased size, weight, and therefore cost. The silver islands have the remarkable effect of increasing the emission intensity at least 5-fold while decreasing the lifetime 100-fold.

Light from the fluorescence or luminescence species generated by the random depopulation of a chemically induced electronic state of a fluorophore or luminophore and/or the plasmon coupled emissions from the metallic components can be detected using an optical detector, positioned above and/or below reaction sites. Various optical detectors, such as photodiode, charge-coupled device (CCD), photomultiplier tube (PMT), or photon counting detector, have different degree of sensitivity. PMT and photon counting detectors can achieve an electronic amplification factor as high as $10^6$-$10^8$. Conventional PMTs require a ~1 kV power source, but new miniaturized detector requires only a 5 V. Most of fluorescence or luminescence emission wavelengths are in the visible region. A narrow-band optical filter may be used to ensure detecting luminescence wavelengths. The system may include a microactuator, detector, microprocessor, electronics, a display, and translation stage. The output of the detector may be interfaced to an analog to digital converter and a microprocessor to calculate analyte concentration.

In another embodiment, the present invention relates to luminescence detection systems and methods used for detecting species of interest in close proximity to a continuous film, wherein the continuous film includes metallic inclusion thereby allowing coupling of surface plasmon emissions with emissions of luminescent species. The luminescence detection systems of the present invention are further enhanced by the use of microwaves to accelerate both chemical and mechanic kinetics within the systems.

The present invention provides enhanced emissions using metallized islands of elliptical, spherical, triangular or rod-like forms. In exemplary cases, the elliptical islands have aspect ratios of 3/2, and the spherical colloids have diameters of 20-60 nm. However, the invention is not limited to any particular geometry. Using known coating techniques, the placement of metallic islands could be controlled precisely, as close as 50 nm apart. In the continuous metallic film case, the fluorophore emissions could be detected in the analyte solution up to 500 nm away from the surface of the metal. In the case where the metallic coating is formed by islands, the enhanced fluorophore emissions could be detected in the solution up to 200 nm away from the surface of the metal.

In yet another embodiment the present invention provides for metallic material and a fluorophore or luminophore capable of emitting induced electromagnetically energy in the visible range, wherein the metallic material and the fluorophore or luminophore are separated by at least one film spacer layer. The thickness of said film may be chosen so as to enhance the fluorescence of the fluorophore due to the distance of the fluorophore from the metallic material. The film spacer layer may be one or multiple layers of a polymer film, a layer formed from a fatty acid or a layer formed from an oxide, such as silicon dioxide ($SiO_2$). In a preferable embodiment, the film spacer layers and the metallic material are chemically inert and do not bind to the fluorophore to be detected or to intermediates that are bound to the compounds to be detected, for example covalently bound. The layer formed from a fatty acid may be formed by a Langmuir-Blodgett technique. The film spacer layer may be a spin coated polymer film. The oxide layer may be formed from a deposition technique, such as vapor deposition.

It is known that a nearby metal can increase the intrinsic decay rate of a fluorophore, that is, to modify the rate at which the fluorophore emits photons. In fluorescence, the spectral observables are governed by the magnitude of λ, the radiative rate, relative to the sum of the non-radiative decay rates, $k_{nr}$, such as internal conversion and quenching.

Fluorophores with high radiative rates have high quantum yields and short lifetimes. Increasing the quantum yield requires decreasing the non-radiative rates $k_{nr}$, which is often only accomplished when using a low solution temperature or a fluorophore bound in a more rigid environment. The natural lifetime of a fluorophore, $\tau_n$, is the inverse of the radiative decay rate or the lifetime which would be observed if their quantum yields were unity. This value is determined by the oscillator strength (extinction coefficient) of the electronic transition. Hence, for almost all examples currently employed in fluorescence spectroscopy, the radiative decay rate is essentially constant. The modification and control of the radiative rate have also been referred as Radiative Decay Engineering (RDE), or "lightening rod" fluorescence enhancement effect. For example, enhanced intrinsic DNA fluorescence above metallic particles has recently been observed, which is typically not readily observable because of DNA's very low quantum yield of less than $10^{-4}$. The second favorable "lightening rod" effect also increases the fluorescence intensity by locally enhanced excitation. In this case, emission of fluorophores can be substantially enhanced irrespective of their quantum yields.

The reduction in lifetime of a fluorophore near a metal is due to an interaction between the fluorophore and metal particle, which enhances the radiative decay rate (quantum yield increase) or depending on distance, $d^{-3}$, causes quenching. It should be noted that lifetimes of fluorophores with high quantum yields (0.5) would decrease substantially more than the lifetimes of those with low quantum yields (0.1 and 0.01). A shorter excited-state lifetime also allows less photochemical reactions, which subsequently results in an increased fluorophore photostability. Notably, the use of low quantum yield fluorophores would lead to much larger fluorescence enhancements (i.e. $1/Q_0$) and could significantly reduce unwanted background emission from fluorophores distal from the silvered assay.

Fluorophore photostability is a primary concern in many applications of fluorescence. This is particularly true in single molecule spectroscopy. A shorter lifetime also allows for a larger photon flux. The maximum number of photons that are emitted each second by a fluorophore is roughly limited by the lifetime of its excited state. For example, a 10 ns lifetime can yield about $10^8$ photons per second per molecule, but in practice, only $10^3$ photons can be readily observed. The small number of observed photons is typically due to both photo-destruction and isotropic emission. If a metal surface decreases the lifetime, one can obtain more photons per second per molecule by appropriately increasing the incident intensity.

On the other hand, the metal-enhanced fluorescence provides enhanced intensity, while simultaneously shortening the lifetime. That is, it may be possible to decrease the excitation intensity, yet still see a significant increase in the emission intensity and photostability.

The emission enhancement may be observed at distances according to the type of fluorophore to be detected and the type of metal. For example, emission enhancement may be observed when a fluorophore distances about 4 nm to about 200 nm to metal surfaces. Preferable distances are about 4 nm to about 30 nm, and more preferably, 4 nm to about 20 nm to metal surfaces. At this scale, there are few phenomena that provide opportunities for new levels of sensing, manipulation, and control. In addition, devices at this scale may lead to dramatically enhanced performance, sensitivity, and reliability with dramatically decreased size, weight, and therefore cost. The enhancement of fluorescence is, in part due to the localized excitation of the fluorophores when in close proximity to the silver nanoparticles and results in improved photostability of the fluorophores. When the metal (silver, aluminum or gold) is a continuous 45 nm-thick film, the spatially isotropic fluorescence emission can be converted into directional emission towards a detector further improving the detectability.

The enhancement of fluorescence is, in part due to the localized excitation of the fluorophores when in close proximity to the silver nanoparticles and results in improved photostability of the fluorophores. When the metal (silver, aluminum or gold) is a continuous 45 nm-thick film, the spatially isotropic fluorescence emission can be converted into directional emission towards a detector further improving the detectability.

Fluorescence can be detected using devices including, but not limited to, a spectrofluorometer having a light source and detector. Additional detectors may include GaAs-cathode PMT. Further, detectors can include photomultiplier tubes. Additionally, it is advantageous for the device to have a monochromator so that specific wavelengths of light may be used to excite a molecule or to detect emissions at a specific wavelength.

Excitation light sources can include arc lamps and lasers, laser diodes and light emitting diode source, and both single and multiple photon excitation sources. In another embodiment, use of a Ti-sapphire laser, Laser Diode (LD) or Light Emitting Diode Sources (LEDs) may be used with the RNA assay of the present invention. For example, using 2-photon excitation at 700-1000 nm and also using short pulse width (<50 pi), high repetition rate (1-80 MHz), laser diode and LED (1 ns, 1-10 MHz) sources. The enhanced sensitivity of the assay using 2-photon excitation, as compared to 1-photon, can be shown by using series dilution with RNA, initially with the Ti-Sapphire system, and later with LEDs and LDs. If a fluorophore absorbs two photons simultaneously, it will absorb enough energy to be raised to an excited state. The fluorophore will then emit a single photon with a wavelength that depends on the fluorophore used and typically in the visible spectra. The use of the Ti-sapphire laser with infrared light has an added benefit, that being, longer wavelengths are scattered less, which is a benefit to high-resolution imaging. Importantly, there is reduced background signal level gained by using 2-photon excitation as compared to 1-photon excitation by utilizing localized excitation near by a metallic particles.

Preparation of Metal Surface

The metallic surface is prepared in clean beakers by reduction of metal ions using various reducing agents. For example, sodium hydroxide is added to a rapidly stirred silver nitrate solution forming a brown precipitate. Ammonium hydroxide is added to re-dissolve the precipitate. The solution is cooled and dried quartz slides are added to the beaker, followed by glucose. After stirring for 2 minutes, the mixture is warmed to 30° C. After 10-15 minutes, the mixture turns yellow-green and becomes cloudy. A thin film of silver particles has formed on the slides as can be seen from their brown green color. The slides are rinsed with pure water prior to use.

Positioning of the metal particle at a desired distance can be achieved by using a film. The film may be a polymer film, a Langmuir-Blodgett film or an oxide film. Metal-fluorophore distances may be achieved by using Langmuir-Blodgett films with fatty acid spacers. The fatty acids may be from natural sources, including concentrated cuts or fractionations, or synthetic alkyl carboxylic acids. Examples of the fatty acids include, but not limited to, caprylic ($C_8$), capric ($C_{10}$), lauric ($C_{12}$), myristic ($C_{14}$), palmitic ($C_{16}$), stearic ($C_{18}$), oleic ($C_{18}$), linoleic ($C_{18}$), linolenic ($C_{18}$), ricinoleic ($C_{18}$) arachidic ($C_{20}$), gadolic ($C_{20}$), behenic (C22) and erucic ($C_{22}$). The fatty acids with even numbered carbon chain lengths are given as illustrative though the odd numbered fatty acids can also be used.

Metal-fluorophore distances may be achieved by using polymer films. Examples of the polymer include, but not limited to, polyvinyl alcohol (PVA). Absorbance measurements and ellipsometry may be used to determine polymer film thickness. One type of polymer films is spin coated polymer film. The technology of spin coated polymer spacer films readily allows films to be coated onto a variety of surfaces, with varied thickness from >0.1 um. The coating can be performed on a spin coater, which allows uniform surface thickness by varying polymer concentration (viscosity) and spin speed. For example, Model P6700 spin coater (Specialty Coating Systems Inc.), allows uniform surface thickness by varying polymer concentration (viscosity) and spin speed.

Colloids can be prepared as suspensions by citrate reduction metals. Preferred metals are silver and gold. Again, gold may be used because of the absorption of gold at shorter wavelengths. The size of the colloids and their homogeneity can be determined by the extensive publications on the optical properties of metal particles available and the effects of interface chemistry on the optical property of colloids.

Metal particles can be bound to a surface by placing functional chemical groups such as cyanide (CN), amine ($NH_2$) or thiol (SH), on a glass or polymer substrate. Metal colloids are known to spontaneously bind to such surfaces with high affinity.

Notably, the metallic material may be in the form of a porous three dimensional matrix. The three dimensional matrix may be a nano-porous three dimensional matrix. The metallic material may include metal colloid particles and/or metal-silica composite particles. The metallic material may comprise agglomerated metal particles and/or binary linked particles or metal particles in a polymer matrix. The three dimensional matrix may be formed from controlled pore glasses or using matrices assembled from the aggregation of silver-silica composites themselves. The matrices may be metallic nanoporous matrix, through which species will flow and be both detected and counted more efficiently.

Detectors can include photomultiplier tubes. The polarized-scattering from metallic surfaces can be measured using an X-Y rotating stage (Edmund Optics), with a fiber optic mount. The metallic structures can be illuminated with vertically polarized laser sources with a neutral density filter being used to adjust the laser intensity. The angle-dependent vertically polarized scattered light from the metallic surfaces can be collected through a dichroic sheet polarizer (Edmund optics) into a 600 micron broad wavelength fiber that was connected to an Ocean Optics HD2000 spectrofluorometer. The photostability aggregation of metallic surfaces can be measured by simply observing the polarized scattered intensity at different angles, such as 90 or 140 degrees for a specific length of time, such as 30 or 45 minutes.

Notably, the present invention provides for the application of plasmon scatter and the measurement of distances in the range 10-300 nm for biological systems. Today, optical distance measurements less than 10 nm are undertaken using FRET between a fluorescent donor and an acceptor. Distances ranging from macroscopic to about $\lambda/2$, typically about 300 nm, can be measured using confocal, multiphoton and/or laser scanning methods but these systems are not readily compatible with biological species, such as live cells. This approach may be of significant importance for studying macromolecular dynamics and particularly in immunoassays, which typically have dimensions far too large for classical FRET. Additionally, it is advantageous for the device to have a monochromator so that specific wavelengths of light may be used to excite a molecule or to detect emissions at a specific wavelength

EXAMPLES

The features and advantages of the invention are more fully shown in reference to the following non-limiting illustrative examples.

Example 1

Materials

Gold nanoparticle dispersions (monodisperse, either 20 or 10 nm average particle diameter), concanavalin A (Con A from Canavalia ensiformis), dextran (average molecular weight: 64000 and 505000) hydrogen peroxide, sulfuric acid, sodium phosphate monobasic, phosphate-buffered saline (PBS), absolute ethanol, 2-(2-aminoethoxy)ethanol (AEE) and N-hydroxy-2,5-pyrrolidinedione (NHS) were obtained from Sigma. 16-Mercaptohexadecanoic acid (16-MHDA) and polyoxyethylene (20) sorbitan monolaurate (Tween 20), epichlorohydrin, 2-methoxyethyl ether (diglyme), and nitric acid were obtained from Aldrich. N-3-(Dimethylaminopropyl)-N'-ethyl-carbodiimide (EDC) was obtained from Fluka. All chemicals were used as received. Buffers and solutions.

Sodium phosphate monobasic buffer solution was prepared to a 10 mM concentration at pH 7. PBS was dissolved in deionized water and the pH was adjusted to 7.4. Exact pH values for buffer solutions were obtained using a Beckman pH meter. Deionized water (>18 MΩ/cm) was used in the preparation of all buffer solutions. All glassware was washed with "piranha solution" (3:7, 30% $H_2O_2/H_2SO_4$) prior to use. Solutions of 0.50 mM 16-MHDA were prepared in degassed ethanol. Tween 20 solutions were prepared in sodium phosphate buffer at pH 7.

Surface modification of the gold colloids: preparation of the glucose aggregate nanosensors.

The immobilization of dextran on gold nanoparticles was performed using the following four steps: (A) chemisorption of a long-chain carboxyl-terminated alkane thiol on gold nanoparticles as described previously [1]; (B) the activation of surface carboxyl groups using EDC and NHS; (C) activation of hydroxyl groups using epicholorohydrin; and (D) the covalent coupling of dextran.

Gold nanoparticle dispersions with a concentration of 0.80 nM for 20 nm, and 8 nM for 10 nm gold colloids (determined by measuring absorbance at 520 nm and using extinction coefficients of $1.25 \times 10^9$ and $1.21 \times 108$ $M^{-1}$ $Cm^{-1}$ for 20 and 10 nm gold, respectively; Sigma) were degassed with nitrogen before use. The gold colloids are not naked, but indeed solution stabilized with the citrate counter ion. The addition of the alkane thiol (step 1) replaces the citrate counter ion, producing a stabilized mono layered protected particle (Aslan 2002). Equal volumes (400 MI) of gold nanoparticle dispersions (0.80/8 nM, before mixing) and Tween 20 (1.82 mg/ml, before mixing) in pH 7 buffer were gently mixed and allowed to stand for 30 min for the physisorption of the Tween 20 to the gold nanoparticles. Four hundred microliters of 0.50 mM 16-MHDA was then added and the final mixture (final concentrations: [gold nanoparticles]=0.27/2.67 nM; [Tween 20]=0.61 mg/ml; [16-MHDA]=0.17 mM) was allowed to stand for 3 h for the chemisorption of 16-MHDA to be completed on the gold colloids, while simultaneously displacing Tween 20 (Asian 2002). The time requirement for chemisorption of both the Tween and subsequent displacement with MHDA can be reduced by using low-power microwave energy.

In order to remove excess 16-MHDA and Tween 20, the final mixture was centrifuged (three times for 15 min at 16 060*g; the supernatants were discarded after each cycle) and resuspended in phosphate buffer (with 1.82 mg/ml Tween 20 at pH 7). 16-MHDA-modified gold colloids that remained in the centrifugate were then reacted with a mixture of freshly prepared 50 mM NHS and 200 mM EDC solution (in phosphate buffer without Tween 20) for 5 min. The resulting nanoparticle dispersion was centrifuged (5 min, 16 060×g) and after discarding the supernatant, the remaining NHS ester-alkane thiol-modified gold nanoparticles were reacted with a freshly prepared solution of AEE (2%, v/v) for 10 min. Excess AEE was removed by centrifugation (for 5 min at 16 060×g at least three times). The retentate that contained AEE-modified gold nanoparticles was centrifuged (5 min, 16 060× g). The hydroxyl groups on the AEE-modified gold nanoparticles were activated with 0.6 M epicholorohydrin solution in a 1:1 mixture of 0.4 M NaOH and diglyme for 4 h at room temperature. The nanoparticle dispersion was then centrifuged for 10 min at 16 060×g and resuspended in diglyme and centrifuged again to remove the excess epicholorohydrin. The centrifugate, containing AEE-modified gold nanoparticles with active epoxide groups, were incubated in dextran solution (0.1 M NaOH) for 20 h (Lofas 1990). Again, the time requirement for attachment of dextran to the AEE-modified gold nanoparticles can be reduced by using low-power microwave energy.

Finally, dextran-modified gold nanoparticles were centrifuged for 15 min at 16 060×g and resuspended in 0.1 M NaOH and centrifuged four more times to remove the excess dextran. All solutions of dextran-coated gold nanoparticles were stored in polypropylene centrifuge tubes in the dark to prevent light-induced flocculation of the nanoparticles and oxidation of the alkane thiols (Weisbecker 1996).

To monitor the extent of aggregation, which clearly showed a significant change in absorbance, $\Delta A_{650}$, between a highly aggregated system and a slightly aggregated system. The time required to complete aggregation for the same set of samples was additionally investigated by monitoring the $\Delta A_{650}$ as a function of time. As expected, samples with greater additions of Con A showed shorter 90% absorbance (of the final absorbance maximum value) change times, simply reflecting a quicker aggregation rate. Aggregation time can be reduced by applying low-power microwave energy thereby providing usable nanoparticles in a shorter time-period without damaging any of the components.

Example 2

This example illustrates a microwave accelerated plasmonics application in which low power microwaves are utilized in solution based plasmon resonance particle assays.

As a model protein based system, biotinylated-bovine serum albumin coated 20 nm gold particles, crosslinked by additions of streptavidin (a tetravalent protein), are employed. The model system is schematically shown in FIG. 1, in an illustrative depiction of the gold particles (Au) coated with BSA-biotin, undergoing aggregation in the presence of streptavidin and low level microwave energy input.

Figure 2:
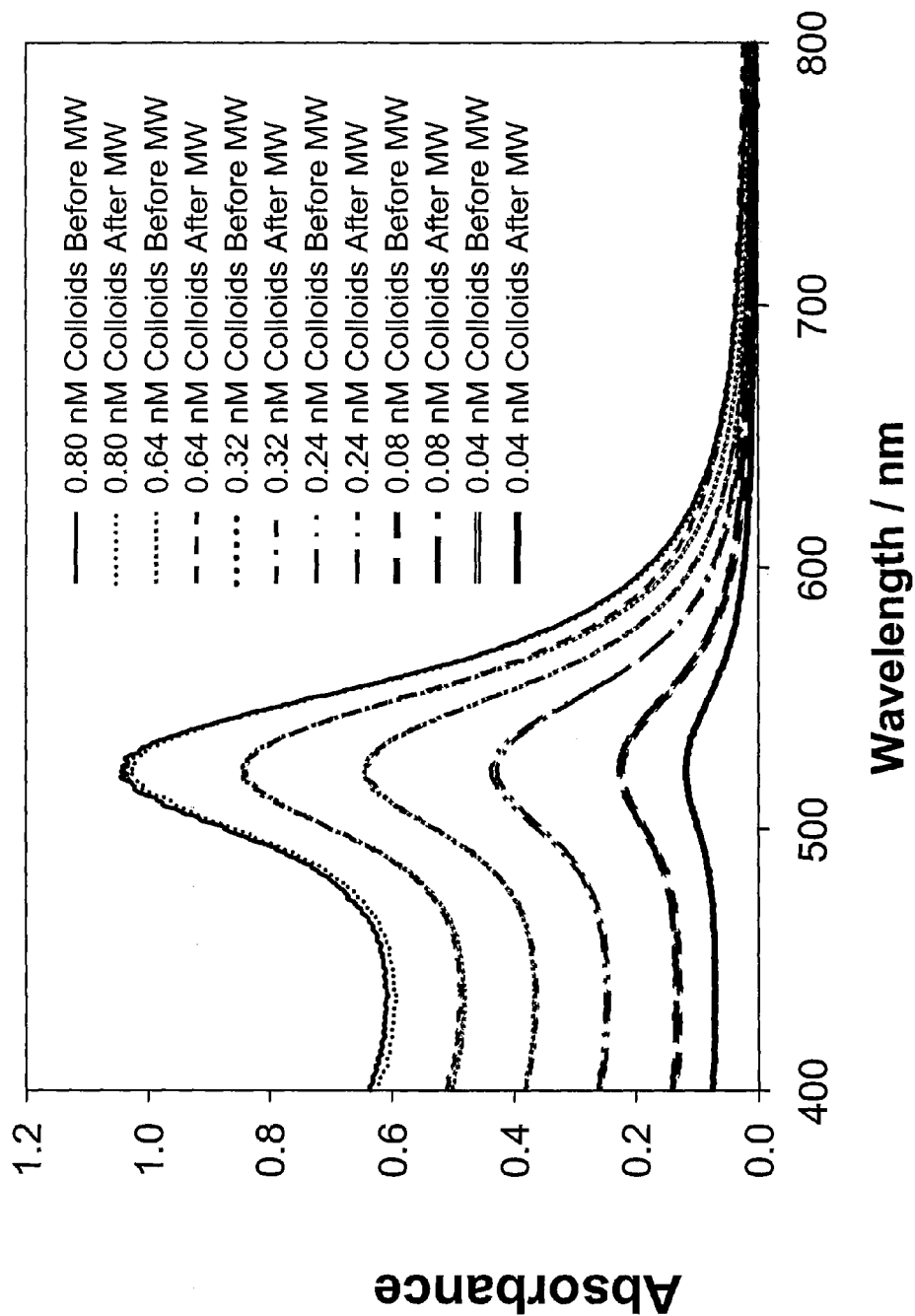
FIG. 2 shows absorption spectra of 20 nm gold colloids as a function of concentration, before and after exposure to low power microwaves.

FIG. 2 shows absorption spectra of 20 nm gold colloids as a function of concentration, before and after exposure to low power microwaves. In FIG. 2, a range of different concentrations of 20 nm gold colloids (0.80 nM; 0.64 nM; 0.32 nM; 0.24 nM; 0.08 nM; and 0.04 nM) can be seen. The plasmon resonances are not perturbed by the low power heating, as shown by the close congruence of the respective curves before and after microwave (MW) exposure, at each of the concentrations over the range, evidencing the surprising and unexpected character of the discovery of the present invention.

Figure 3:
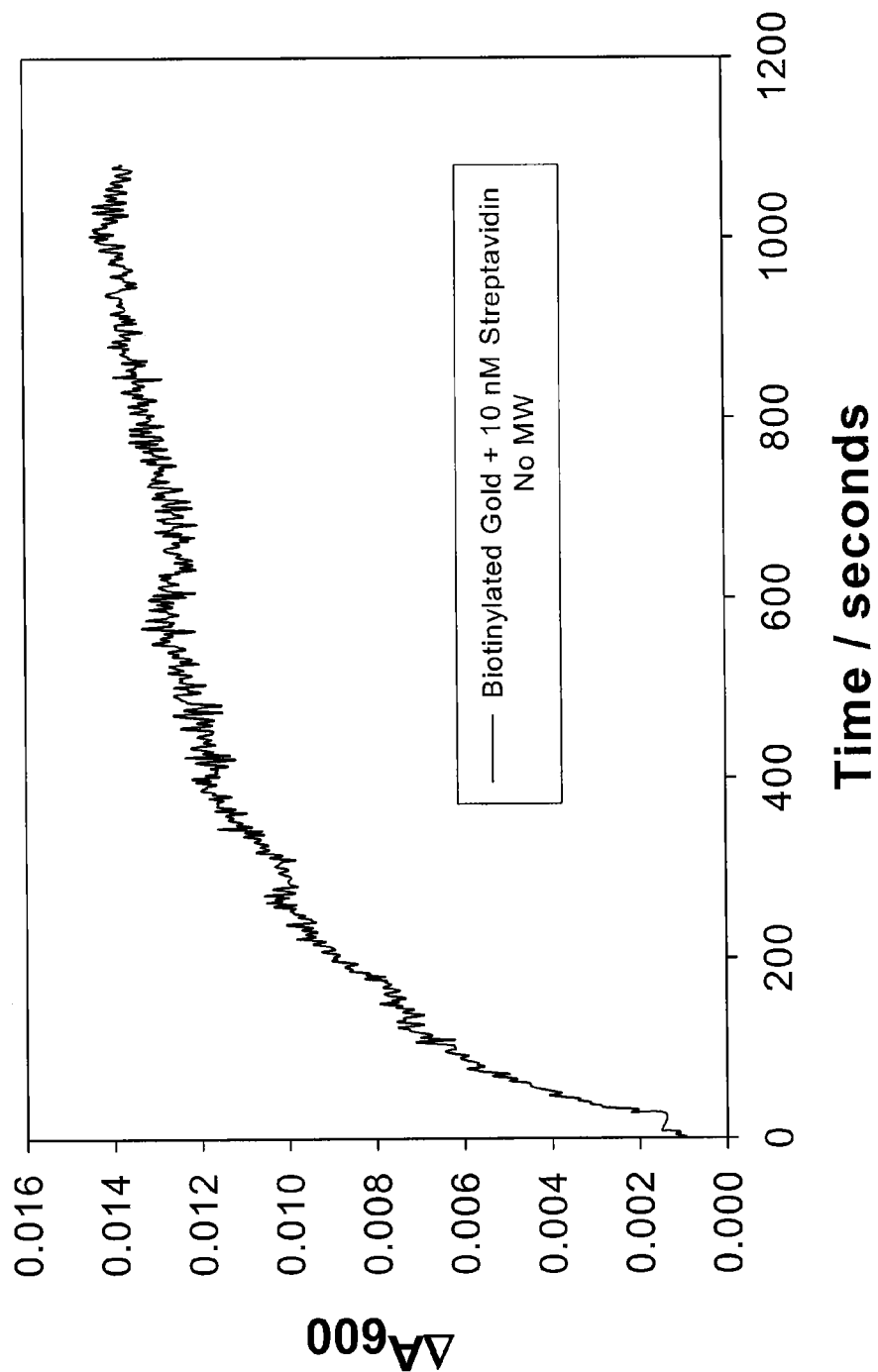
FIG. 3 shows the change in absorbance at 600 nm as a function of time for biotinylated-BSA coated 20 nm gold colloids cross linked by streptavidin.

Upon aggregation addition of 10 nM of streptavidin to the particles as schematically shown in FIG. 1, the particles rapidly aggregate. By monitoring the change in absorbance at an arbitrary wavelength (red-shifted from the Abs plasmon maxima), an increase in the absorbance at 600 nm is observed. This is shown in FIG. 3, which is a graph of the change in absorbance at 600 nm as a function of time for the biotinylated-BSA coated 20 nm gold colloids crosslinked by streptavidin. This figure indicates that the room temperature reaction is >90% kinetically complete at about 900 seconds, the graph indicating that the reaction likely requires a reaction time in excess of 20 minutes (1200 secs) to be kinetically complete.

By contrast, when the identical assay is heated using low power microwaves, the reaction is essentially complete in about 10 seconds, as is apparent from FIG. 4.

Figure 4A:
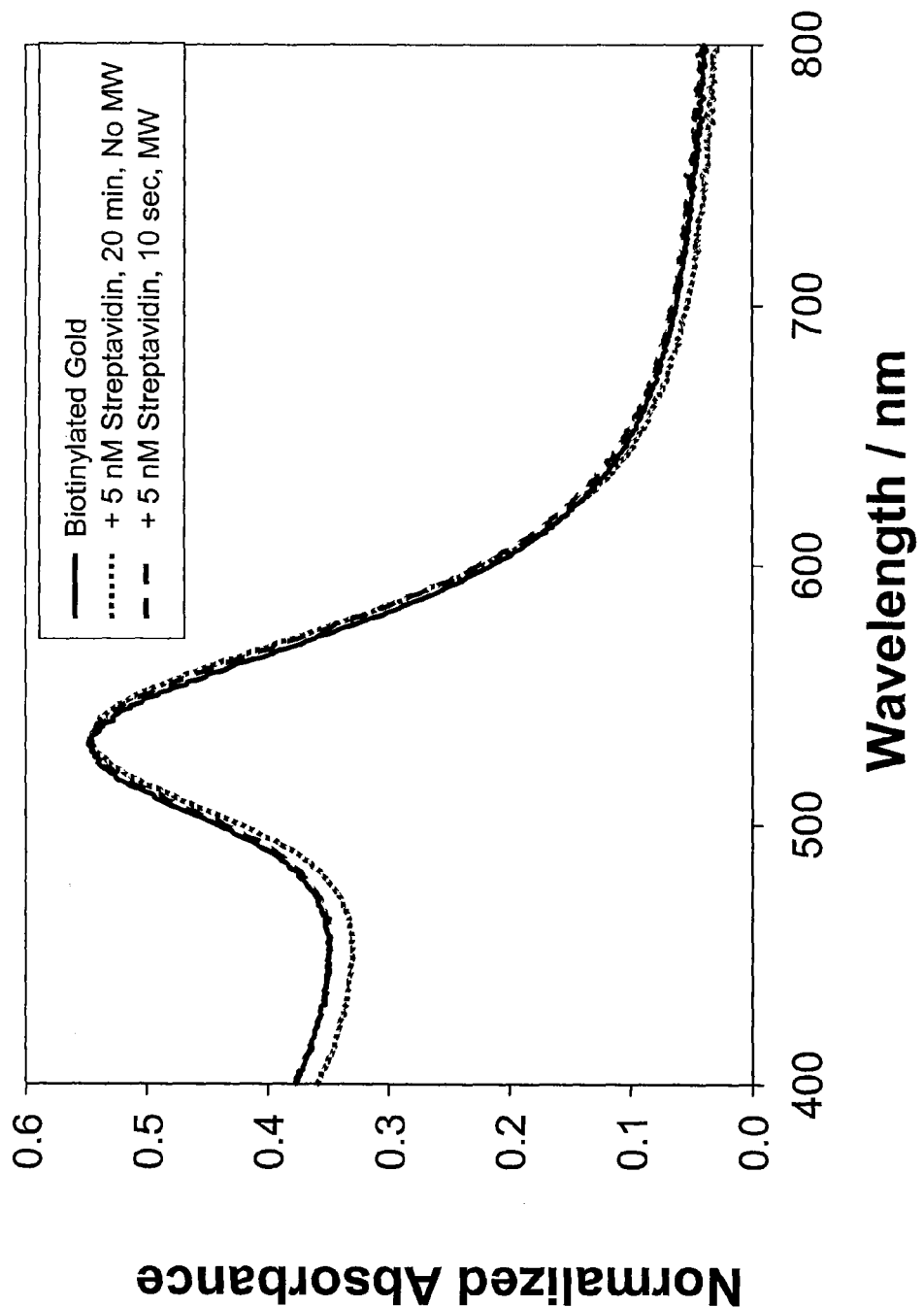
FIG. 4 shows the change in absorbance of biotinylated-BSA 20 nm gold colloids cross linked by different additions of streptavidin, both without (20 min incubation) and after low power microwave heating, with FIG. 4A showing the effect of a 5 nM streptavidin addition, FIG. 4B showing the effect of a 10 nM streptavidin addition, FIG. 4C showing the effect of a 20 nM streptavidin addition, and FIG. 4D showing the change in absorbance at 650 nm for both the room temperature incubated and microwave heated samples.
Figure 4B:
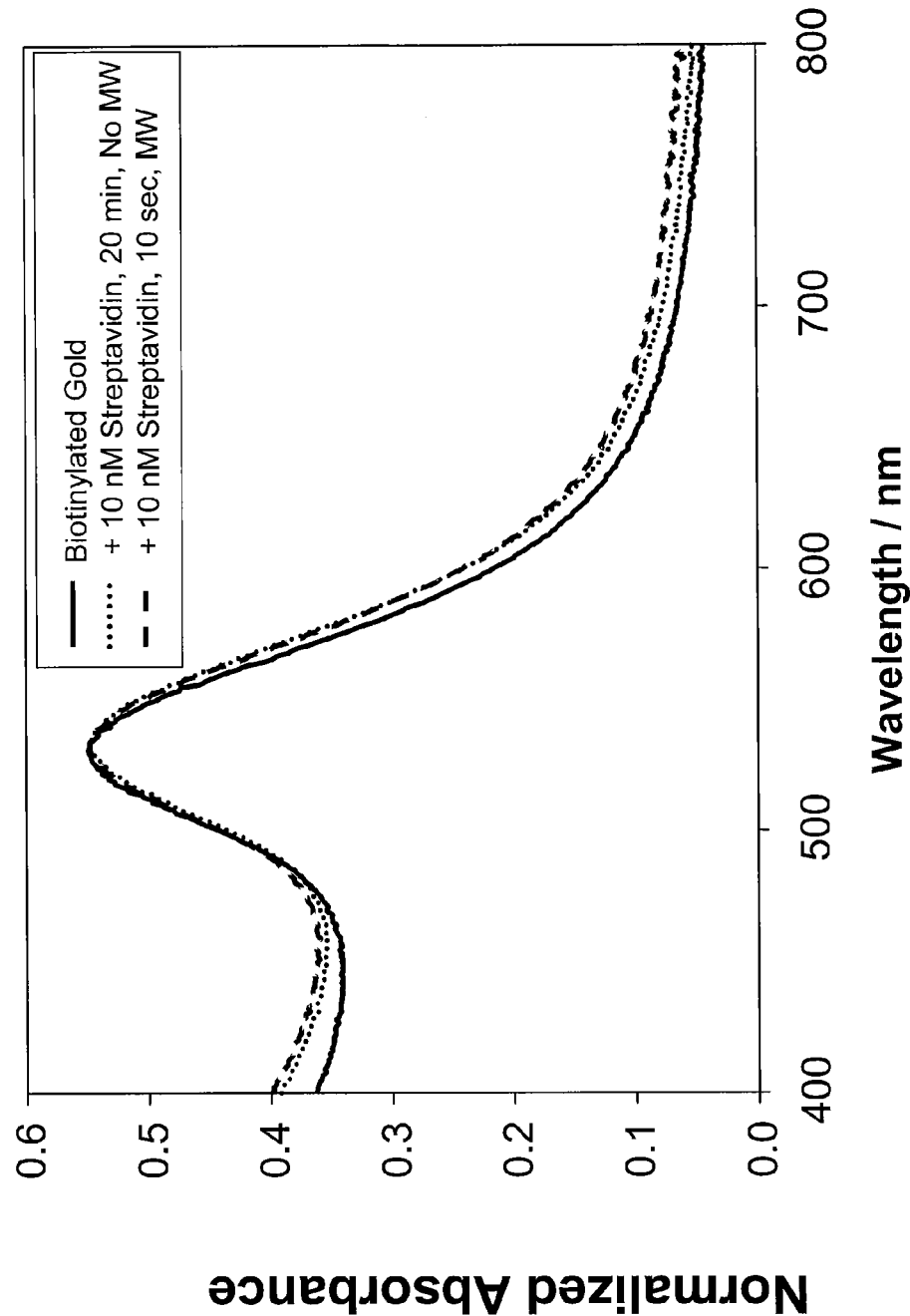
Figure 4C:
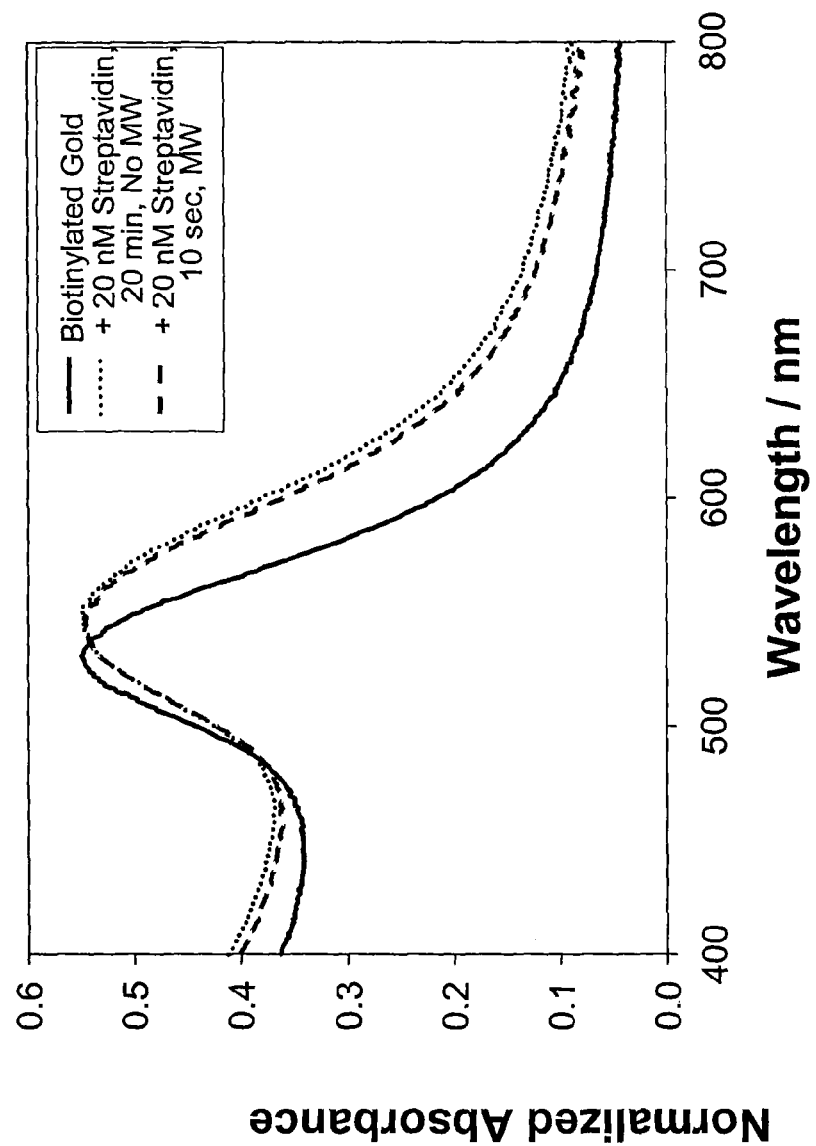
Figure 4D:
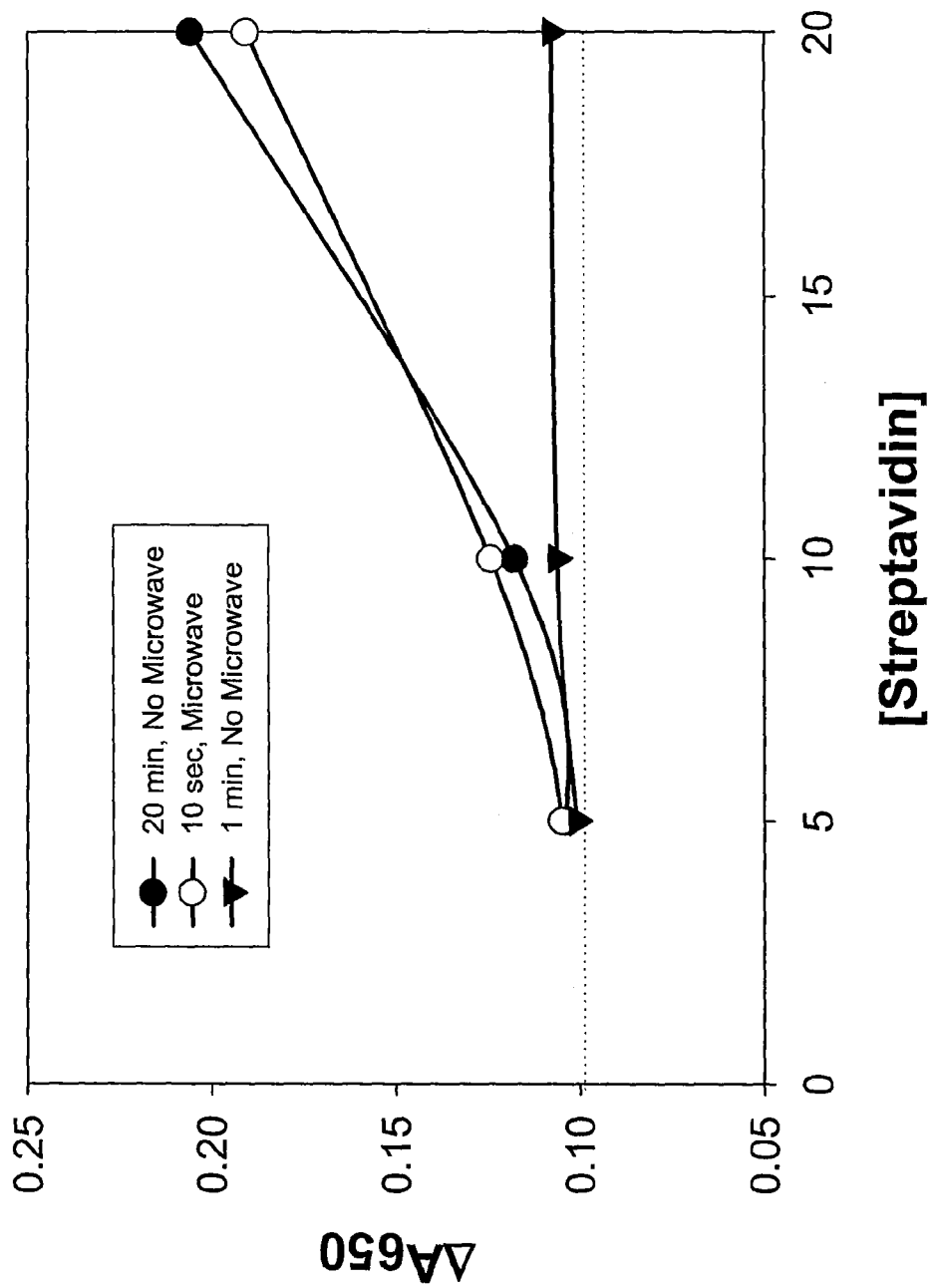

FIG. 4 shows the change in absorbance of biotinylated-BSA 20 nm gold colloids crosslinked by different additions of streptavidin, both without (20 min incubation) and after low power microwave heating, with FIG. 4A showing the effect of a 5 nM streptavidin addition, FIG. 4B showing the effect of a 10 nM streptavidin addition, FIG. 4C showing the effect of a 20 nM streptavidin addition, and FIG. 4D showing the change in absorbance at 650 nm for both the room temperature incubated and microwave heated samples.

These results shown that using low power microwaves to kinetically accelerate the assay affords for a greater than 90-fold increase in assay kinetics (10 seconds versus 900 seconds). For rapid diagnostic tests, such as for example are desired in clinical or bio-terrorism related applications, in instances in which a clinician or first responder needs to make an informed assessment very quickly, the invention therefore evidences the capability for significantly facilitating assay rapidity and alleviating current issues and bottlenecks in respect of assay run time.

Figure 5:
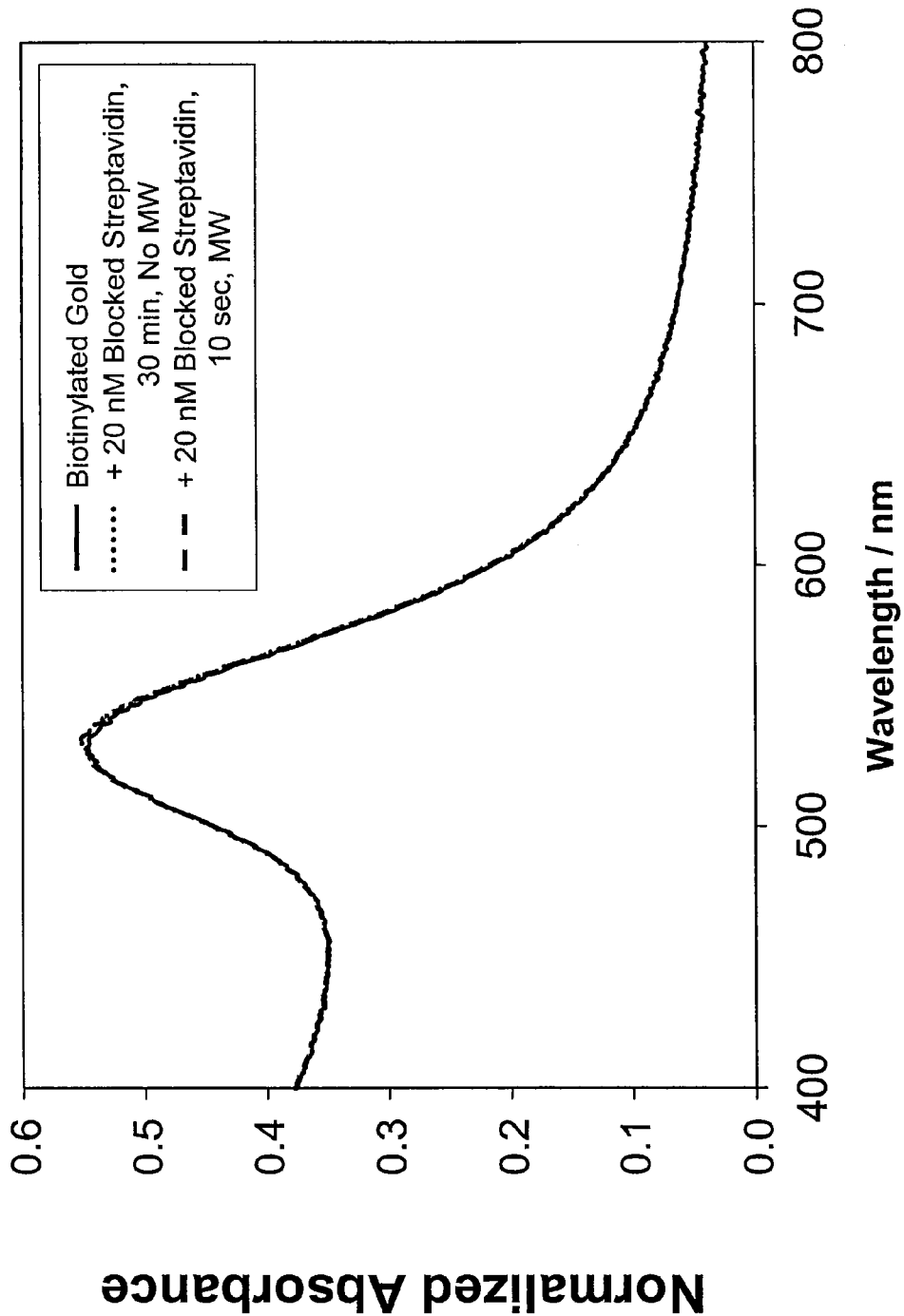
FIG. 5 shows absorption spectra of biotinylated-BSA 20 nm gold colloids in the presence of blocked streptavidin, after both a 30 minute incubation period and 10 seconds microwave heating.

The extent of non-specific absorption upon low power microwave heating, using blocked streptavidin, was also investigated, with the results shown in FIG. 5.

FIG. 5 shows absorption spectra of biotinylated-BSA 20 nm gold colloids in the presence of blocked streptavidin, after both a 30 minute incubation period and 10 seconds microwave heating. The low power microwaves did not facilitate any non-specific absorption by the Biotinylated-BSA coated colloids.

In application to long-term (extended life) sensor implementations, or long-term usage reversible sensors, it is important for the colloids or other plasmon resonance based structures to be unperturbed by heating. To assess the suitability of the microwave-accelerated plasmonics process and systems of the invention for such applications, solutions of colloids were heated to temperatures between 200° C. and 800° C. In all examples, both 20 and 200 nm colloids had plasmon absorption spectra, which were substantially identical before and after heating.

Figure 6A:
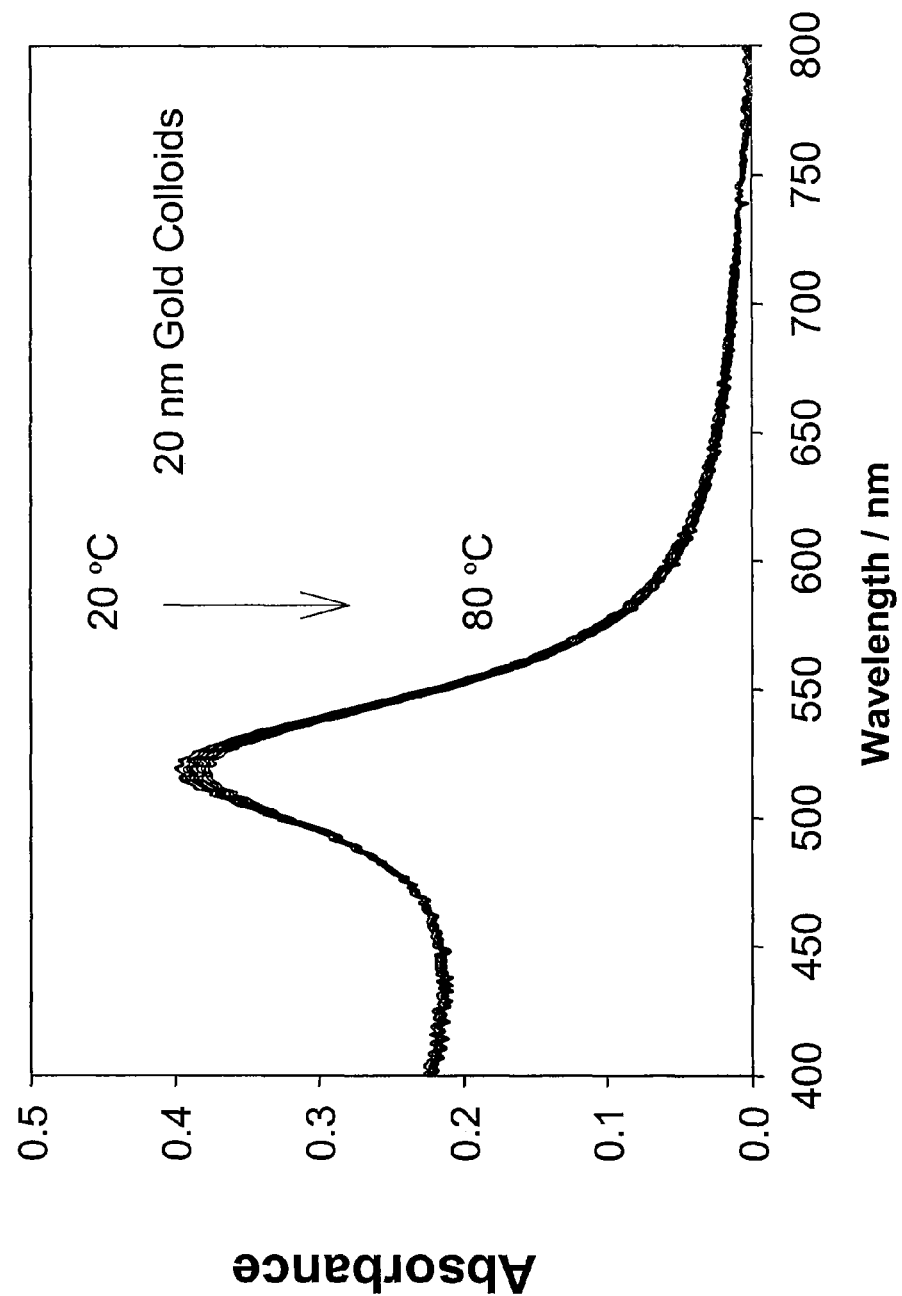
FIG. 6 shows the change in absorbance of both 20 nm (FIG. 6A) and 200 nm (FIG. 6B) virgin gold colloids as a function of temperature, and the respective change in absorbance as a function of temperature (FIG. 6C).
Figure 6B:
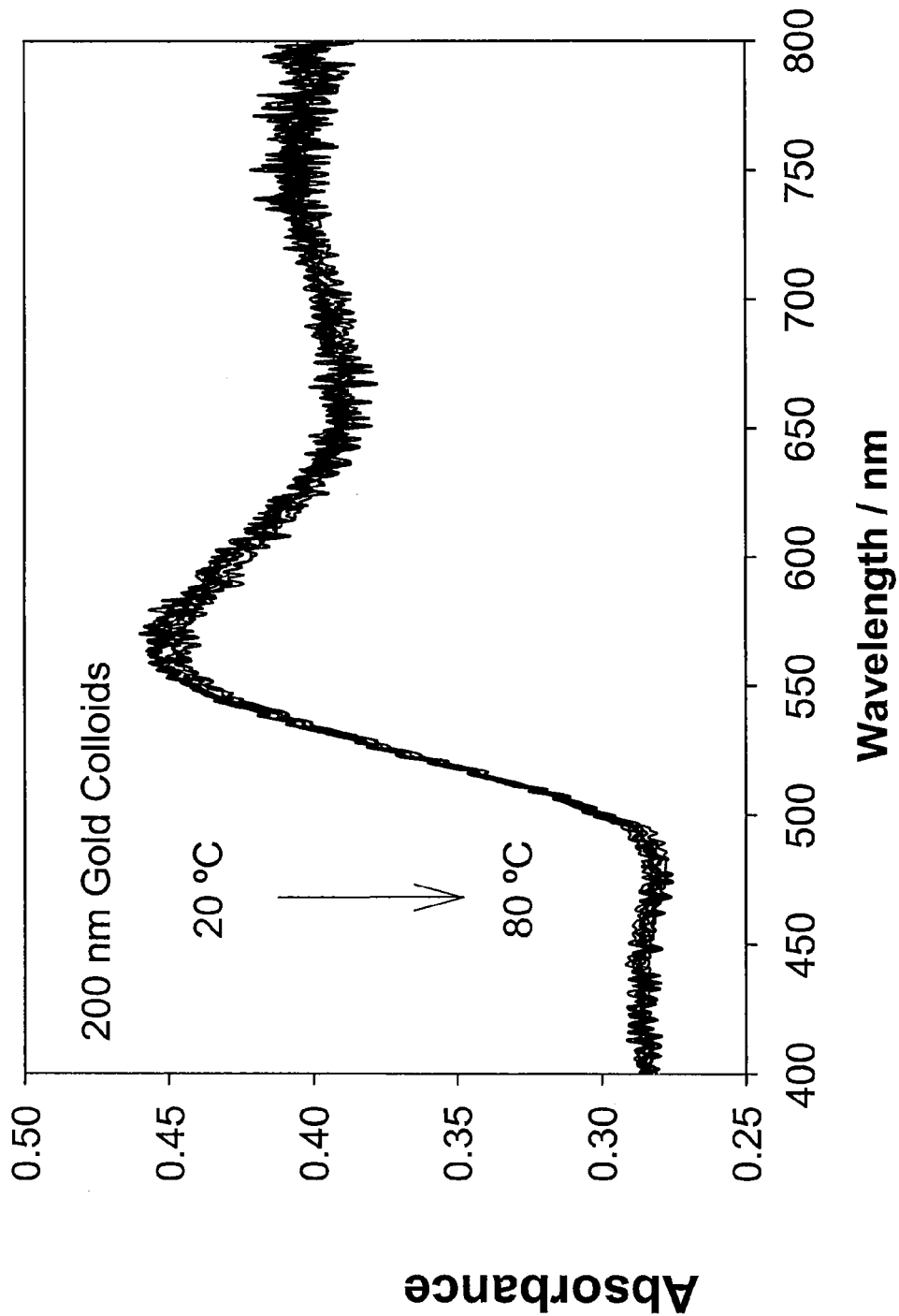
Figure 6C:
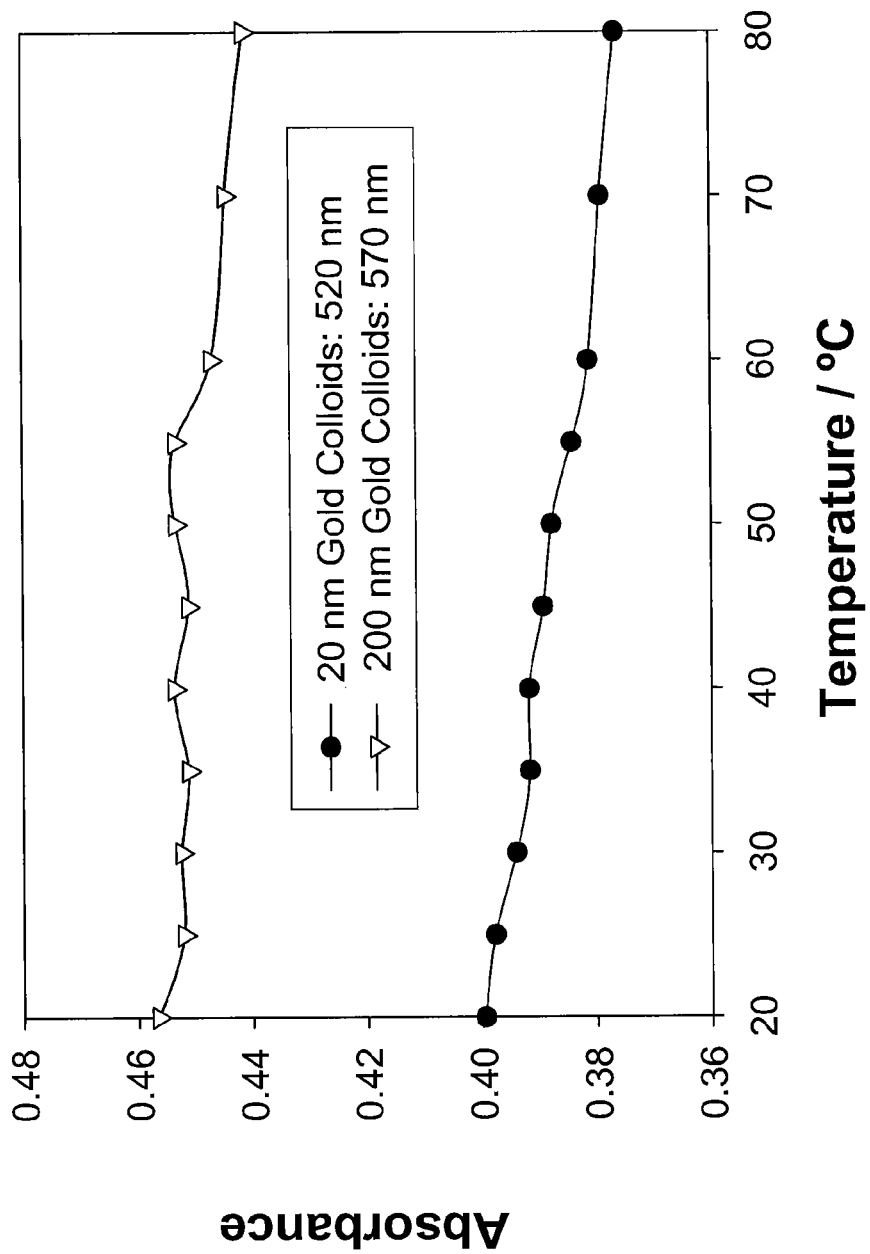

FIG. 6 shows the change in absorbance of both 20 nm (FIG. 6A) and 200 nm (FIG. 6B) virgin gold colloids as a function of temperature, and the respective change in absorbance as a function of temperature (FIG. 6C).

FIG. 6C shows that the total plasmon absorption maxima at either 520 nm (for 20 nm colloids) or 570 nm (for 200 nm colloids) is slightly reduced at elevated temperatures, which is potentially attributable to the difference in refractive index of water (buffered media) at 200° C. as compared to 800° C.

Figure 7A:
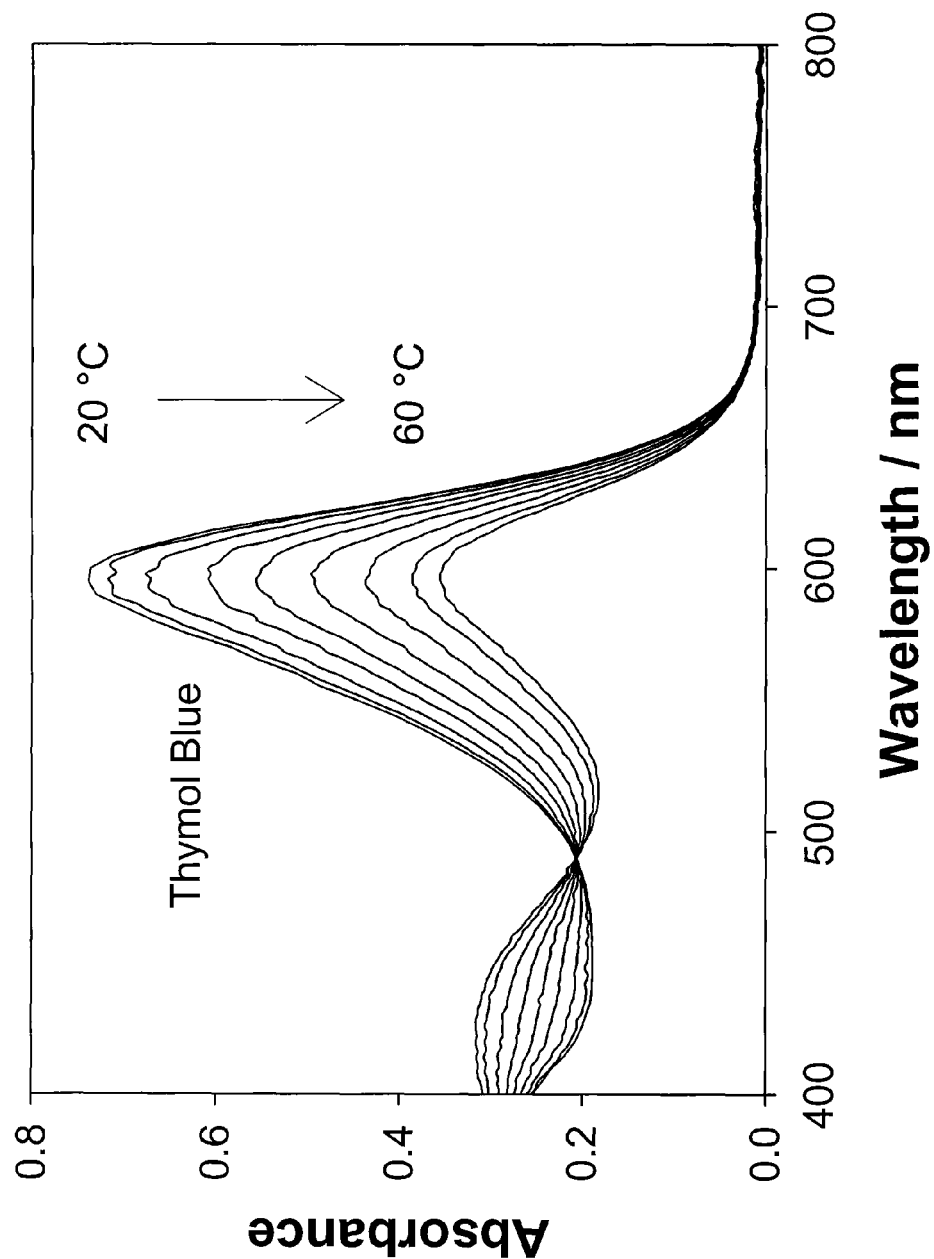
FIG. 7 shows absorption spectrum of thymol blue as a function of temperature (FIG. 7A), the same solution containing 20 nm colloids (FIG. 7B), and the respective A600/A425 ratiometric plots Vs temperature (FIG. 7C).
Figure 7B:
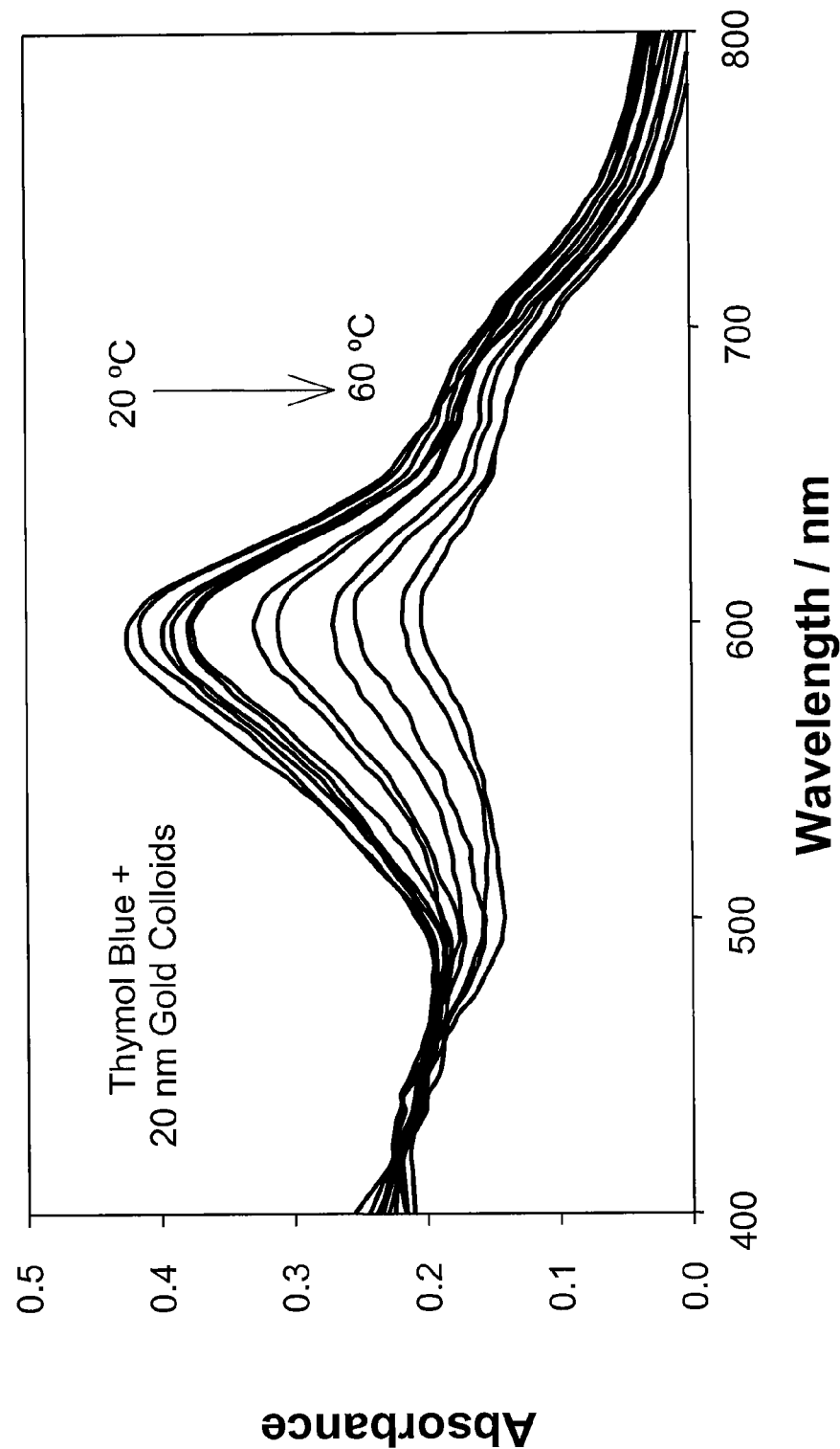
Figure 7C:
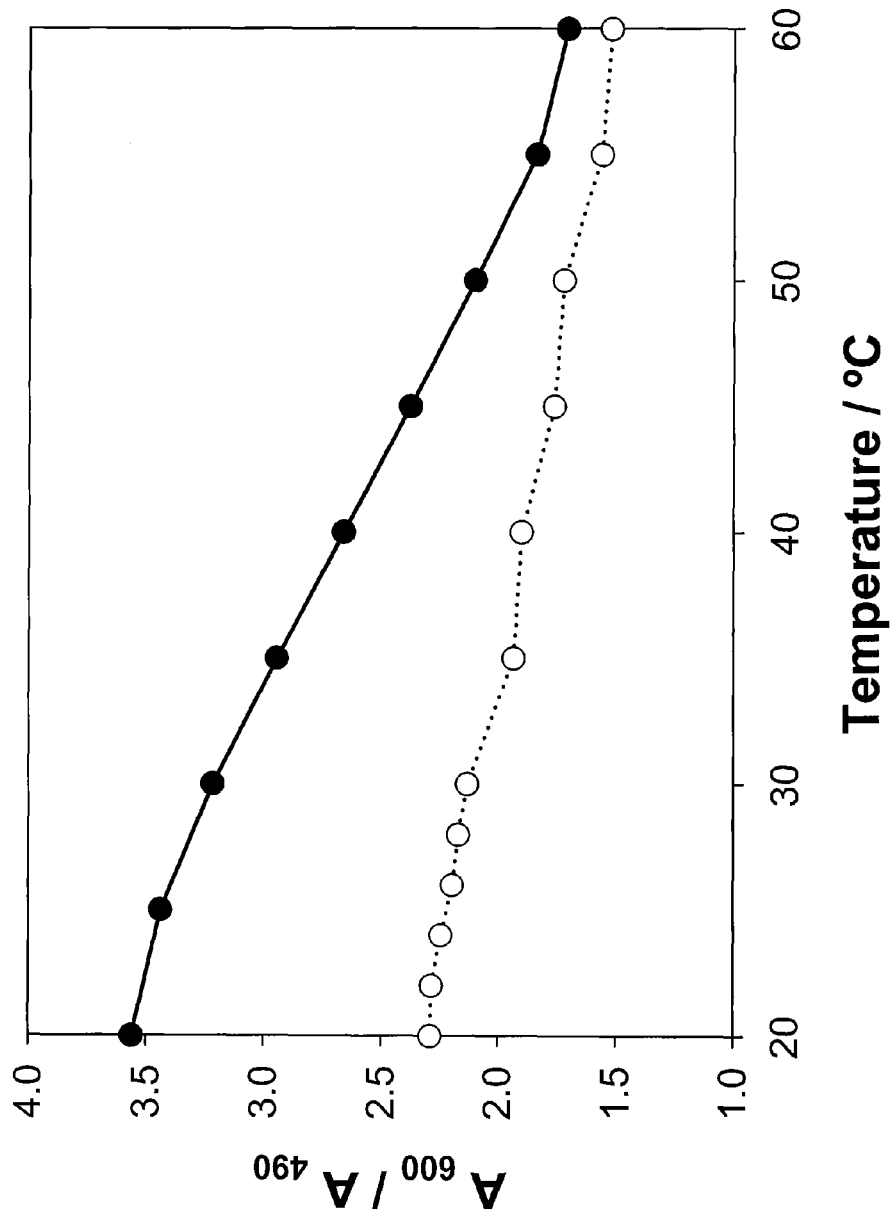

In order to ascertain the temperature jump in the low power microwave heated colloidal system that facilitates the observed >90-fold increase in assay kinetics, a temperature dependent probe, thymol blue (0.5 mM thymol blue, in 50 mM tris acetate, pH 9.0) was utilized. The absorption spectrum of thymol blue was recorded as the temperature was gradually increased from 200° C. to 800° C. The results are shown in FIG. 7, which includes an absorption spectrum of thymol blue as a function of temperature (FIG. 7A), the same solution containing 20 nm colloids (FIG. 7B), and the respective A600/A425 ratiometric plots as a function of temperature (FIG. 7C).

The color of the solution changed with temperature (not microwave heated) from deep magenta to pale yellow, due to the temperature dependence of the ionization constant of the tris buffer. As the temperature was increased, the pH of the solution decreased and the distribution of the ionization states of the thymol blue dye changed, resulting in a color change as a function of temperature. The reversible color change was readily observed in the UV-Vis spectrum by changes in the 425 nm and 600 nm spectral bands. In addition, the change in absorption spectrum was determined as 20 nm gold colloids were heated (not microwave heated) in the presence of the thymol blue. A shoulder developed at ~680 nm, which is due to the high pH of the tris buffer.

Figure 8A:
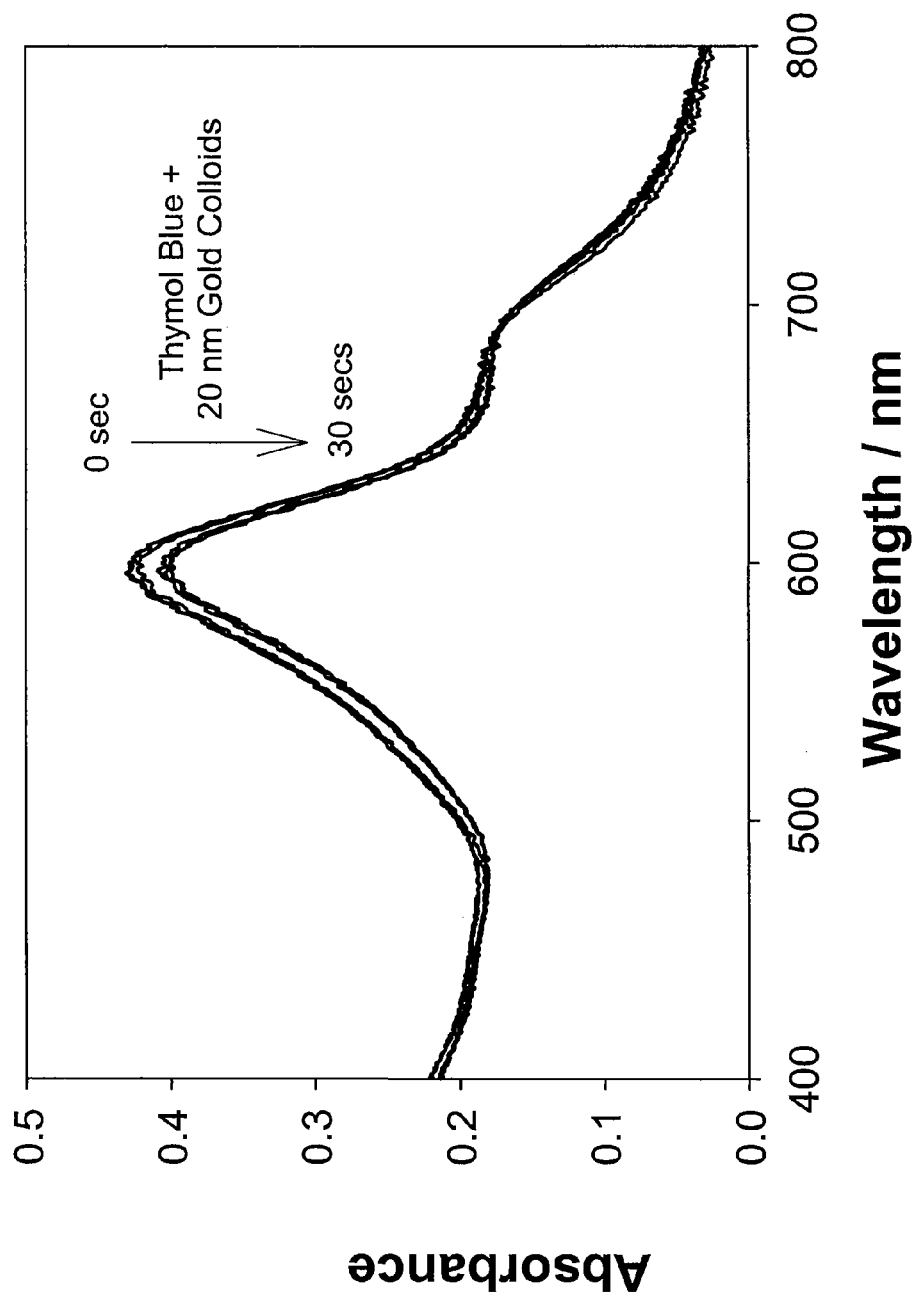
FIG. 8 shows absorbance spectra of 450 μL of 20 nm gold colloids and thymol blue microwave heated in the black body for different times (FIG. 8A), 450 μL of thymol blue solely heated in the black body (FIG. 8B), and the respective ratiometric plots (FIG. 8C).
Figure 8B:
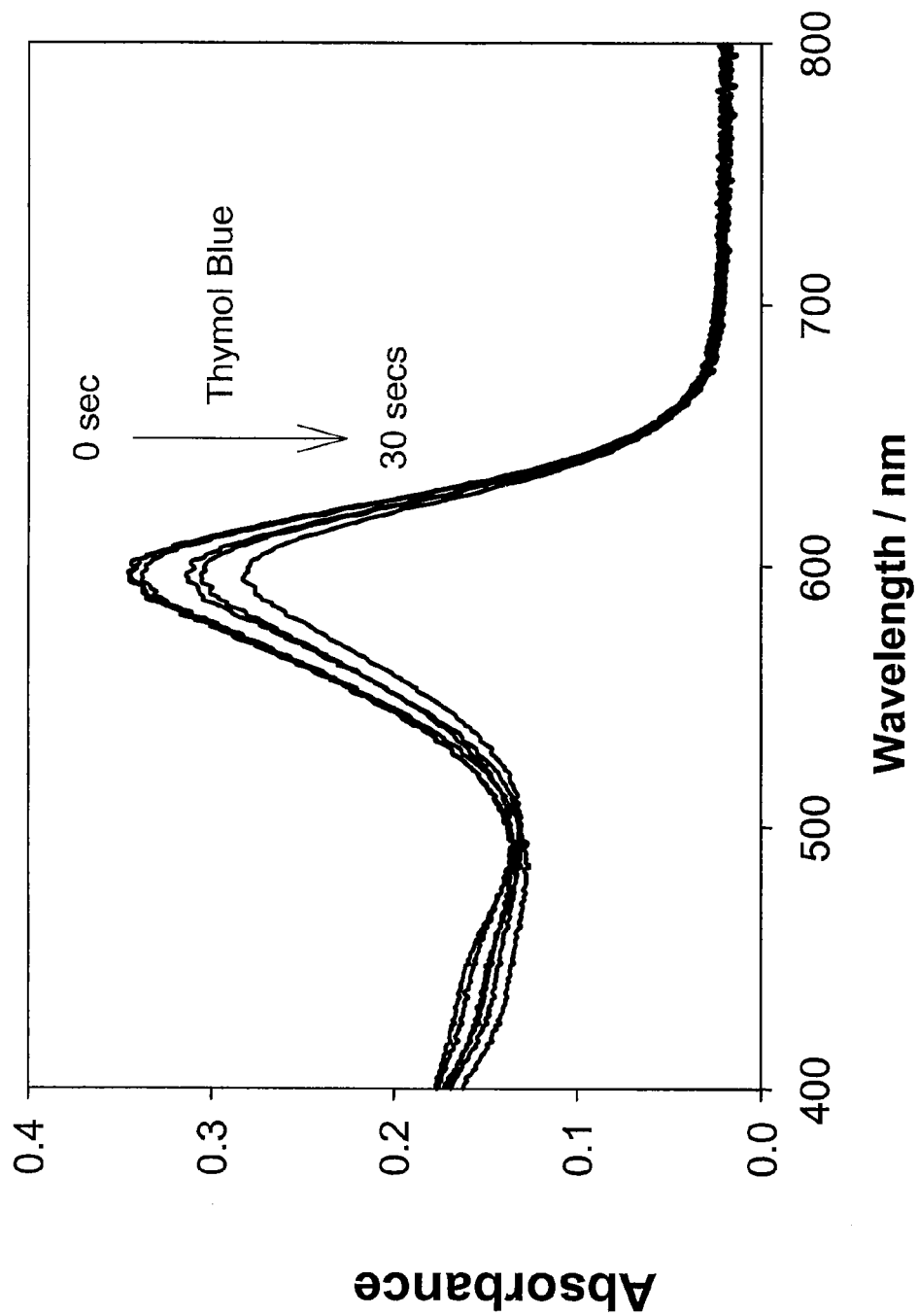
Figure 8C:
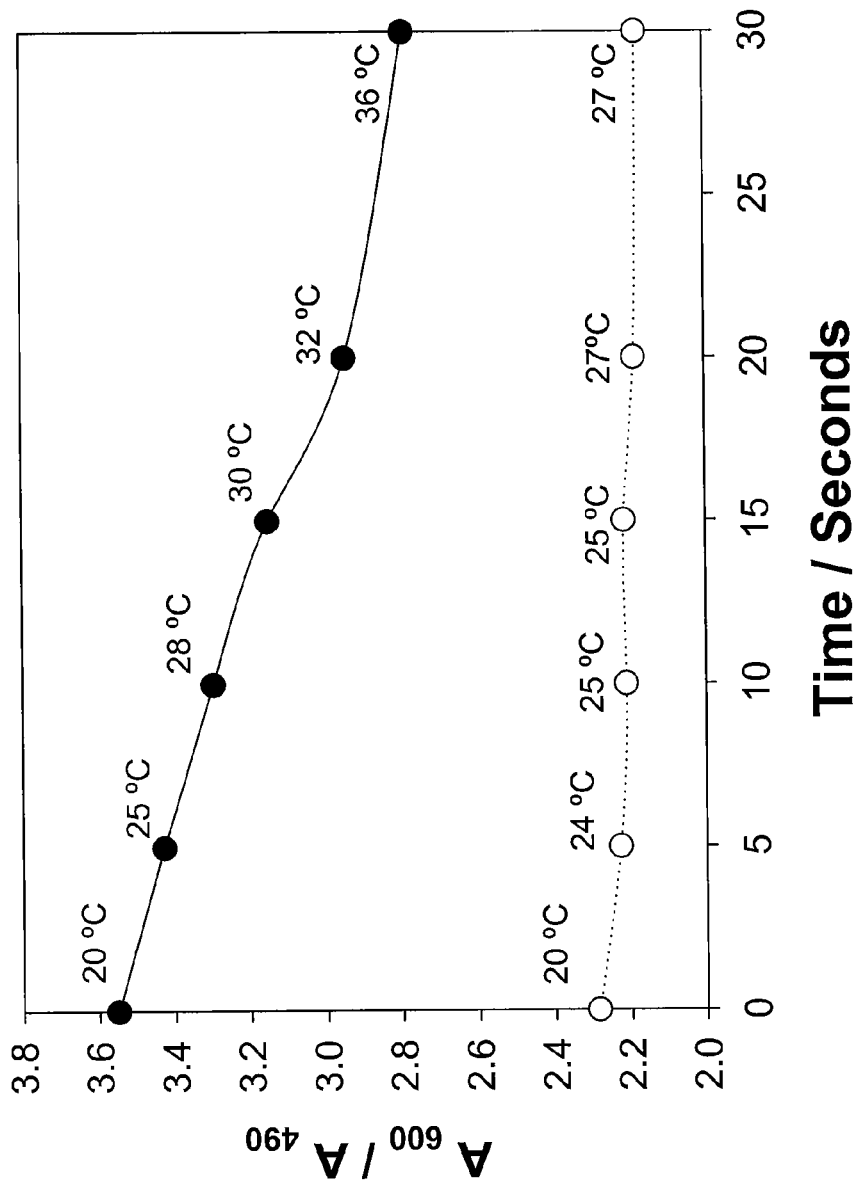

FIG. 8 shows absorbance spectra of 450 μL of 20 nm gold colloids and thymol blue microwave heated in the black body for different times (FIG. 8A), 450 μL of thymol blue solely heated in the black body (FIG. 8B), and the respective ratiometric plots (FIG. 8C).

When a 0.27 nm solution of gold colloids and thymol blue was microwave heated (FIG. 8A), it can be deduced that the temperature jump of the bulk solvent is approximately 50 C for 10 seconds heating (FIG. 8C). Given the >90-fold change in assay kinetics shown in FIG. 4, this suggests that the local temperature around/of the colloids is significantly higher, since a 50° C. temperature jump of the local solvent does not explain the observed 90-fold increase in assay kinetics. Preferential heating of plasmon resonance particles in the microwave cavity, relative to the bulk solvent, thus emerges as a causal factor to account for the rapid kinetics observed. Such local heating of the colloids enables increased assay kinetics (temperature accelerated kinetics) to occur close to the particles, and promotes greater particle momentum in solution, so that the particles are able to sense a greater solution volume per unit time.

Figure 9:
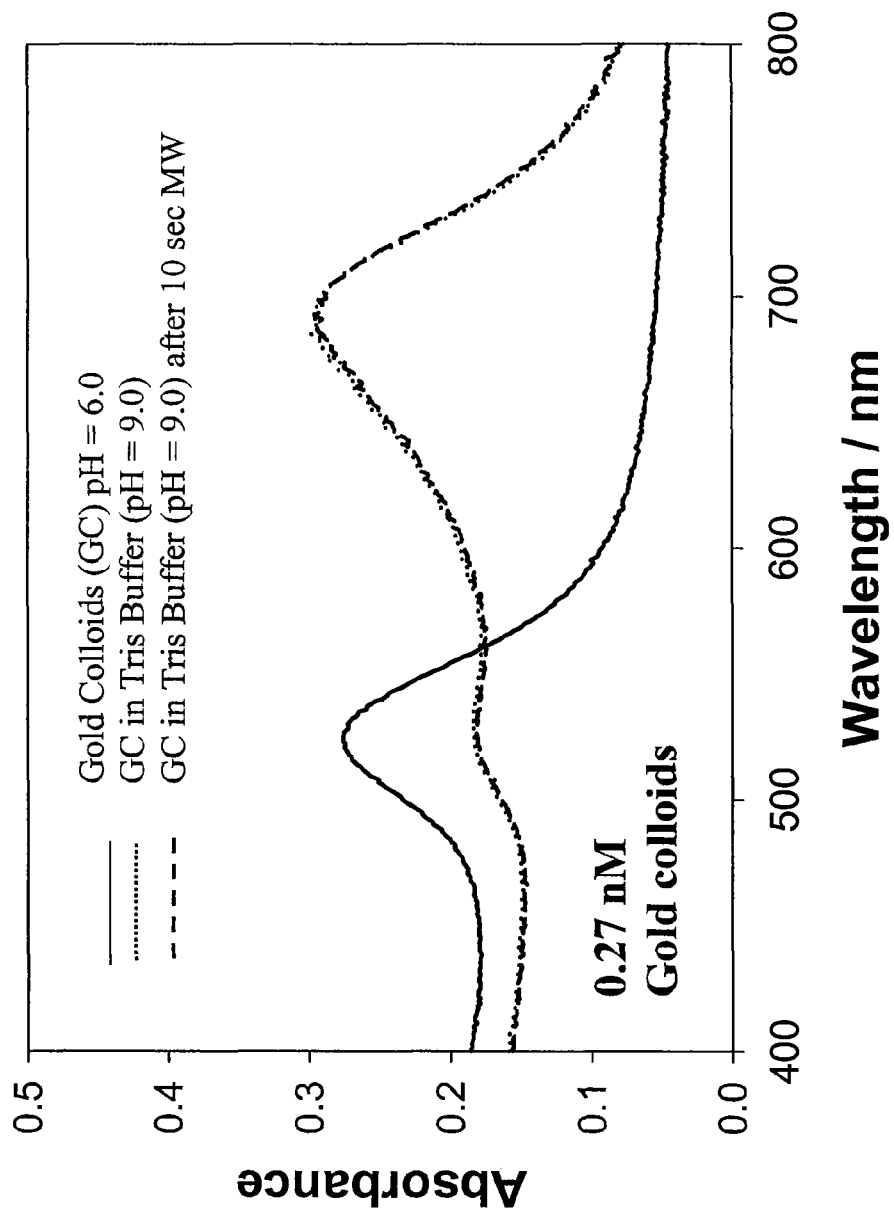
FIG. 9 shows absorbance spectra of 20 nm gold colloids in pH 6.0, 9.0 and after microwave heating.
Figure 10:
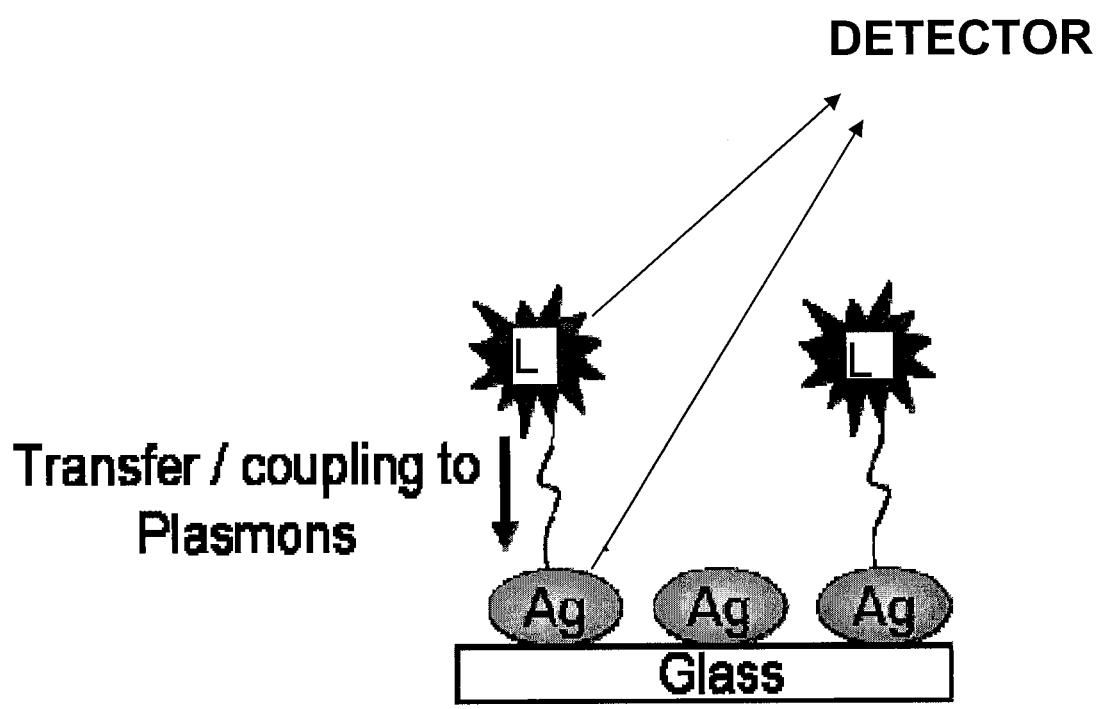
FIG. 10 illustrates coupling of plasmonic emissions to emitted radiation from fluorescing molecules.

FIG. 9 shows absorbance spectra of 20 nm gold colloids in pH 6.0, 9.0 and after microwave heating.

Example 3

Bovine-biotinamidocaproyl-labeled Albumin (biotinlyated-BSA) and premium quality plain glass microscope slides (75×25 mm) were obtained from Sigma-Aldrich. Quantum dot 655-labeled streptavidin (Qdots-streptavidin) was obtained from Molecular Probes (Eugene, Oreg.). All chemicals were used as received.

Methods

Figure 11:
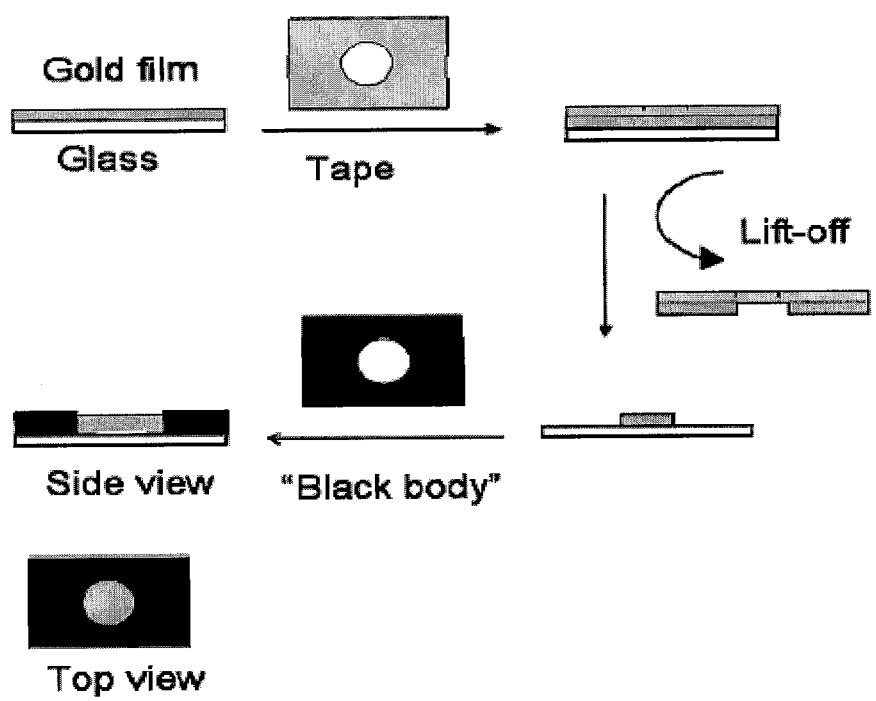
FIG. 11 shows a schematic representation of producing gold-coated glass slides (Gold Disks) with a 5 mm gold spot for MA-SPCL bioassays.

Preparation of the Metal Films for Surface Plasmon Coupled Luminescence (SPCL) Spectroscopy Firstly, the plain glass slide was coated with a 50 nm thick gold film by vapor deposition (EMF Corp., Ithaca, N.Y.). Then, a tape with a 5 mm circular disk is applied onto the gold film and was lifted-off the surface that resulted in the removal of the gold film except a 5 mm circular disk (FIG. 11). Finally, a black electrical tape that is attached to a self-sticking paper, containing a 5 mm wide circular disk (referred to as a "black body") was attached on the gold-coated glass slide while the two circular disks matched, prior to the assay fabrication and subsequent SPCL experiments.

Microwave-Accelerated SPCL Assay

The model assay is based on the well-known interactions of biotin and streptavidin. Biotin groups are introduced to the metal surface through biotinylated-BSA, which, similar to HSA, readily forms a monolayer on the surfaces of glass and noble metals (Green, 1975). Binding of the biotinylated-BSA to the metal film was accomplished by incubating 10 Mm biotinylated-BSA solution in the "black-body" micro cuvettes for 30 minutes, followed by rinsing with deionized water to remove the unbound material. For the model assay, then a 30 μl of varying concentrations of Qdots-streptavidin was subsequently added into the biotinylated-BSA coated metal film-coated micro cuvettes for 30 minutes for the control experiments at room temperature (20° C.), and 1 minute in the microwave cavity (0.7 cu ft, GE Compact Microwave Model: JES735BF, max power 700 W). The power setting was set to 3 which corresponded to 210 W over the entire cavity. This power is similar to the numerous reports using low power microwaves for immunolabeling (Chicoine, 1998), immunostaining (Micheva, 2001; Petrali, 1998), in immunocytochemistry (Madden, 1998; Rangell, 2000; Schichnes, 1999) and histological microwave processing (Rassner, 1997; Schray, 2002). In all the experiments performed with low power microwaves, using metal film-coated micro cuvettes modified with the "black body", there was no evidence of surface drying. The coated slides were attached to a hemicylindrical prism made of BK7 glass with index matching fluid. This combined sample was positioned on a precise rotary stage that allows excitation and observation at any desired angle relative to the vertical axis along the cylinder. The sample was excited using the Reverse Kretschmann configuration (FIG. 12) from the air or sample side, which has a refractive index lower than the prism. The excitation was from the second harmonic (473 nm) of the diodepumped Nd:YVO4 laser (compact laser pointer design, output power ≈30 mW) at an angle of 90 degrees. Observation of the emission was performed with a 3 mm diameter fiber bundle, covered with a 200 μm vertical slit, positioned about 15 cm from the sample. This corresponds to an acceptance angle below 0.1°. The output of the fiber was connected to an Ocean Optics HD2000 spectrofluorometer to measure the florescence emission spectra through a 488 nm super notch filter.

Figure 13:
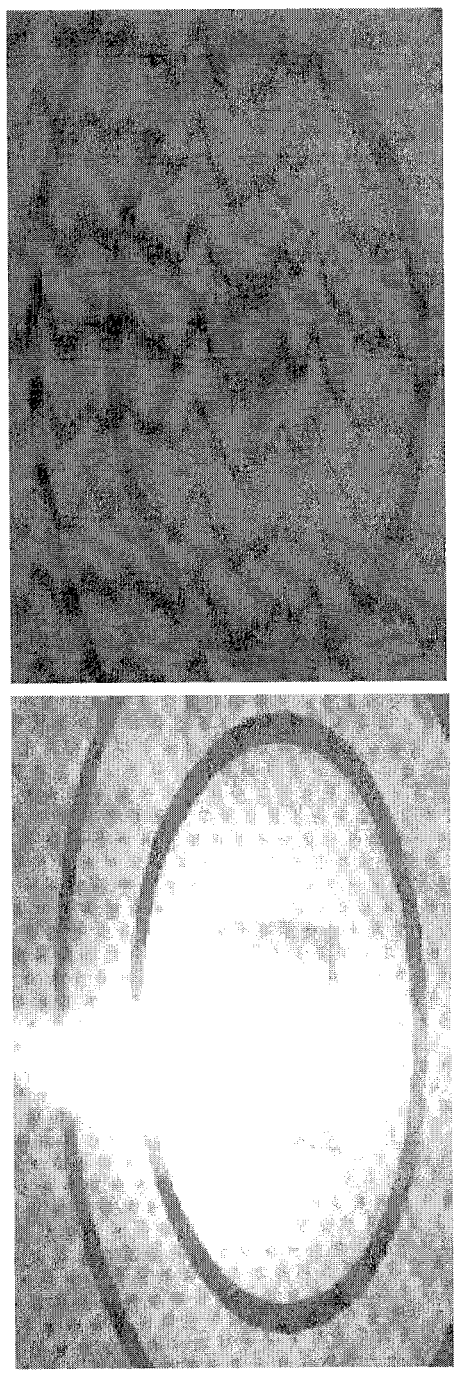
FIG. 13 shows photographs of gold-coated glass slides during microwave heating. (Left)—The glass slide with a continuous gold coating (size≈>λ/10), and (Right)—the glass slide with a 5 mm diameter gold disk (size≈<<λ/10). While the glass slide with a continuous gold coating sparks and arcs within seconds, the glass slide featuring a small 5 mm diameter gold disk is not affected during 1 minute of microwave heating.

In order for the gold-coated glass slides to be used in MA-SPCL bioassays, they have to withstand the microwave heating while the bioassay is being driven to completion, as well as further physical treatments, such as multiple buffer washing steps. Thus, at first, the feasibility of the gold coated glass slides, like those commonly used in Surface Plasmon Fluorescence Spectroscopy (Kambhampati, 2001; Liebermann, 2000a; Liebermann, 2000b) and Surface Plasmon Resonance (Lofas, 1991) were tested for their use in MA-SPCL assays via exposure to microwaves. FIG. 13-*left*, shows the photograph of typically used gold-coated glass slide during microwave heating. When exposed to microwaves, the glass slide with a continuous gold coating sparks and is destroyed within seconds, proving them not to be useful with MA-SPCL bioassays. However, the glass slide featuring only a 5 mm gold disk and a black body, made from the same gold-coated glass slide used in FIG. 13-L*eft*, is not destroyed even after continuous (1 minute) and repetitive (5 times) microwave heating, FIG. 13-R*ight*. This was possible due to (1) the fact that the surface area of the gold disks is smaller than the area required for the surface charge buildup (Whittaker 1993) and eventual destruction of the gold coating, and (2) the black body absorbs an excess of the microwaves, providing additional protection for the gold coating. In the light of these observations, only the glass slide featuring a 5 mm gold disk can be used for MASPCL bioassays, a significant observation and finding, and attributed to the size of the disk being sub-wavelength with respect to the microwaves.

Figure 14:
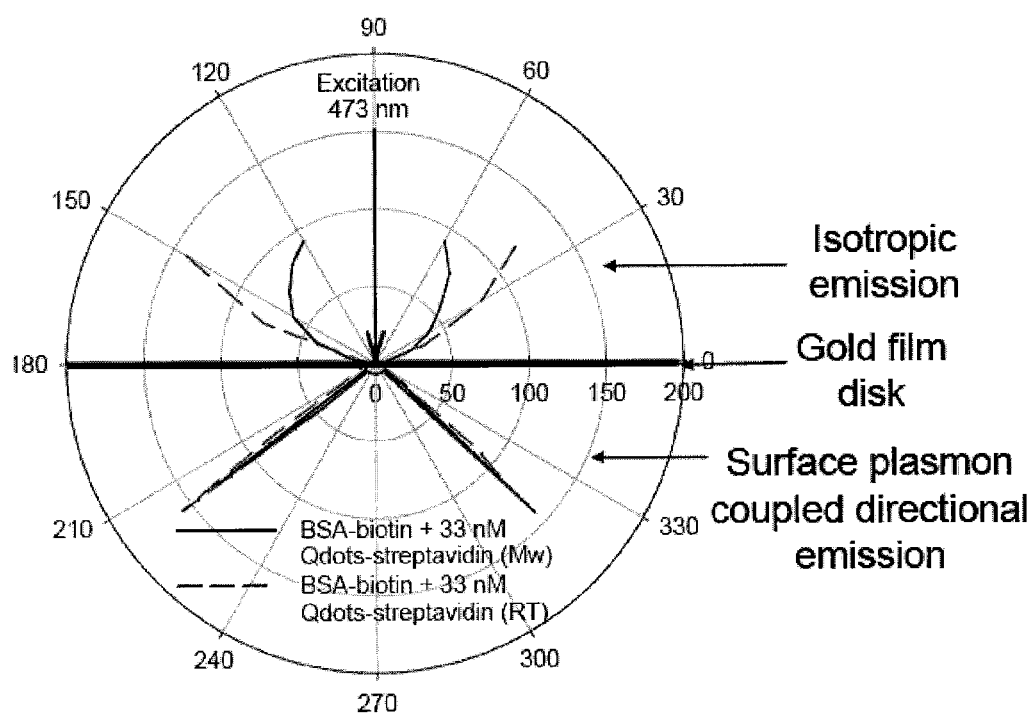
FIG. 14 shows the angular distribution of luminescence for 33 nM of quantum dots-streptavidin used in the MA-SPCL assay, both microwave heated (Mw) and run at room temperature (RT). Angularaxis: 0 to 360 degrees, radial-axis: Luminescence Intensity in arbitrary units (A.U.). The background intensity (noise) was 6 A.U. See FIG. 12 for the experimental setup.

To demonstrate MA-SPCL bioassays on small disk gold films, a model assay was employed that was based on the well-known interactions of biotin and avidin (Wilchek, 1990; Baziard, 1988). The model protein assay was constructed with biotinylated-BSA surface modified gold films and streptavidin-modified quantum dots, and run both at room temperature and microwave accelerated (heated). This model protein system affords for simple kinetics, i.e. no back reactions are expected due to the strong association of biotin and avidin (Wilchek, 1990; Baziard, 1988). FIG. 14 shows the angular distribution of luminescence for 33 nM of quantum dots used in the MA-SPCL assay, both microwave heated (Mw, 1 minute) and run at room temperature (RT, 30 minutes).

The surface plasmon coupled luminescence (observed through a prism between the angles of 180 and 360 degrees, see FIG. 14 for the experimental setup) is of similar intensity and is highly directional at two angles, 217 and 323 degrees, for MA-SPCL assays, both microwave heated and run at room temperature, FIG. 14. This indicates that the biotin-avidin interactions, which took place in 30 minutes at room temperature, were completed within 1 minute using microwave heating, corresponding to a 30-fold increase in kinetics due to microwave heating.

The experiments showed that at least 1 minute of microwave heating was required for the kinetics of biotin-avidin interactions on the gold film to be completed in the MA-SPCL technique (data not shown), where the completion of the assay kinetics was evaluated by comparing the signal from the same assay undertaken at room temperature. The free-space luminescence (between the angles of 0 and 180 degrees) for MA-SPCL assays both microwave heated and at room temperature, are isotropic and are similar to the intensity observed on the prism side (217 or 323 degrees).

Figure 15:
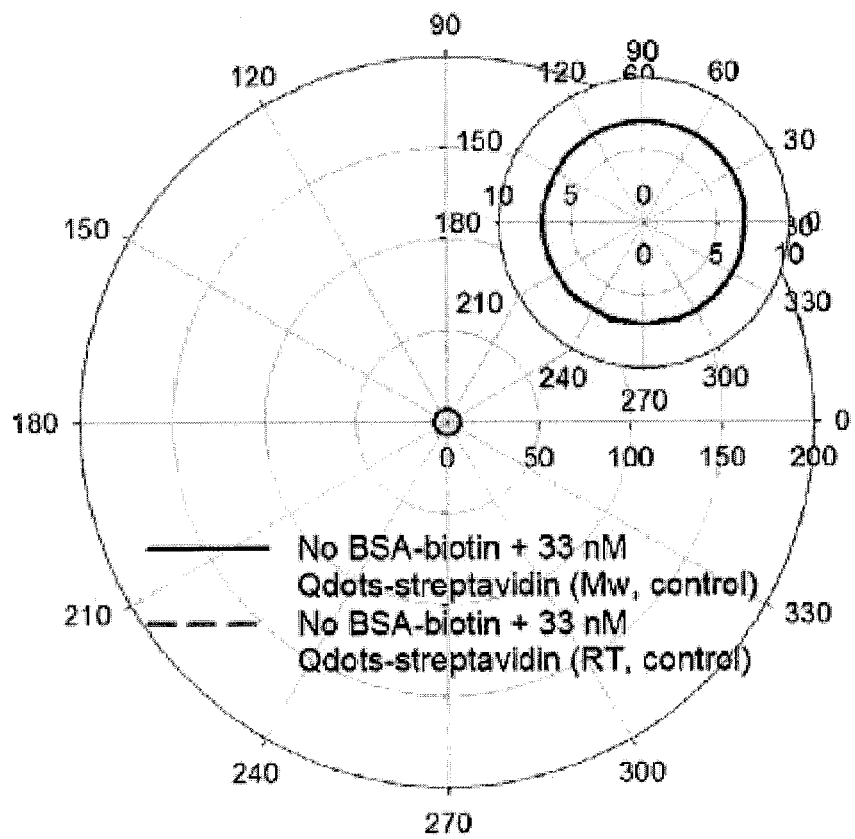
FIG. 15 shows the angular distribution of luminescence for 33 nM of quantum dots-streptavidin used in the control MA-SPCL assay (Mw, control) and at room temperature (RT, control). The control assay is undertaken by omitting one of the binding partners, i.e., BSA-biotin. The inset shows an enlarged region. Note that FIG. 15 is drawn to the same scale as FIG. 14. Angular-axis: 0 to 360 degrees, radial-axis: Luminescence Intensity in arbitrary units (A.U.). The background intensity (noise) was ≈6 A.U. A.U.—Arbitrary units.

A control assay, where one of the binding partners, i.e., BSA-biotin is omitted, was also undertaken both at room temperature (RT) and with microwave heating (Mw) to determine the extent of non-specific binding to the surface of the gold films. FIG. 15 shows the angular distribution of luminescence for 33 nM of quantum dots used in the control MA-SPCL assay. As can be seen from FIG. 15, the luminescence intensity was similar to the background intensity both at room temperature and the MA-SPCL assay, which indicated there is very little nonspecific binding of the quantum dots-streptavidin when the biotinylated-BSA was not present on the surface.

Figure 16:
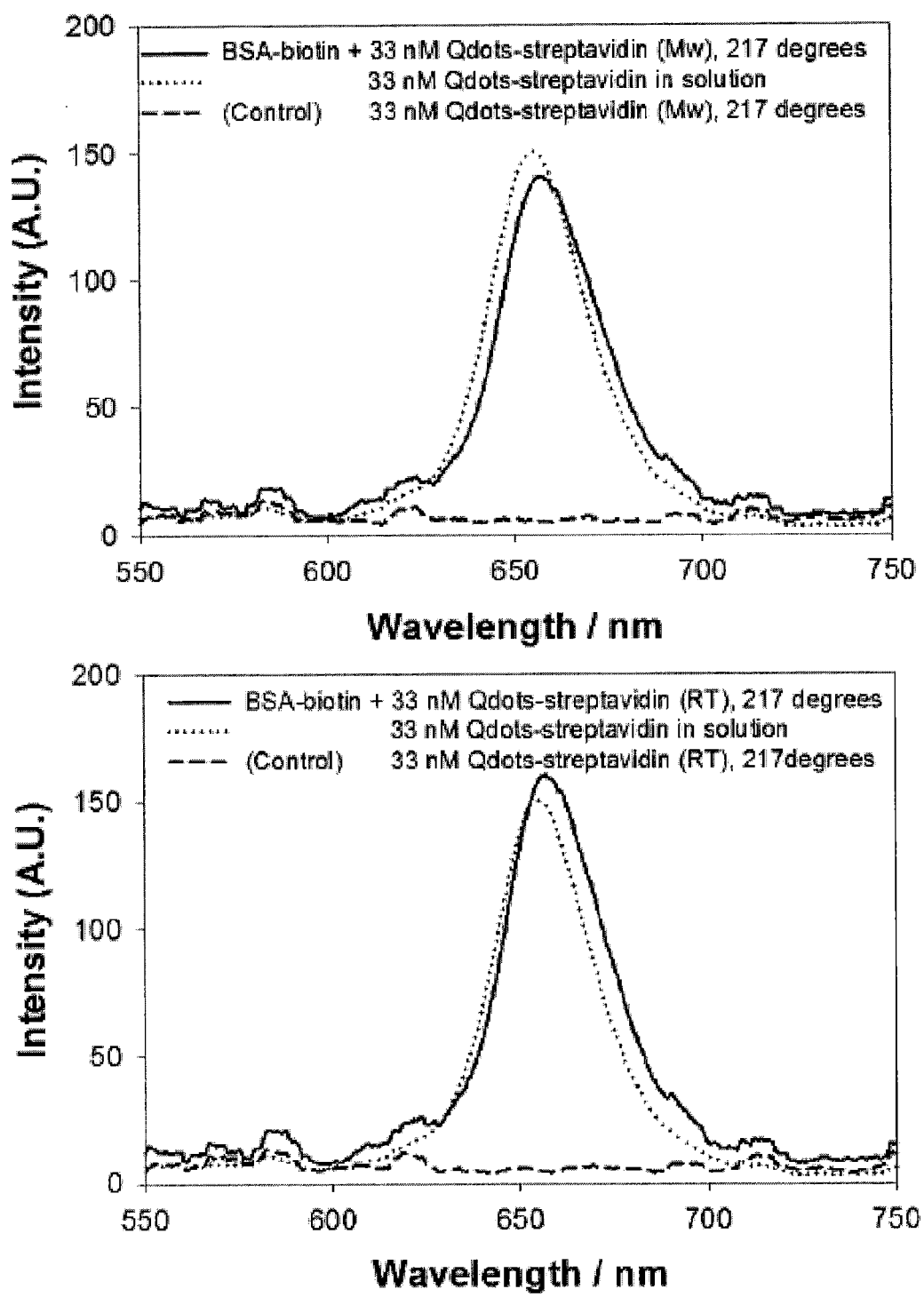
FIG. 16 the emission spectra for 33 nM quantum dots used in the MA-SPCL assay and the control MA-SPCL assay, (Mw) and (Control, Mw), respectively (Top). The emission spectra of the assay run at room temperature and the control assay at room temperature, (RT) and (Control, RT), respectively (Bottom). All SPCL spectra were recorded at 217 degrees (the directional emission angle) as both indicated in FIG. 11 and shown in FIG. 14. The emission spectrum from quantum dots in solution (excited with 473 nm laser) is also shown for good spectral comparison. A.U.—Arbitrary units.

FIG. 16 shows the emission spectra, for 33 nM quantum dots-streptavidin used in the MA-SPCL assay and the control MA-SPCL assay, the identical assay run at room temperature and the control assay at room temperature, which were recorded at 217 degrees in FIG. 14, as well as the emission spectrum from 33 nM quantum dots in solution, shown for spectral comparison. The assay yields a similar final luminescence intensity, after 1 minute microwave heating (≈150 au) as compared to a 30 minute room temperature incubation, c.f. FIGS. 16 top and bottom, which is very similar to that obtained in solution. This demonstrates the utility of the MA-SPCL technique and that ultra-fast directional luminescence assays can be realized. Control experiments did not yield any signal since quantum dots-streptavidin could not bind to the surface due to the absence of biotinylated BSA on the surface.

Figure 17:
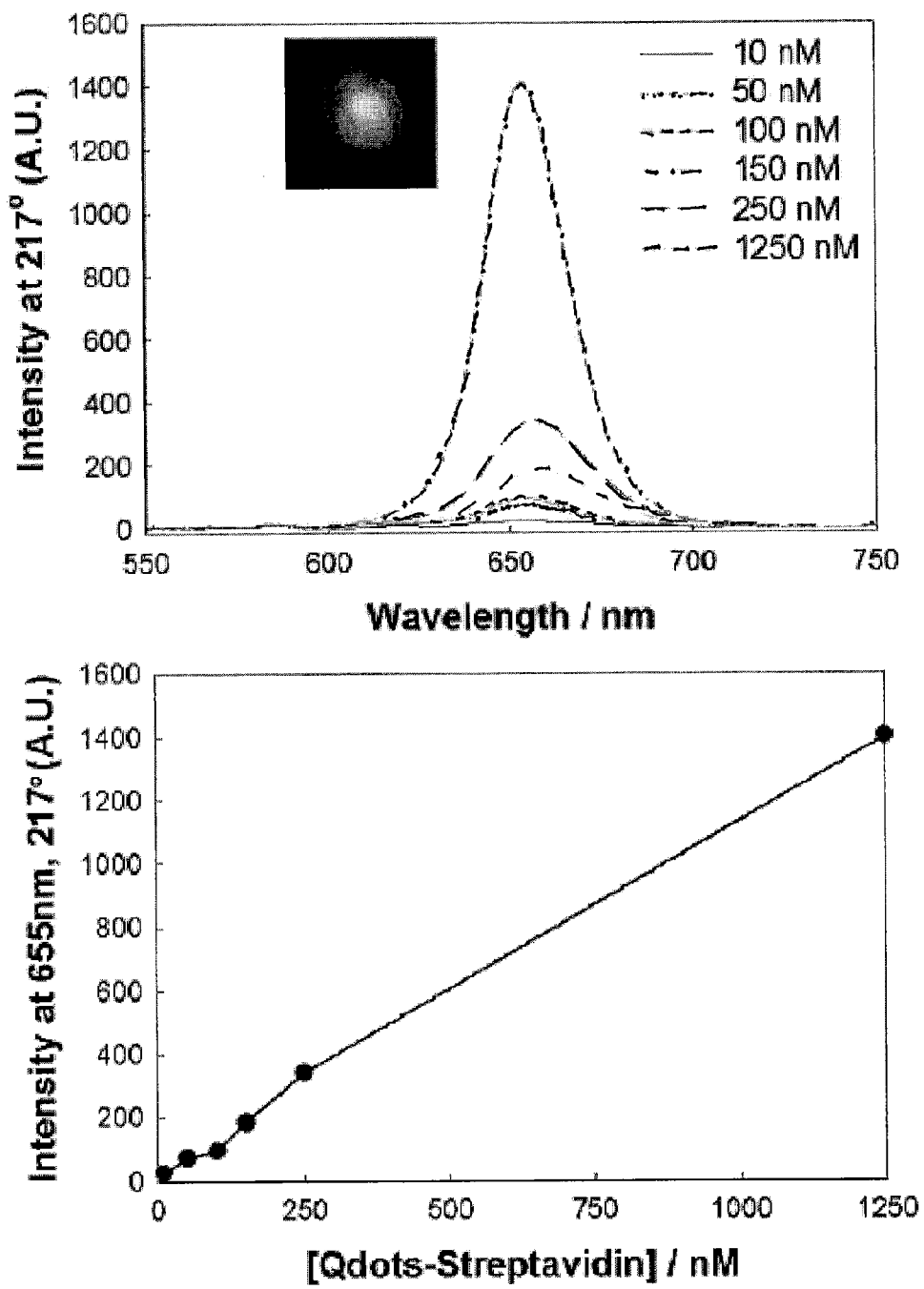
FIG. 17 shows the emission spectra of varying concentrations of quantum dots used in the MA-SPCL assay measured at 217 degrees (Top). The calibration curve, intensity at 665 nm vs. concentration of the quantum dots, is obtained from the top figure (Bottom). The real-color photograph is obtained from the MA-SPCL assay undertaken with 50 nM quantum dots streptavidin at 217 degrees, the directional emission angle. A.U.—Arbitrary units.

In order to demonstrate the utility of MA-SPCL assay in a quantitative manner, the MASPCL assay, which was undertaken with 33 nM quantum dots-streptavidin in FIG. 16, was repeated with varying concentrations of quantum dots-streptavidin, 10-1250 nM. FIG. 17-*top* shows the emission spectra of varying concentrations for the quantum dots used in the MASPCL assay measured at 217 degrees, as well as the real-color photograph obtained through the same emission filter used in the experiments. The calibration curve (intensity at 665 nm vs. concentration of the quantum dots) is obtained from the FIG. 17-T*op*, and is shown in FIG. 17-B*ottom*. As can be seen from FIG. 17, the intensity measured at 655 nm and 217 degrees in the MA-SPCL setup increases with the increasing concentration of quantum dots-streptavidin (FIG. 17-T*op*), and followed a linear trend within the range of quantum dots-streptavidin concentration used (FIG. 17-T*op*). A real-color photograph taken through an emission filter at 217 degrees is also given as a visual evidence for the surface plasmon coupled luminescence.

Figure 18:
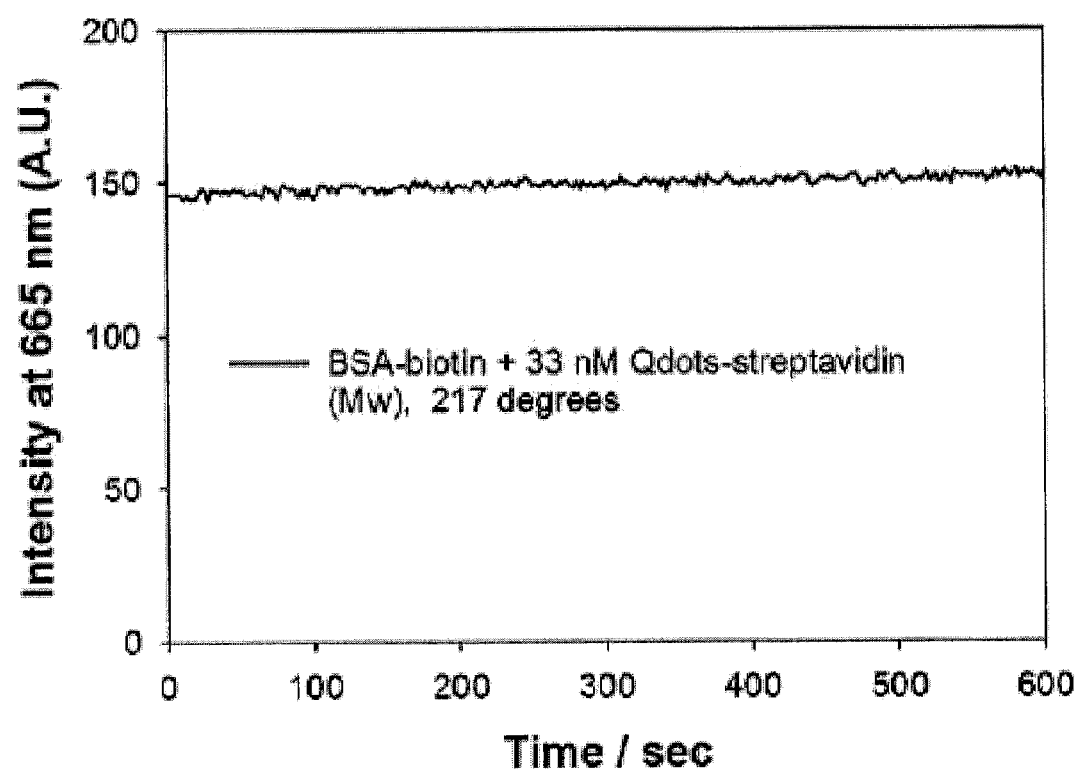
FIG. 18 shows the time-dependent emission intensity at 665 nm for 33 nM of quantum dots used in the MA-SPCL assay, measured at 217 degrees the directional emission angle. A.U.—Arbitrary units.

FIG. 18 shows the time-dependent emission intensity at 665 nm for 33 nM of quantum dots used in the MA-SPCL assay, measured at 217 degrees, the directional emission angle. The emission intensity was≈constant during 10 minutes of continuous excitation of the quantum dots on the surface. This indicates that quantum dots did not photobleach or undergo other physical changes that would alter the luminescence intensity, allowing the luminescence measurements to be performed for at least up to 10 minutes after the assay is completed. A very slight increase in intensity over time was noticed. This has been attributed to the laser induced drying of the sample during collection time. Although quantum dots are known to not photobleach as much as their fluorescent counterpart, this experiment was undertaken to emphasize the importance of evaluating the photostability of the luminescent probe used in the assay, especially when luminescent probes other than quantum dots are to be used.

The above test results show that MA-SPCL assay can be undertaken in synthetic media, where the assay components were dissolved/dispersed in phosphate buffer pH 7.0. To investigate the applicability of the new MA-SPCL technique to assays in more complex media, such as serum or even whole blood, the MA-SPCL assays using quantum dots-streptavidin were repeated in buffer, serum and whole blood. FIG. 18-T*op* shows the emission spectra for 33 nM quantum dots used in the MA-SPCL assay measured at 217 degrees in different media. The peak intensity from the assay using quantum dots (at 655 nm) in serum was 75% of that peak intensity in buffer, indicating that the MA-SPCL assays can be easily done in serum with very large signal to noise ratios, 12.5 (75:6). Interestingly, the MA-SPCL assay using quantum dots in whole blood still yielded a measurable signal (20% that of MA-SPCL assay in buffer) with a signal to noise ratio of approximately 3, given that the S/N>3 for fluorescence-based assays is considered acceptable (Lakowicz, 1999).

Figure 19:
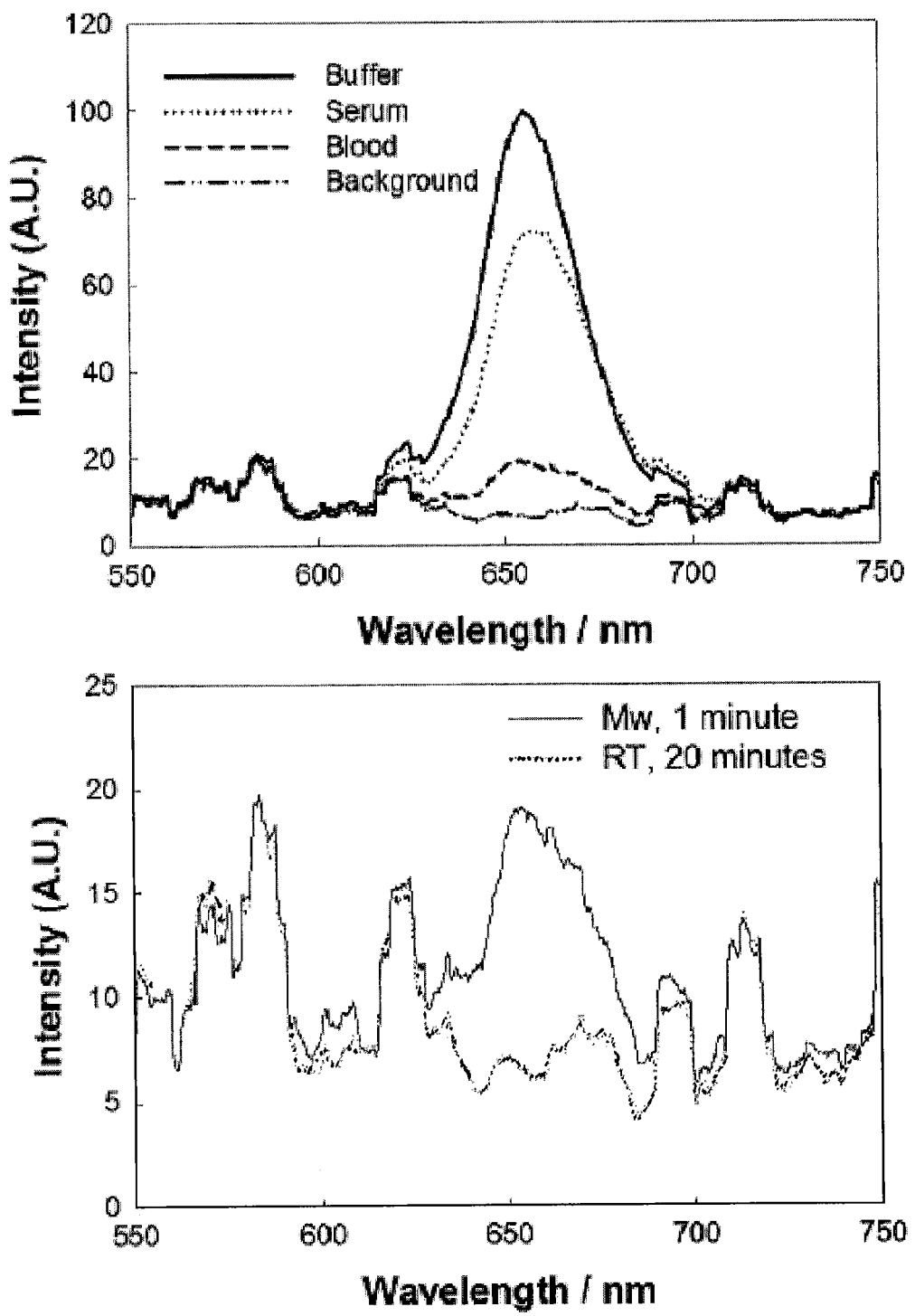
FIG. 19 shows the emission spectra for 33 nM quantum dots used in the MA-SPCL assay measured at 217 degrees in different media (Top). The background signal is obtained from the sample that only contains biotinylated-BSA (quantum dots not used) and was ≈6 AU. The peak intensity obtained from the assay in buffer is normalized to 100 A.U. (the intensities from assays in serum and whole blood and the background are adjusted relative to intensity in buffer) for an easy comparison of the luminescent signal in percentage terms. The MA-SPCL assay (Mw, 1 minute) and the SPCL assay at room temperature (RT, 20 min) performed in whole blood measured at 217 degrees (Bottom). A.U.—Arbitrary units.

To further demonstrate the benefits of the MA-SPCL technique for whole blood assays, the assay using quantum dots-streptavidin was repeated in whole blood both with microwave heating and at room temperature for comparison. FIG. 19-B*ottom* shows the MA-SPCL assay (Mw, 1 minute) and the SPCL assay at room temperature (RT, 20 min) performed in whole blood measured at 217 degrees. While the assay that was microwave heated (accelerated) for 1 minute yielded a measurable signal, the assay that was undertaken at room temperature for 20 minutes did not yield any signal. This is due to the fact that the whole blood used in the assay at room temperature coagulated within 10 to 15 minutes, entrapping the quantum dots, resulting in no luminescence signal change. On the other hand, when the whole blood is microwaved for 1 minute, significantly less coagulation of the blood occurred enabling the assay to be completed a significant benefit to our approach to whole blood assays. It is important to note that the concentration of the quantum dots (33 nM) used in the whole blood MA-SPCL assay, was closer to the lower detection limit found here (FIG. 17), promising the use of the MA-SPCL assay in whole blood for a concentration range similar to that of the assay in buffer. This is made possible by the use of microwave heating that significantly reduces the assay time, so that the assay could be carried our in whole blood before the blood coagulates, while also decreasing the non-specific interactions. In this regard, numerous reports have employed microwaves and whole blood (Hirsch, 2003; Herron, 1997), strongly suggesting that whole blood components are not damaged by microwave exposure.

Thus the results show that using the microwave-Accelerated Surface Plasmon Coupled Luminescence (MA-SPCL) is a fast and sensitive assays in buffer, serum and whole blood. In this regard, a 50 nm thick gold disk, 5 mm diameter, with a black body is used as the substrate for the MA-SPCL assays. It was found that the gold disk with the black body withstood the microwave exposures for up to 5 minutes enabling the completion of the assay, while the larger-sized 50 nm continuous gold film sparked, arced and was destroyed within 10 seconds. In addition, the gold disk with the black body retained its physical properties after multiple assay washes. The feasibility of the MA-SPCL technique was demonstrated with a model assay using streptavidin conjugated quantum dots and surface-bound biotinylated BSA.

Control experiments were also undertaken to determine the extent of the non-specific interactions. With the MA-SCPL technique, 10-1250 nM of streptavidin was detected within 1 minute, which corresponds to ≈30-fold faster kinetics as compared to the assay undertaken at room temperature. The accelerated assay kinetics was made possible by the heating of gold disk by microwaves, resulting in a slight increase in the bulk solution temperature, with higher temperature jumps close-to the gold surface. Moreover, highly directional coupled luminescence emission (at 655 nm, 217 degrees through the coupling prism) from quantum dots enabled the realization of sensitive luminescence measurements. The combined effect of microwaves for faster assay kinetics with surface plasmon-coupled luminescence for sensitive measurements also made possible the demonstration of the use of MA-SPCL technique for assays to be run in complex media such as human serum and whole blood, while the same assay could not be performed at room temperature due to the coagulation of blood. In the MA-SPCL assay run in serum and whole blood, the luminescence intensity from 33 nM quantum dots was 75% and 20% that of the luminescence intensity from the assay run in buffer, with a signal to noise ratio of 12.5 and 3, respectively.

These findings suggests that highly sensitive and ultrafast luminescence assays can realized in synthetic media as well as more complex media.

Example 4

Figure 12:
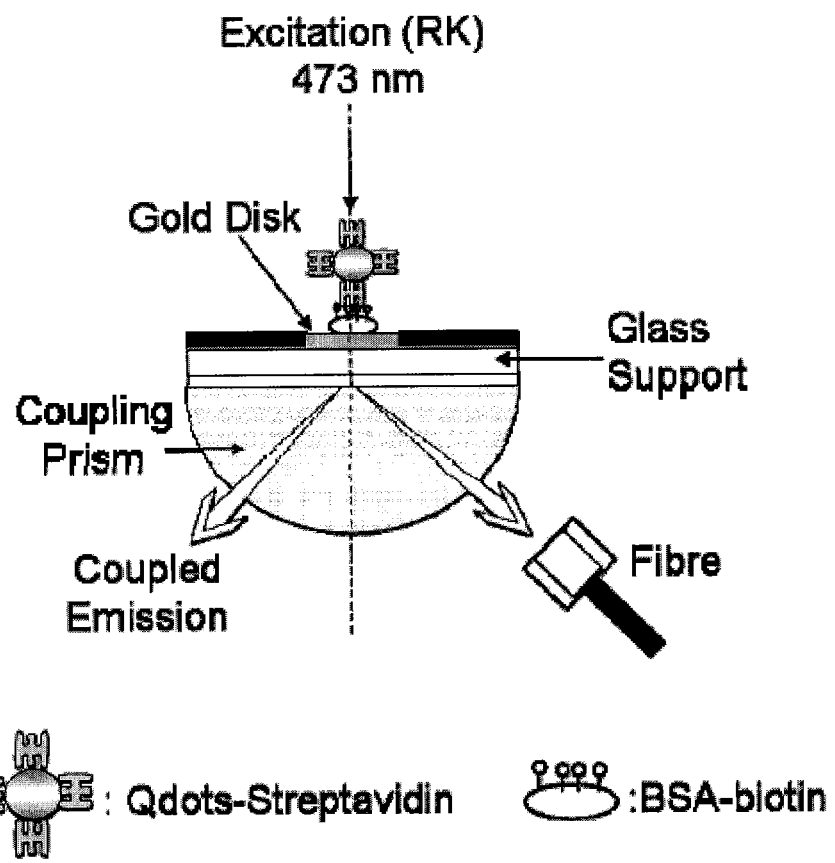
FIG. 12 shows the optical set-up for microwave-accelerated surface plasmon coupled luminescence (MA-SPCL) bioassays. The sample is excited directly in the reverse Kretschmann (RK) configuration. The assay is undertaken on the gold-coated glass slide, which is attached to the glass prism with index matching fluid. The two arrows on the left side show the directional coupled luminescence emission. Figure is not drawn to scale.
Figure 20:
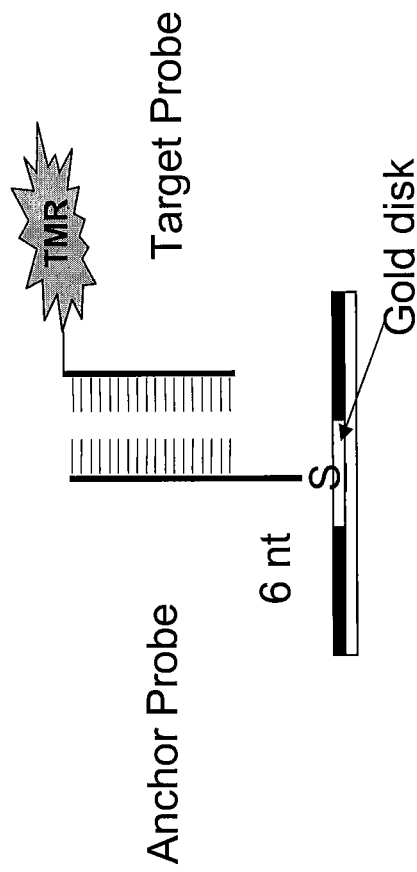
FIG. 20 shows the experimental design depicting the organization of the DNA oligomers on gold disks used for the detection of Hepatitis C. The lower panel shows the structures of the DNA oligomers used that being SEQ ID NO; 1 used for an anchor probe and SEQ ID NO: 2 having the sequence of the target species.

The gold disks created in Example 3 and shown in FIG. 11 with the optical setup shown in FIG. 12 were used for the detection of Hepatitis C using the technique of microwave accelerated surface plasmon coupling luminescence (MASPCL) as shown in FIG. 20.

A capture assay was used to detect specific DNA sequences of the target probe. An anchor probe having the sequence cttltttgatgcacg gtctacgaga ccgg gggg tcctgg aggctgcacga (SEQ ID NO: 1) was attached to a thio binding group for attachment to the metallic surface by an overnight incubation at 4° C. in a humidified chamber. Excess thiol-conjugated oligo was removed by washing the surface with the hybridization buffer several times. The TAMRA-linked target probe having the complementary DNA sequence (ctacgtgc cagatgctctggccccccaggacc tccgacgtgct) (SEQ ID NO; 2) was label with TMR at the 5' end. This procedure brings the fluorophore to a distance, approximately 10 nm, from the surface of the gold metallic surface.

The angle-dependent polarized or scattered emissions from the metallic surfaces were measured using g using an X-Y rotating stage (Edmund Optics) with a fiber optic mount. The metallic structures can be illuminated with scattered or polarized laser sources with a neutral density filter being used to adjust the laser intensity. The angle-dependent light from the metallic surfaces can be collected through a dichroic sheet polarizer (Edmund optics) into a 600 micron broad wavelength fiber that was connected to an Ocean Optics HD2000 spectrofluorometer. The photostability of metallic surfaces can be measured by simply observing the polarized or scattered intensity at different angles for a specific length of time, such as 30 or 45 minutes. Preferably, the angles for measuring intensities is varied and predetermined dependent on the metal surface, shape and density of metallic particles. The electromagnetic radiation may be applied by a monochromatic laser light at a frequency similar to plasmon absorption maxima of the metallic surfaces.

Figure 21:
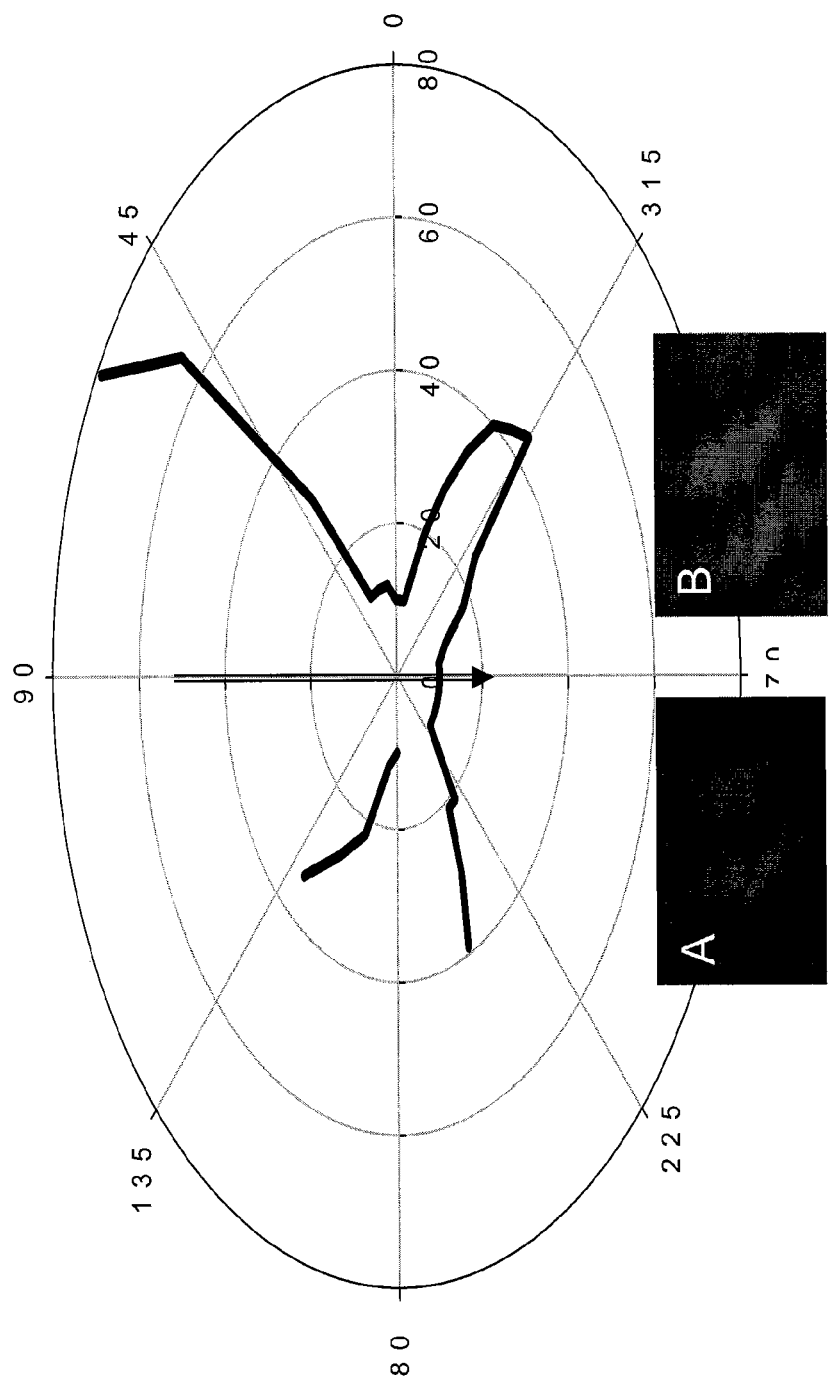
FIG. 21 shows the angular distribution of luminescence for 10 nM of TAMRA-labeled target DNA used in the MA-SPCL assay. Photographs (A) and (B) are showing TAMRA emission at 310 and 315 degrees obtained through the same emission filter.
Figure 22:
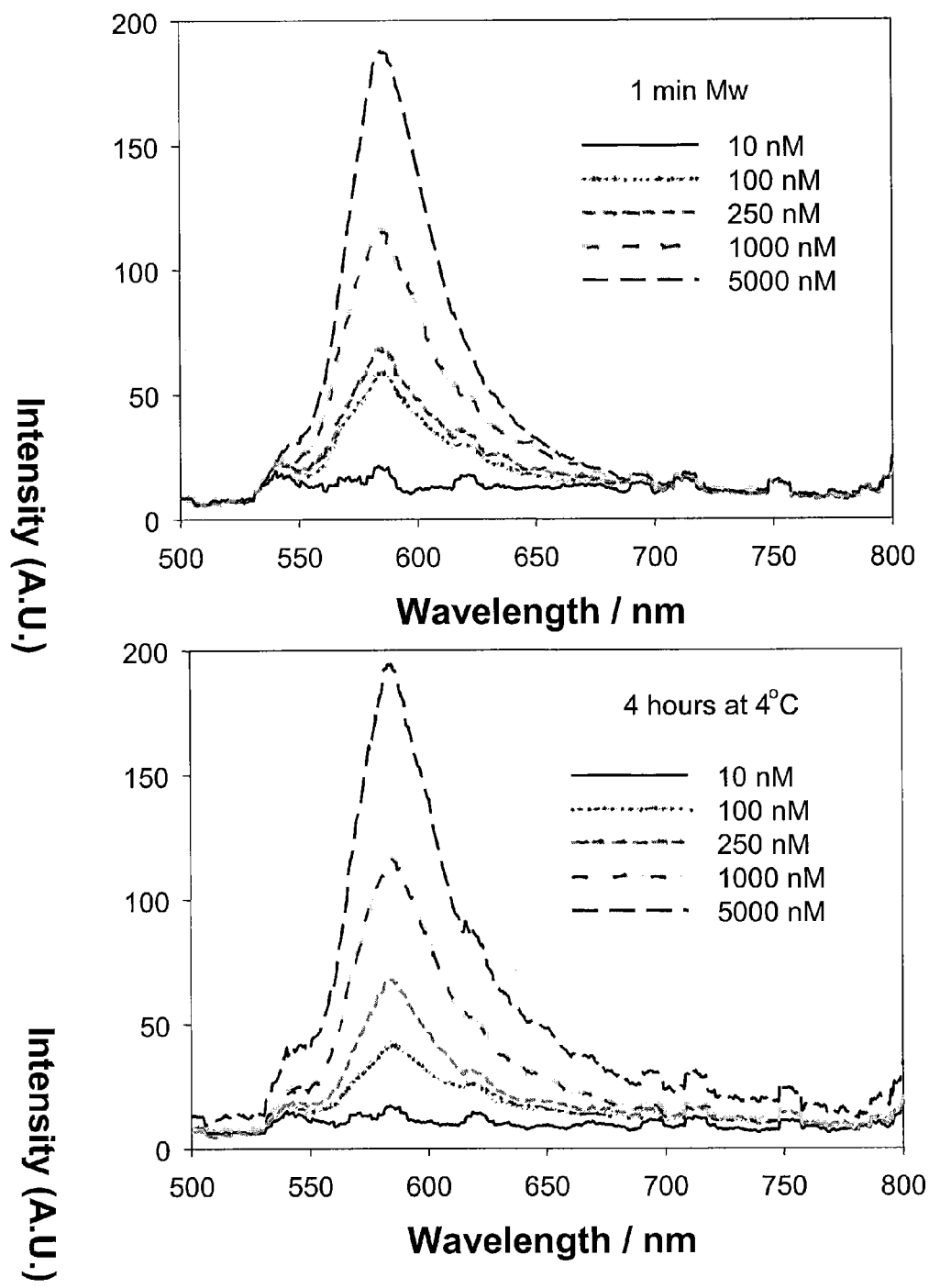
FIG. 22 shows the emission spectra of varying concentrations of TAMRA-labeled target DNA used in the MA-SPCL assay (Top) and the same assay measured at room temperature (Bottom) all measured at 315 degrees.
Figure 23:
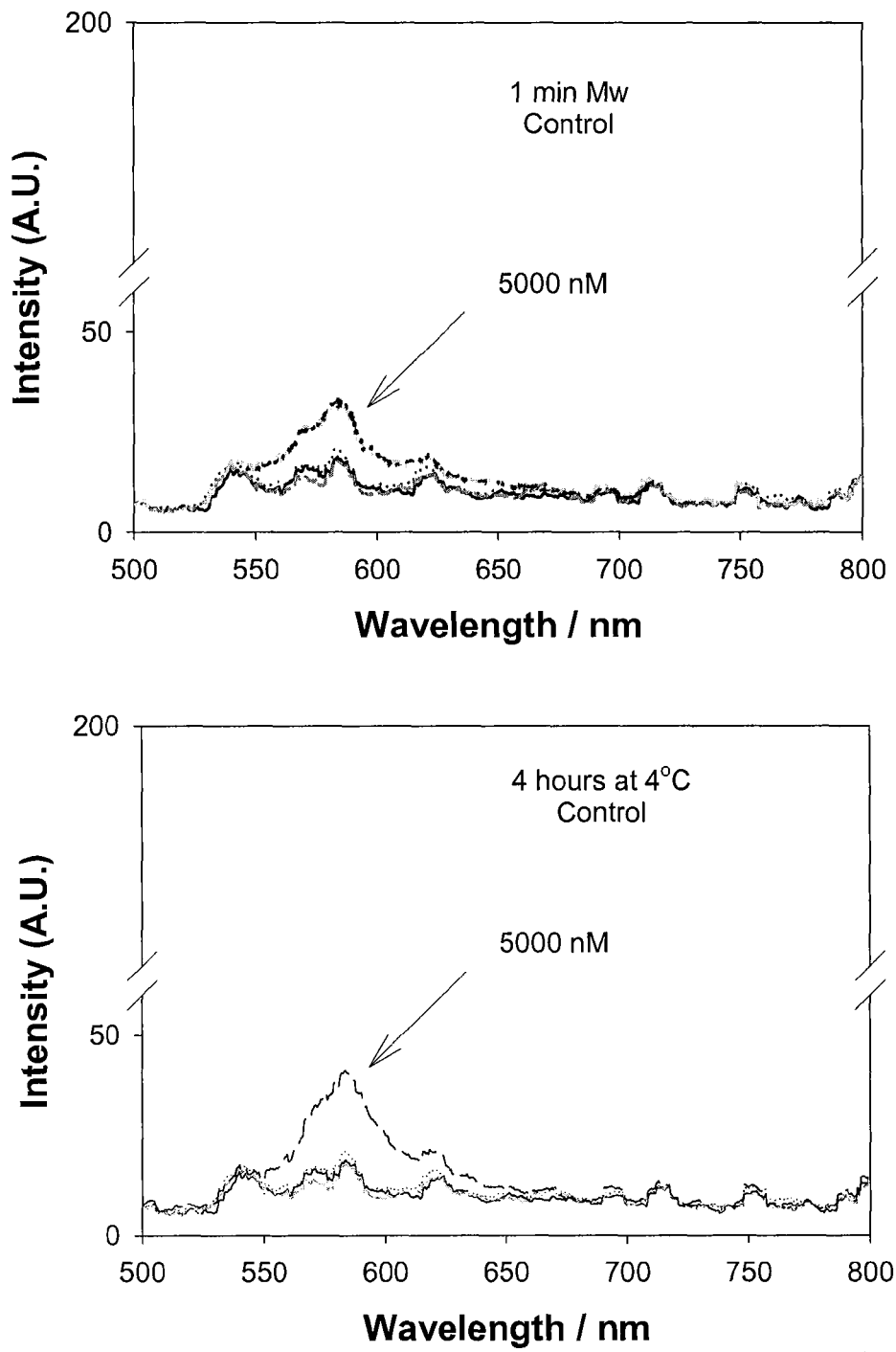
FIG. 23 shows the emission spectra of varying concentrations of TAMRA-labeled target DNA used in the MA-SPCL control assay (Top) and room temperature control assay (Bottom) measured at 315 degrees. The anchor probe is omitted from the surface in these control assays.

Luminescence emission spectra of TAMRA-labeled oligo with RNA substrate hybridized to the thiolated-oligo anchor probe are shown in FIGS. 21 A and B along with the angular distribution of 10 nM of TAMRA-labeled target DNA. FIG. 22 shows the emission spectra of varying concentrations of TAMRA-labeled DNA with the use of microwaves top and then at room temperature. Clearly the use of low power microwaves increased the reaction time exponentially. FIG. 3 shows the results when there was no anchor probe for binding of the target DNA sequence. As such, the intensity was almost non existent due to the fact that TAMRA system is only activated when the target probe binds to the anchor probe.

Figure 24:
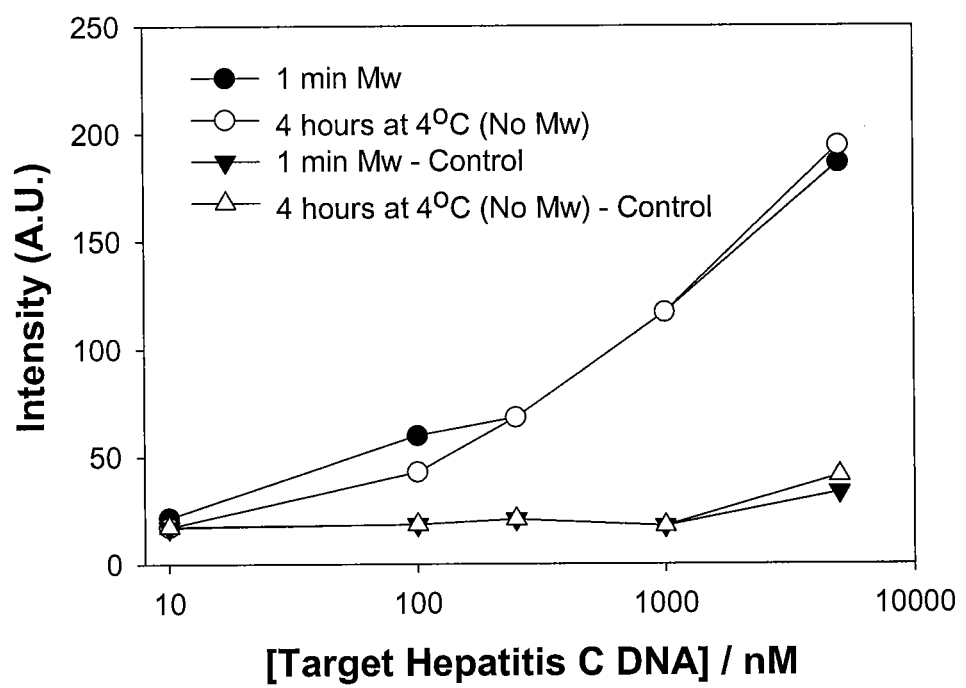
FIG. 24 shows the calibration curves for MA-SPCL and room temperature Hep C assay with respective control experiments/samples, as obtained from FIGS. 22 and 23.

FIG. 24 shows the calibration curve for the microwaved sample compared to the non-microwaved sample. Again it is evident that the time for reactions is exponentially increased when using the microwave.

Figure 25:
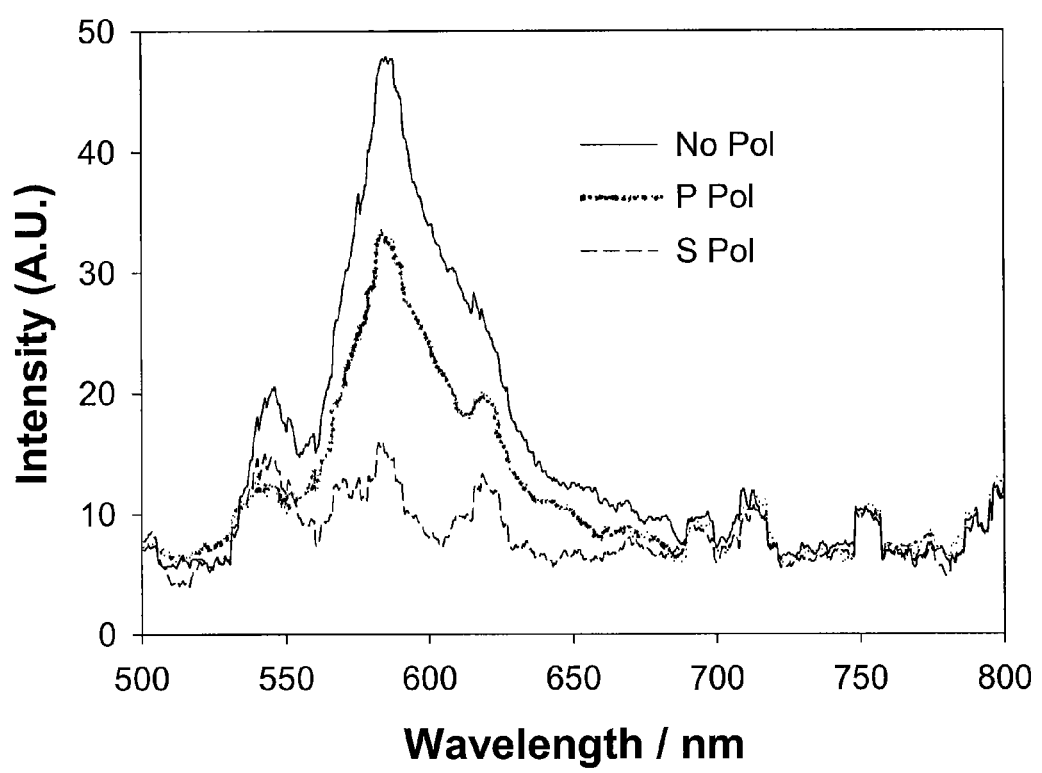
FIG. 25 shows the polarization dependent emission from TAMRA-labeled target DNA used in the MA-SPCL assay. The emission measured through the gold disk is predominantly p-polarized.

Polaraization dependency of the emission from the TAMRA-labeled target DNA can be seen in FIG. 25 wherein the emission is measured through the gold disk and is predominately p-polarized.

Although the invention has been described with respect to specific embodiments, the details are not to be construed as limitations, for it will be apparent that various embodiments, changes and modifications may be resorted to without departing from the spirit and scope thereof, and it is understood that such equivalent embodiments are intended to be included within the invention as hereinafter claimed.

References

The contents of all references are hereby incorporated by reference herein for all purposes.

Akerman, M. E., Chan, W. C. W., Laakkonen, C., Bhatia, S. N., and Ruoslahti, E. 2002. Nanocrystal targeting in vivo. Proc. Nat. Acad. Sci., 99:12617-12621.

Aslan, K., and Geddes, C. D. 2005. Microwave-accelerated metal-enhanced fluorescence: Platform technology for ultrafast and ultrabright assays. Anal. Chem. 77:8057-8067.

Aslan, K., and Geddes, C. D., 2006a. Microwave-accelerated Metal-enhanced Fluorescence (MAMEF): Application to ultra fast and sensitive clinical assays. J. of Fluorescence. 16:3-8.

Aslan, K., Malyn, S. N., and Geddes, C. D. 2006b. Fast and sensitive DNA hybridization assays using microwave-accelerated metal-enhanced fluorescence. Biochem. Biophys. Res. Com. 348: 612-617.

Aslan, K., Perez-Luna, V. H, 2002. Langmuir 18, 6059-6065.

Baker, G. A., Pandey, S., and Bright, F. V. 2000. Extending the reach of immunoassays to optically dense specimens by using two-photon excited fluorescence polarization. Anal. Chem. 72:5748-5752.

Bange, A., Halsall, H. B., and Heineman, W. R. 2005. Microfluidic immunosensor systems. Biosens. Bioelectron. 20:2488-2503.

Baziard Y., Breton, S., Toutain, S., and Gourdenne, A. 1988. Dielectric-properties of aluminum powder epoxy-resin composites. Eur. Polym. J., 24:521-526.

Borrebaeck, C. A. K. 2000. Antibodies in diagnostics—from immunoassays to protein chips. Immunol. Today. 21:379-382.

Bruchez, M., Jr., Maronne, M., Gin, P., Weiss, S., and Alivisatos, S. P. 1998. Semiconductor nanocrystals as fluorescent biological labels. Science, 281, 2013-2015.

Chan, W. C. W., and Nie, S. 1998. Quantum dot bioconjugates for ultrasensitive nonisotopic detection. Science, 281: 2016-2018.

Chan, W. C. W., Maxwell, D. J., Gao, X., Bailey, R. E., Han, M., and Nie, S. 2002. Luminescent quantum dots for multiplexed biological detection and imaging. Curr. Opin. Biotechnol. 13:40-46.

Chicoine, L., and Webster, P. 1998. Effect of microwave irradiation on antibody labeling efficiency when applied to ultrathin cryosections through fixed biological material. Micro Res. Tech. 42:24-32.

Choi, S., Choi, E. Y., Kim, D. J., Kim, J. H., Kim, T. S., and Oh, S. W. 2004. A rapid, simple measurement of human albumin in whole blood using a fluorescence immunoassay (I). Clin. Chim. Acta. 339:147-156.

Dubertret, B., Skourides, P., Norris, D. J., Noireaux, V., Brivanlou, A. H., and Libchaber, A. 2002. In vivo imaging of quantum dots encapsulated in phospholipid micelles. Science, 298:1759-1762.

Gomez-Hens, A., and Aguilar-Caballos, M. P. 2003. Stopped-flow fluorescence polarization immunoassay. Comb. Chem. High Throughput Screen. 6:177-182.

Green, N. M. 1975. Adv. Protein Chem. 29: 85-133.

Gryczynski, I., Malicka, J., Jiang, W., Fischer, H., Chan, W. C. W., Gryczynski, Z., Grudzinski, W., and Lakobicz, J. R. 2005. Surface-plasmon-coupled emission of quantum dots. J. Phys. Chem. B. 109:1088-1093.

Hemmila L. A. 1992. Applications of Fluorescence in Immunoassays, John Wiley and Sons: New York.

Herron, D. M., Grabowy, R., Connolly, R., and Schwaitzberg, S. D. 1997. The limits of bloodwarming: Maximally heating blood with an inline microwave bloodwarmer. J. Trauma-Injury Infection and Critical Care. 43:219-226.

Hirsch, J., Menzebach, A., Welters, I. D., Dietrich, G. V., Katz, N., and Hempelmann, G. 2003. Indicators of erythrocyte damage after microwave warming of packed red blood cells. Clin. Chem., 49:792-799.

Kambhampati, D., Nielsen, P. E., and Knoll, W. Biosens. Bioelectron. 2001, 16 (9-12), 1109-1118.

Lakowicz, J. R. 1999. Principles of Fluorescence Spectroscopy, Kluwer, New York.

Lakowicz, J. R. 2004. Radiative decay engineering 3. Surface plasmon-coupled directional emission. Anal. Biochem. 324:153-169.

Liebermann, T., and Knoll, W. 2000a. Surface-plasmon field-enhanced fluorescence spectroscopy. Colloids Surf. 171: 115-130.

Liebermann, T., Knoll, W., Sluka, P., and Hermann, R. 2000b. Complement hybridization from solution to surface-attached probe-oligonucleotides observed by surface-plasmon-field-enhanced fluorescence spectroscopy. Colloids Surf. 169:337-350.

Lofas, S., Malmqvist, M., Ronnberg, I., Stenberg, E., Liedberg, B., and Lundstrom, I. 1991. Bioanalysis with surface-plasmon resonance. Sensors and Actuators B. 5:79-84.

Lofas, S., Johnson, B., J. 1990. Chem. Soc. Chem. Commun. 1526.

Lövgren, T., and Pettersson, K. 1990. Time-resolved fluoroimmunoassay: advantages and limitations. In Luminescence Immunoassay and Molecular Applications, Van Dyke, K., and Van Dyke, R. (Eds.), CRC Press, Boca Raton, Fla., 233-253.

Madden, V. J. Micro Microanalysis 4, 1998, 854-855.

Micheva, K. D., Holz, R. W., and Smith, S. J. 2001. Regulation of presynaptic phosphatidylinositol 4,5-biphosphate by neuronal activity. J. Cell Biol., 154:355-368.

Neumann, T., Johansson, M. L., Kambhampati, D., and Knoll, W. 2002. Surface-plasmon fluorescence spectroscopy. Adv. Funct. Mater., 12, 575-585.

Ozinkas, A. J. 1994. Principles of Fluorescence Immunoassay, In Topics in Fluorescence Spectroscopy, Lakowicz, J. R., Ed., Plenum Press: New York. Vol. 4.

Petrali, J. P., and Mills K. R. Micro Microanalysis, 1998, 114-115.

Rangell, L. K., and Keller, G. A. 2000. Application of microwave technology to the processing and immunolabeling of plastic-embedded and cryosections. J. Histochem. Cytochem. 28:1153-1160.

Rassner, U. A., Crumrine, O. A., Nau, P., and Elias, P. M. 1997. Microwave incubation improves lipolytic enzyme preservation for ultrastructural cytochemistry. Histochem. J. 29: 387-392.

Robelek, R., Niu, L., Schmid, E. L., and Knoll, W. 2004. Multiplexed hybridization detection of quantum dot-conjugated DNA sequences using surface plasmon enhanced fluorescence microscopy and spectrometry. Anal. Chem. 76: 6160-6165.

Schichnes, D., Nemson, J., Sohlberg, L., and Ruzin, S. E. Micro Microanalysis 4, 1999, 491-496.

Schray, C. L., Metz, A. L., and Gough, A. W. 2002. Microwave-Enhanced Fixation for Rapid Preparation of Tissue Sections for Microscopic Evaluation. Histologic. 35(1):7-12.

Schutt, M., Krupka, S. S., Milbradt, A. G., Deindl, S., Sinner, E. K., Oesterhelt, D., Renner, C., and Moroder, L. 2003. Photocontrol of cell adhesion processes: Model studies with cyclic azobenzene-RGD peptides. Chem. Biol., 10(6):487-90.

Tarkkinen, P., Palenius, T., and Lovgren, T. 2002. Ultrarapid, ultrasensitive one-step kinetic immunoassay for C-reactive protein (CRP) in whole blood samples: Measurement of the entire CRP concentration range with a single sample dilution. Clin. Chem. 48:269-277.

Van Dyke, K., and Van Dyke, R., Eds. 1990. Luminescence Immunoassay and Molecular Applications, CRC Press: Boca Raton, Fla.

Vo-Dinh, T., Sepaniak, M. J., Griffin, G. D., and Alarie, J. P. 1993. Immunosensors: Principles and Applications. Immunomethods, 3:85-92.

von Lode, P., Rainaho, J., and Pettersson, K. 2004. Quantitative, wide-range, 5-minute point-ofcare immunoassay for total human chorionic gonadotropin in whole blood. Clin. Chem. 50:1026-1035.

Weisbecker, C S., Merritt, M. G., Whitesides, G. M., 1996. Langmuir 12, 3763-3772.

Whittaker, A. G., and Mingos, D. M. P. 1993. Microwave-assisted solid-state reactions involving metal powders and gases. J. Chem. Soc. Dalton Trans. 16:2541-2543.

Wilchek, M., and Bayer, E. A. 1990. Methods of Enzymology, Vol. 184, Academic Press, San Diego.

What is claimed is:

1. A microwave-accelerated metal-enhanced method for detection of biological target species in a testing sample comprising:
   a) providing a detection system comprising: a glass or polymeric surface substrate comprising a multiplicity of metallic nanostructures positioned thereon, wherein the metallic nanostructures are spherical-like particles having a diameter from about 10 nm to 60 nm, wherein the metallic nanostructures are modified with coupling agents for binding with target species suspected of being in the testing sample, and a fluorescing entity having binding affinity for a specific epitope, functional group or nucleotide sequence on the target species, wherein the target species comprises a protein, peptide, small molecule, or DNA;
   b) introducing the testing sample to the glass or polymeric surface substrate comprising a multiplicity of metallic nanostructures positioned thereon, wherein the testing sample is suspected of containing at least one target species for binding with the coupling agents; and then applying microwave energy to the testing sample at low power to cause an increase in heat in the detection system and increase the binding kinetics of a chemical reaction between the target species in the testing sample and coupling agents, wherein the microwave energy has an intensity in a range of about 0.0001 µW/cm$^2$ to about 1000 µW/cm$^2$ and increases binding of any target species in the testing sample to the coupling agent;
   c) introducing the fluorescing entity having binding affinity for the target species, wherein such fluorescing entity binds with any target species in the test sample and wherein the specific epitope, functional group or nucleotide sequence is located on the target species at a distance from the metallic nanostructures for positioning the fluorescing entity a distance from about 4 nm to about 30 nm from the metallic nanostructures upon binding of the fluorescing entity with the target species;
   d) applying an excitation energy to at least the fluorescing entity; and
   e) measuring a surface plasmonic emission spectrum from said metallic nanostructures and a fluorescence emission spectrum from said fluorescing entity; and
   f) detecting, using a computer processor, the presence and amount of said biological target species based on said fluorescence emission spectra.

2. The detection method of claim 1, wherein the microwaves have a frequency in a range of from about $10^8$ to about $10^{12}$ Hz.

3. The detection method of claim 1, wherein the metallic nanostructures comprise metal selected from among gold, copper, silver, aluminum, and alloys including one or more of said metals.

4. The detection method of claim 1, wherein said microwaves do not degrade the target and testing sample.

5. The detection method of claim 1, wherein the spherical-like particles are positioned from at least about 50 nm from each other.

* * * * *